(12) United States Patent
Soth et al.

(10) Patent No.: US 10,428,057 B2
(45) Date of Patent: Oct. 1, 2019

(54) BICYCLO[1.1.1]PENTANE INHIBITORS OF DUAL LEUCINE ZIPPER (DLK) KINASE FOR THE TREATMENT OF DISEASE

(71) Applicant: Board of Regents, The University of Texas System, Austin, TX (US)

(72) Inventors: Michael J. Soth, Sugar Land, TX (US); Gang Liu, Sugar Land, TX (US); Kang Le, Sugar Land, TX (US); Jason Cross, Pearland, TX (US); Philip Jones, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/121,198

(22) Filed: Sep. 4, 2018

(65) Prior Publication Data

US 2019/0092764 A1 Mar. 28, 2019

Related U.S. Application Data

(62) Division of application No. 15/836,442, filed on Dec. 8, 2017, now Pat. No. 10,093,664.

(60) Provisional application No. 62/431,504, filed on Dec. 8, 2016.

(51) Int. Cl.

| | | |
|---|---|---|
| *A61K 31/5377* | (2006.01) | |
| *A61K 31/4439* | (2006.01) | |
| *C07D 413/14* | (2006.01) | |
| *C07D 401/04* | (2006.01) | |
| *C07D 471/04* | (2006.01) | |
| *C07D 417/14* | (2006.01) | |
| *C07D 401/14* | (2006.01) | |
| *C07D 405/14* | (2006.01) | |

(52) U.S. Cl.
CPC ......... *C07D 413/14* (2013.01); *C07D 401/04* (2013.01); *C07D 401/14* (2013.01); *C07D 405/14* (2013.01); *C07D 417/14* (2013.01); *C07D 471/04* (2013.01)

(58) Field of Classification Search
CPC ............ A61K 31/4439; A61K 31/5377; A61K 31/496
USPC ...................................... 514/341, 235.8, 252
See application file for complete search history.

(56) References Cited

U.S. PATENT DOCUMENTS

| | | |
|---|---|---|
| 10,093,664 B2 | 10/2018 | Soth |
| 2005/0009764 A1 | 1/2005 | Burger |
| 2009/0203705 A1 | 8/2009 | Biagetti |
| 2012/0322795 A1 | 12/2012 | Berry |
| 2015/0080367 A1 | 3/2015 | Cohen |
| 2016/0002228 A1 | 1/2016 | Estrada |
| 2016/0052940 A1 | 2/2016 | Estrada |
| 2016/0257690 A1 | 9/2016 | Kinsella |
| 2018/0057507 A1 | 3/2018 | Soth |

FOREIGN PATENT DOCUMENTS

| | | |
|---|---|---|
| CN | 104119340 | 12/2014 |
| WO | 2013174780 | 11/2013 |
| WO | 2014111496 | 7/2014 |
| WO | 2014177060 | 11/2014 |
| WO | 2014177524 | 11/2014 |
| WO | 2015091889 | 6/2015 |
| WO | 2015134710 | 9/2015 |
| WO | 2016161160 | 10/2016 |
| WO | 2018044808 | 3/2018 |
| WO | 2018107072 | 6/2018 |

OTHER PUBLICATIONS

International Application No. PCT/US2017/021784; International Search Report and Written Opinion of the International Searching Authority, dated Mar. 10, 2017; 12 pages.
International Application No. PCT/US2017/048941; International Search Report and Written Opinion of the International Searching Authority, dated Dec. 21, 2017; 10 pages.
International Application No. PCT/US2017/065385; International Search Report and Written Opinion of the International Searching Authority, dated Apr. 5, 2018; 12 pages.
Oetjen, E. et al., "Dual leucine zipper kinase (MAP3K12) modulators: a patent review (2010-2015)", Expert Opinion on Therapeutic Patents 2016, 26(5):607-16.
Patel, S. et al., "Discovery of Dual Leucine Zipper Kinase (DLK, MAP3K12) Inhibitors with Activity in Neurodegeneration Models",. J. Med. Chem., 58(1):401-18, (2015).
Patel, S. et al., . "Scaffold-Hopping and Structure-Based Discovery of Potent, Selective and Brain Penetrant N-(1H-Pyrazol-3-yl)pyridin-2-amine Inhibitors of Dual Leucine Zipper Kinase (DLK, MAP3K12)", J. Med. Chem., 58 (20):8182-99, (2015).

(Continued)

*Primary Examiner* — Charanjit Aulakh
(74) *Attorney, Agent, or Firm* — Dennis A. Bennett; Cynthia Hathaway; John Desper

(57) ABSTRACT

Disclosed herein are compounds which inhibit the kinase activity of dual leucine zipper (DLK) kinase (MAP3K12), pharmaceutical compositions, and methods of treatment of DLK-mediated diseases, such as neurological diseases that result from traumatic injury to central nervous system and peripheral nervous system neurons (e.g. stroke, traumatic brain injury, spinal cord injury), or that result from a chronic neurodegenerative condition (e.g. Alzheimer's disease, frontotemporal dementia, Parkinson's disease, Huntington's disease, amyotrophic lateral sclerosis, spinocerebellar ataxia, progressive supranuclear palsy, Lewy body disease, Kennedy's disease, and other related conditions), from neuropathies resulting from neurological damage (chemotherapy-induced peripheral neuropathy, diabetic neuropathy, and related conditions) and from cognitive disorders caused by pharmacological intervention (e.g. chemotherapy induced cognitive disorder, also known as chemobrain).

46 Claims, No Drawings

Specification includes a Sequence Listing.

(56) References Cited

OTHER PUBLICATIONS

PubChem CID: 122510487, Create Date: Dec. 8, 2016, 10 pages.
U.S. Appl. No. 15/688,554; Non-Final Office Action dated Sep. 28, 2018; 31 pages.
U.S. Appl. No. 15/836,442; Examiner Initiated interview summary dated May 29, 2018; 1 page.
U.S. Appl. No. 15/836,442; Notice of Allowance dated Jun. 5, 2018, 10 pages.

BICYCLO[1.1.1]PENTANE INHIBITORS OF DUAL LEUCINE ZIPPER (DLK) KINASE FOR THE TREATMENT OF DISEASE

This application is a divisional of U.S. application Ser. No. 15/836,442, filed Dec. 8, 2017, which claims the benefit of priority of U.S. Provisional Application No. 62/431,504, filed Dec. 8, 2016, the disclosures of which are hereby incorporated by reference as if written herein in their entireties.

Disclosed herein are new substituted bicyclo[1.1.1]pentane compounds and compositions and their application as pharmaceuticals for the treatment of disease. Methods of inhibition of the kinase activity of dual leucine zipper in a human or animal subject are also provided for the treatment of diseases such as neurological diseases that result from traumatic injury to central nervous system and peripheral nervous system neurons, neurodegenerative conditions, neuropathies resulting from neurological damage, and treatment of pain and cognitive disorders caused by pharmacological intervention.

Dual leucine zipper kinase (DLK) is a member of the mixed lineage kinase (MLK) family that is required for stress-induced neuronal activation of c-Jun N-terminal kinases (JNK). In turn, JNK is implicated in pathways important to cellular regulation including apoptosis and cell proliferation. JNK has been implicated in both naturally occurring cell death and pathological death of neurons.

Novel compounds and pharmaceutical compositions, certain of which have been found to inhibit the kinase activity of DLK have been discovered, together with methods of synthesizing and using the compounds including methods for the treatment of DLK-mediated diseases in a patient by administering the compounds.

DETAILED DESCRIPTION

In certain embodiments of the present invention, compounds have structural Formula I:

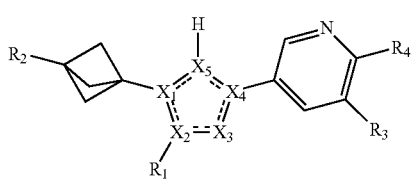

or a salt thereof, wherein:
- $X_1$ is selected from C and N;
- $X_2$ is selected from C and N;
- exactly one of $X_1$ and $X_2$ is N;
- $X_3$ is N;
- $X_4$ and $X_5$ are C;
- $X_1$, $X_2$, $X_3$, $X_4$, and $X_5$ form a five membered heteroaryl;
- $R_1$ is selected from alkyl, cycloalkyl, and heterocycloalkyl, any of which is optionally substituted with one to three $R_5$ groups;
- $R_2$ is H or is selected from alkyl, amino, aryl, cycloalkyl, haloalkyl, heteroalkyl, heteroaryl, heterocycloalkyl, and sulfonylalkyl, any of which is optionally substituted with one to three $R_6$ groups;
- $R_3$ is selected from H, alkyl, (alkoxy)alkyl, (arylalkoxy)alkyl, (heteroarylalkoxy)alkyl, cyano, cycloalkyl, halo, haloalkoxy, and haloalkyl;
- $R_4$ is $N(R_{4a})_2$, wherein each $R_{4a}$ is independently selected from hydrogen, $C_{1-4}$alkyl, and $C_{1-4}$haloalkyl;
- or $R_3$ and $R_4$ together with the atoms to which they are attached form a 5- or 6-membered heteroaryl or heteroalkyl ring, optionally substituted with one to three $R_7$ groups;
- each $R_5$ and $R_6$ is independently selected from $C_{1-4}$alkyl, $C_{1-4}$haloalkyl, $C_{1-4}$alkoxy, $C_{1-4}$haloalkoxy, $C_{1-4}$alkylthio, $C_{1-4}$haloalkylthio, aryl, heteroaryl, $C_{3-7}$cycloalkyl, $C_{3-7}$heterocycloalkyl, (aryl)$C_{1-4}$alkyl, (heteroaryl)$C_{1-4}$alkyl, ($C_{3-7}$cycloalkyl)$C_{1-4}$alkyl, ($C_{3-7}$heterocycloalkyl)$C_{1-4}$alkyl, (ethenyl)$C_{1-4}$alkyl, (ethynyl)$C_{1-4}$alkyl, (aryl)$C_{1-4}$alkoxy, (heteroaryl)$C_{1-4}$alkoxy, ($C_{3-7}$cycloalkyl)$C_{1-4}$alkoxy, ($C_{3-7}$heterocycloalkyl)$C_{1-4}$alkoxy, (aryl)$C_{1-4}$alkylthio, (heteroaryl)$C_{1-4}$alkylthio, ($C_{3-7}$cycloalkyl)$C_{1-4}$alkylthio, ($C_{3-7}$heterocycloalkyl)$C_{1-4}$alkylthio, amino, halo, hydroxy, cyano, and oxo; and
- each $R_7$ is independently selected from $C_{1-4}$alkyl, $C_{1-4}$haloalkyl, $C_{1-4}$alkoxy, $C_{1-4}$haloalkoxy, aryl, heteroaryl, $C_{3-7}$cycloalkyl, $C_{3-7}$heterocycloalkyl, (aryl)$C_{1-4}$alkyl, (heteroaryl)$C_{1-4}$alkyl, ($C_{3-7}$cycloalkyl)$C_{1-4}$alkyl, ($C_{3-7}$heterocycloalkyl)$C_{1-4}$alkyl, halo, hydroxy, cyano, and oxo.

Certain compounds disclosed herein possess useful DLK inhibiting activity, and may be used in the treatment or prophylaxis of a disease in which DLK plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting DLK. Other embodiments provide methods for treating a DLK-mediated disorder in a patient in need of such treatment, comprising administering to said patient a therapeutically effective amount of a compound or composition as disclosed herein. Also provided is the use of certain compounds disclosed herein for use in the manufacture of a medicament for the treatment of a disease ameliorated by the inhibition of DLK.

In certain embodiments, $X_1$ is C and $X_2$ is N.
In certain embodiments, $X_1$ is N and $X_2$ is C.
In certain embodiments, $R_1$ is methyl, and is optionally substituted with one or two $R_5$ groups.
In certain embodiments, $R_1$ is hydroxymethyl and is optionally substituted with one $R_5$ group.
In certain embodiments, $R_2$ is H.
In certain embodiments, $R_2$ is selected from alkyl, cycloalkyl, heteroalkyl, and heterocycloalkyl, any of which is optionally substituted with one or two $R_6$ groups.
In certain embodiments, $R_2$ is selected from morpholin-1-yl, piperidin-1-yl, and piperazin-1-yl, any of which is optionally substituted with one or two $R_6$ groups.
In certain embodiments, $R_2$ is morpholin-1-yl.
In certain embodiments, $R_2$ is selected from piperazin-1-yl and 4-methylpiperazin-1-yl.
In certain embodiments, $R_2$ is H.
In certain embodiments, $R_3$ is selected from haloalkoxy and haloakyl.
In certain embodiments, $R_3$ is selected from halomethoxy and halomethyl.
In certain embodiments, $R_3$ is selected from perhalomethoxy and perhalomethyl.
In certain embodiments, $R_3$ is selected from difluoromethoxy, trifluoromethoxy, difluoromethy, and trifluoromethyl.

In certain embodiments, $R_3$ is selected from $CF_3$ and $OCF_3$.

In certain embodiments, $R_4$ is $NH_2$.

In certain embodiments, $R_4$ is selected from $NHCH_3$ and $N(CH_3)_2$.

In certain embodiments, $R_4$ is selected from NH($C_{1-4}$alkyl) and $N(C_{1-4}alkyl)_2$.

In certain embodiments, $R_3$ and $R_4$ together with the atoms to which they are attached form a 5- or 6-membered heteroaryl or heteroalkyl ring, optionally substituted with one to three $R_7$ groups.

In certain embodiments, $R_3$ and $R_4$ together with the atoms to which they are attached form a 5- or 6-membered heteroaryl or heteroalkyl ring.

In certain embodiments, $R_3$ and $R_4$ together with the atoms to which they are attached form a 5-membered heteroaryl ring, optionally substituted with one or two $R_7$ groups.

In certain embodiments, $R_5$ is selected from $C_{1-4}$alkyl, $C_{1-4}$haloalkyl, $C_{3-7}$cycloalkyl, and $C_{3-7}$heterocycloalkyl.

In certain embodiments, $R_5$ is selected from $C_{1-4}$alkoxy, $C_{1-4}$alkyl, $C_{3-7}$heterocycloalkoxy, and $C_{3-7}$cycloalkyl.

In certain embodiments, $R_5$ is selected from methyl, ethyl, trifluoromethyl, 2-propyl, and cyclopropyl.

In certain embodiments, $R_6$ is selected from $C_{1-4}$alkoxy, $C_{1-4}$alkyl, $C_{3-7}$heterocycloalkoxy, and $C_{3-7}$cycloalkyl.

In certain embodiments, $R_6$ is $C_{1-4}$alkyl.

In certain embodiments, $R_6$ is $C_{1-4}$haloalkyl.

In certain embodiments, $R_6$ is $C_{1-4}$fluoroalkyl.

In certain embodiments, $R_6$ is methyl.

In certain embodiments, $R_6$ is selected from (ethenyl)$C_{1-4}$alkyl and (ethynyl)$C_{1-4}$alkyl.

In certain embodiments, $R_6$ is selected from (ethenyl)methyl and (ethynyl)methyl.

In certain embodiments, compounds have structural formula II:

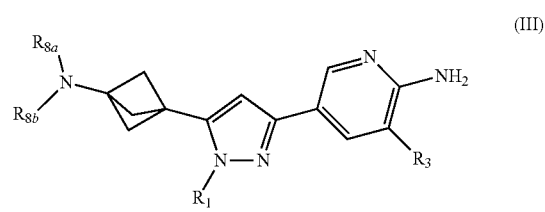

(II)

or a salt thereof, wherein:
- $R_1$ is selected from alkyl, cycloalkyl, and heterocycloalkyl, any of which is optionally substituted with one to three $R_5$ groups;
- $R_3$ is selected from H, alkyl, cyano, cycloalkyl, halo, haloalkoxy, and haloalkyl;
- $R_{8a}$ and $R_{8b}$ are independently selected from $C_{1-4}$alkyl, $C_{1-4}$haloalkyl, ($C_{1-4}$alkoxy)$C_{1-4}$alkyl, ($C_{1-4}$haloalkoxy)$C_{1-4}$alkyl, ($C_{1-4}$alkoxy)$C_{1-4}$haloalkyl, and ($C_{1-4}$haloalkoxy)$C_{1-4}$halolkyl,
- or $R_{8a}$ and $R_{8b}$, in combination with the intervening atoms, form a 4-7 membered heterocycloalkyl ring, which is optionally substituted with one to three $R_6$ groups; and
- each $R_5$ and $R_6$ is independently selected from $C_{1-4}$alkyl, $C_{1-4}$haloalkyl, $C_{1-4}$alkoxy, $C_{1-4}$haloalkoxy, $C_{1-4}$alkylthio, $C_{1-4}$haloalkylthio, aryl, heteroaryl, $C_{3-7}$cycloalkyl, $C_{3-7}$heterocycloalkyl, (aryl)$C_{1-4}$alkyl, (heteroaryl)$C_{1-4}$alkyl, (ethenyl)$C_{1-4}$alkyl, (ethynyl)$C_{1-4}$alkyl, (aryl)$C_{1-4}$alkoxy, (heteroaryl)$C_{1-4}$alkoxy, (aryl)$C_{1-4}$alkylthio, (heteroaryl)$C_{1-4}$alkylthio, amino, halo, hydroxy, cyano, and oxo.

In certain embodiments, compounds have structural formula II, depicted above, or a salt thereof, wherein:
- $R_1$ is selected from cyclopropyl, cyclopropylmethyl and isopropyl;
- $R_3$ is selected from difluoromethoxy, trifluoromethoxy, and trifluoromethyl;
- $R_{8a}$ and $R_{8b}$, in combination with the intervening atoms, form a morpholine or piperazine ring, either of which is optionally substituted with one to three $R_6$ groups; and
- $R_6$ is selected from $C_{1-4}$alkoxy, $C_{1-4}$alkyl, amino, $C_{3-6}$cycloalkyl, heterocycloalkyl, hydroxy, and hydroxyalkyl.

In certain embodiments, compounds have structural formula III:

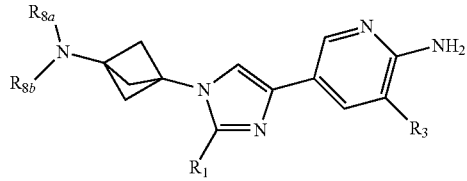

(III)

or a salt thereof, wherein:
- $R_1$ is selected from alkyl, cycloalkyl, and heterocycloalkyl, any of which is optionally substituted with one to three $R_5$ groups;
- $R_3$ is selected from H, alkyl, cyano, cycloalkyl, halo, haloalkoxy, and haloalkyl;
- $R_{8a}$ and $R_{8b}$ are independently selected from $C_{1-4}$alkyl, $C_{1-4}$haloalkyl, ($C_{1-4}$alkoxy)$C_{1-4}$alkyl, ($C_{1-4}$haloalkoxy)$C_{1-4}$alkyl, ($C_{1-4}$alkoxy)$C_{1-4}$haloalkyl, and ($C_{1-4}$haloalkoxy)$C_{1-4}$halolkyl,
- or $R_{8a}$ and $R_{8b}$, in combination with the intervening atoms, form a 4-7 membered heterocycloalkyl ring, which is optionally substituted with one to three $R_6$ groups; and
- each $R_5$ and $R_6$ is independently selected from $C_{1-4}$alkyl, $C_{1-4}$haloalkyl, $C_{1-4}$alkoxy, $C_{1-4}$haloalkoxy, $C_{1-4}$alkylthio, $C_{1-4}$haloalkylthio, aryl, heteroaryl, $C_{3-7}$cycloalkyl, $C_{3-7}$heterocycloalkyl, (aryl)$C_{1-4}$alkyl, (heteroaryl)$C_{1-4}$alkyl, (ethenyl)$C_{1-4}$alkyl, (ethynyl)$C_{1-4}$alkyl, (aryl)$C_{1-4}$alkoxy, (heteroaryl)$C_{1-4}$alkoxy, (aryl)$C_{1-4}$alkylthio, (heteroaryl)$C_{1-4}$alkylthio, amino, halo, hydroxy, cyano, and oxo.

In certain embodiments, compounds have structural formula III, depicted above, or a salt thereof, wherein:
- $R_1$ is selected from cyclopropyl, cyclopropylmethyl and isopropyl;
- $R_3$ is selected from difluoromethoxy, trifluoromethoxy, and trifluoromethyl;
- $R_{8a}$ and $R_{8b}$, in combination with the intervening atoms, form a morpholine or piperazine ring, either of which is optionally substituted with one to three $R_6$ groups; and;
- $R_6$ is selected from $C_{1-4}$alkoxy, $C_{1-4}$alkyl, amino, $C_{3-6}$cycloalkyl, heterocycloalkyl, hydroxy, and hydroxyalkyl.

In certain embodiments, compounds have structural formula IV:

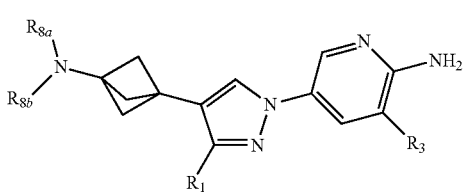

(IV)

or a salt thereof, wherein:
- $R_1$ is selected from alkyl, cycloalkyl, and heterocycloalkyl, any of which is optionally substituted with one to three $R_5$ groups;
- $R_3$ is selected from H, alkyl, cyano, cycloalkyl, halo, haloalkoxy, and haloalkyl;
- $R_{8a}$ and $R_{8b}$ are independently selected from $C_{1-4}$alkyl, $C_{1-4}$haloalkyl, $(C_{1-4}$alkoxy$)C_{1-4}$alkyl, $(C_{1-4}$haloalkoxy$)C_{1-4}$alkyl, $(C_{1-4}$alkoxy$)C_{1-4}$haloalkyl, and $(C_{1-4}$haloalkoxy$)C_{1-4}$halolkyl,
- or $R_{8a}$ and $R_{8b}$, in combination with the intervening atoms, form a 4-7 membered heterocycloalkyl ring, which is optionally substituted with one to three $R_6$ groups; and
- each $R_5$ and $R_6$ is independently selected from $C_{1-4}$alkyl, $C_{1-4}$haloalkyl, $C_{1-4}$alkoxy, $C_{1-4}$haloalkoxy, $C_{1-4}$alkylthio, $C_{1-4}$haloalkylthio, aryl, heteroaryl, $C_{3-7}$cycloalkyl, $C_{3-7}$heterocycloalkyl, (aryl)$C_{1-4}$alkyl, (heteroaryl)$C_{1-4}$alkyl, (ethenyl)$C_{1-4}$alkyl, (ethynyl)$C_{1-4}$alkyl, (aryl)$C_{1-4}$alkoxy, (heteroaryl)$C_{1-4}$alkoxy, (aryl)$C_{1-4}$alkylthio, (heteroaryl)$C_{1-4}$alkylthio, amino, halo, hydroxy, cyano, and oxo.

In certain embodiments of any of Formulas I-IV, $R_1$ is selected from cyclopropyl, cyclopropylmethyl and isopropyl.

In certain embodiments of any of Formulas I-IV, $R_{8a}$ and $R_{8b}$, in combination with the intervening atoms, form morpholinyl or piperidinyl, either of which is optionally substituted with one to three $R_6$ groups.

In certain embodiments of any of Formulas I-IV, $R_3$ is selected from difluoromethoxy, trifluoromethoxy, and trifluoromethyl.

In certain embodiments of any of Formulas I-IV, $R_5$ is selected from $C_{1-4}$alkoxy, $C_{1-4}$alkyl, amino, $C_{3-6}$cycloalkyl, heterocycloalkyl, hydroxy, and hydroxyalkyl.

In certain embodiments of any of Formulas I-IV, $R_6$ is selected from $C_{1-4}$alkoxy, $C_{1-4}$alkyl, amino, $C_{3-6}$cycloalkyl, heterocycloalkyl, hydroxy, and hydroxyalkyl.

In certain embodiments of any of Formulas I-IV, $R_6$ is $C_{1-4}$alkyl.

In certain embodiments of any of Formulas I-IV, $R_6$ is methyl.

In certain embodiments, compounds have structural formula Va:

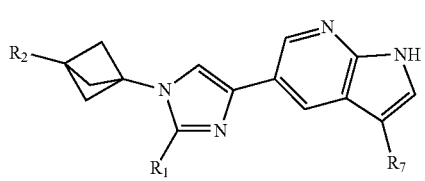

(Va)

or a salt thereof, wherein:
- $R_1$ is selected from alkyl, cycloalkyl, and heterocycloalkyl, any of which is optionally substituted with one to three $R_5$ groups;
- $R_2$ is H or is selected from alkyl, amino, aryl, cycloalkyl, haloalkyl, heteroalkyl, heteroaryl, heterocycloalkyl, and sulfonylalkyl, any of which is optionally substituted with one to three $R_6$ groups;
- each $R_5$ and $R_6$ is independently selected from $C_{1-4}$alkyl, $C_{1-4}$haloalkyl, $C_{1-4}$alkoxy, $C_{1-4}$haloalkoxy, aryl, heteroaryl, $C_{3-7}$cycloalkyl, $C_{3-7}$heterocycloalkyl, (aryl)$C_{1-4}$alkyl, (heteroaryl)$C_{1-4}$alkyl, $(C_{3-7}$cycloalkyl)$C_{1-4}$alkyl, $(C_{3-7}$heterocycloalkyl)$C_{1-4}$alkyl, (ethenyl)$C_{1-4}$alkyl, (ethynyl)$C_{1-4}$alkyl, (aryl)$C_{1-4}$alkoxy, (heteroaryl)$C_{1-4}$alkoxy, $(C_{3-7}$cycloalkyl)$C_{1-4}$alkoxy, $(C_{3-7}$heterocycloalkyl)$C_{1-4}$alkoxy, (aryl)$C_{1-4}$alkylthio, (heteroaryl)$C_{1-4}$alkylthio, $(C_{3-7}$cycloalkyl)$C_{1-4}$alkylthio, $(C_{3-7}$heterocycloalkyl)$C_{1-4}$alkylthio, amino, halo, hydroxy, cyano, and oxo; and
- $R_7$ is selected from $C_{1-4}$alkyl, $C_{1-4}$haloalkyl, $C_{1-4}$alkoxy, $C_{1-4}$haloalkoxy, aryl, heteroaryl, $C_{3-7}$cycloalkyl, $C_{3-7}$heterocycloalkyl, (aryl)$C_{1-4}$alkyl, (heteroaryl)$C_{1-4}$alkyl, $(C_{3-7}$cycloalkyl)$C_{1-4}$alkyl, $(C_{3-7}$heterocycloalkyl)$C_{1-4}$alkyl, halo, hydroxy, cyano, and oxo.

In certain embodiments, compounds have structural formula Vb:

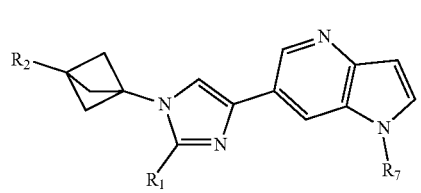

(Vb)

or a salt thereof, wherein:
- $R_1$ is selected from alkyl, cycloalkyl, and heterocycloalkyl, any of which is optionally substituted with one to three $R_5$ groups;
- $R_2$ is H or is selected from alkyl, amino, aryl, cycloalkyl, haloalkyl, heteroalkyl, heteroaryl, heterocycloalkyl, and sulfonylalkyl, any of which is optionally substituted with one to three $R_6$ groups;
- each $R_5$ and $R_6$ is independently selected from $C_{1-4}$alkyl, $C_{1-4}$haloalkyl, $C_{1-4}$alkoxy, $C_{1-4}$haloalkoxy, aryl, heteroaryl, $C_{3-7}$cycloalkyl, $C_{3-7}$heterocycloalkyl, (aryl)$C_{1-4}$alkyl, (heteroaryl)$C_{1-4}$alkyl, $(C_{3-7}$cycloalkyl)$C_{1-4}$alkyl, $(C_{3-7}$heterocycloalkyl)$C_{1-4}$alkyl, (ethenyl)$C_{1-4}$alkyl, (ethynyl)$C_{1-4}$alkyl, (aryl)$C_{1-4}$alkoxy, (heteroaryl)$C_{1-4}$alkoxy, $(C_{3-7}$cycloalkyl)$C_{1-4}$alkoxy, $(C_{3-7}$heterocycloalkyl)$C_{1-4}$alkoxy, (aryl)$C_{1-4}$alkylthio, (heteroaryl)$C_{1-4}$alkylthio, $(C_{3-7}$cycloalkyl)$C_{1-4}$alkylthio, $(C_{3-7}$heterocycloalkyl)$C_{1-4}$alkylthio, amino, halo, hydroxy, cyano, and oxo; and
- $R_7$ is selected from $C_{1-4}$alkyl, $C_{1-4}$haloalkyl, $C_{1-4}$alkoxy, $C_{1-4}$haloalkoxy, aryl, heteroaryl, $C_{3-7}$cycloalkyl, $C_{3-7}$heterocycloalkyl, (aryl)$C_{1-4}$alkyl, (heteroaryl)$C_{1-4}$alkyl, $(C_{3-7}$cycloalkyl)$C_{1-4}$alkyl, $(C_{3-7}$heterocycloalkyl)$C_{1-4}$alkyl, halo, hydroxy, cyano, and oxo.

In certain embodiments, compounds have structural formula VI:

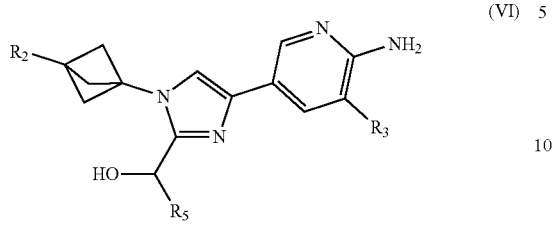

(VI)

or a salt thereof, wherein:
R₂ is H or is selected from alkyl, amino, aryl, cycloalkyl, haloalkyl, heteroalkyl, heteroaryl, heterocycloalkyl, and sulfonylalkyl, any of which is optionally substituted with one to two R₆ groups;
R₃ is selected from haloalkoxy and haloalkyl; and
R₅ is selected from $C_{1-4}$alkyl, $C_{1-4}$haloalkyl, and $C_{3-7}$cycloalkyl.
each R₆ is independently selected from $C_{1-4}$alkyl, $C_{1-4}$haloalkyl, (ethenyl)$C_{1-4}$alkyl, (ethynyl)$C_{1-4}$alkyl, amino, halo, hydroxy, cyano, and oxo.

In certain embodiments of Formula VI, R₂ is H.

In certain embodiments of Formula VI, R₂ is heterocycloalkyl.

In certain embodiments of Formula VI, R₂ is selected from morpholin-1-yl, piperidin-1-yl, and piperazin-1-yl, any of which is optionally substituted with one or two R₆ groups.

In certain embodiments of Formula VI, R₂ is selected from

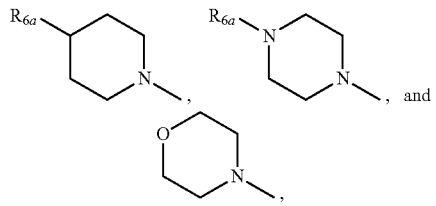

and $R_{6a}$ is selected from H, $C_{1-4}$alkyl, $C_{1-4}$haloalkyl, (ethenyl)$C_{1-4}$alkyl, and (ethynyl)$C_{1-4}$alkyl.

In certain embodiments of Formula VI, R₃ is selected from difluoromethoxy, trifluoromethoxy, and trifluoromethyl.

In certain embodiments of Formula VI, R₅ is selected from $C_{1-4}$alkyl and $C_{1-4}$haloalkyl.

In certain embodiments of Formula VI, R₅ is selected from methyl and trifluoromethyl.

In certain embodiments, compounds are selected from

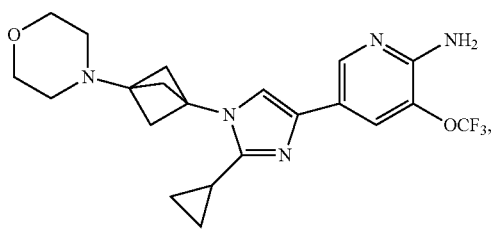

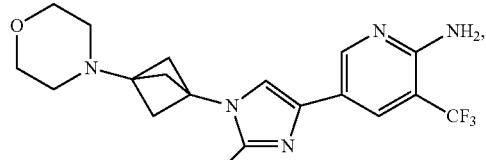

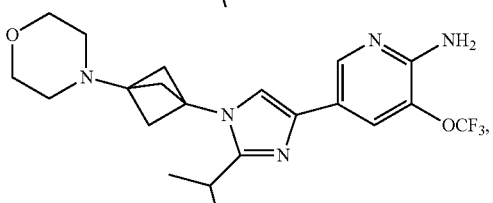

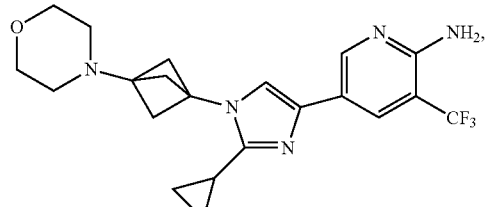

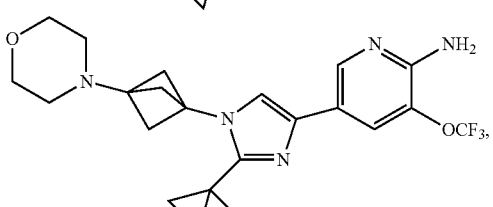

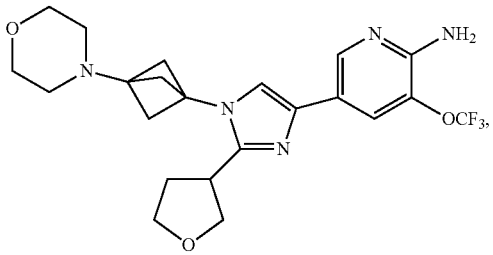

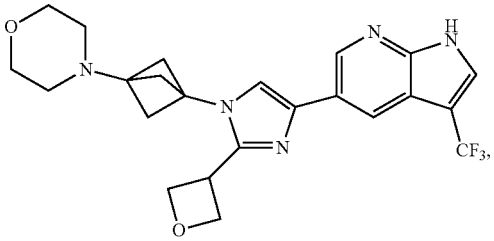

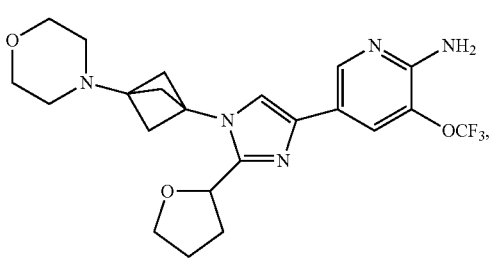

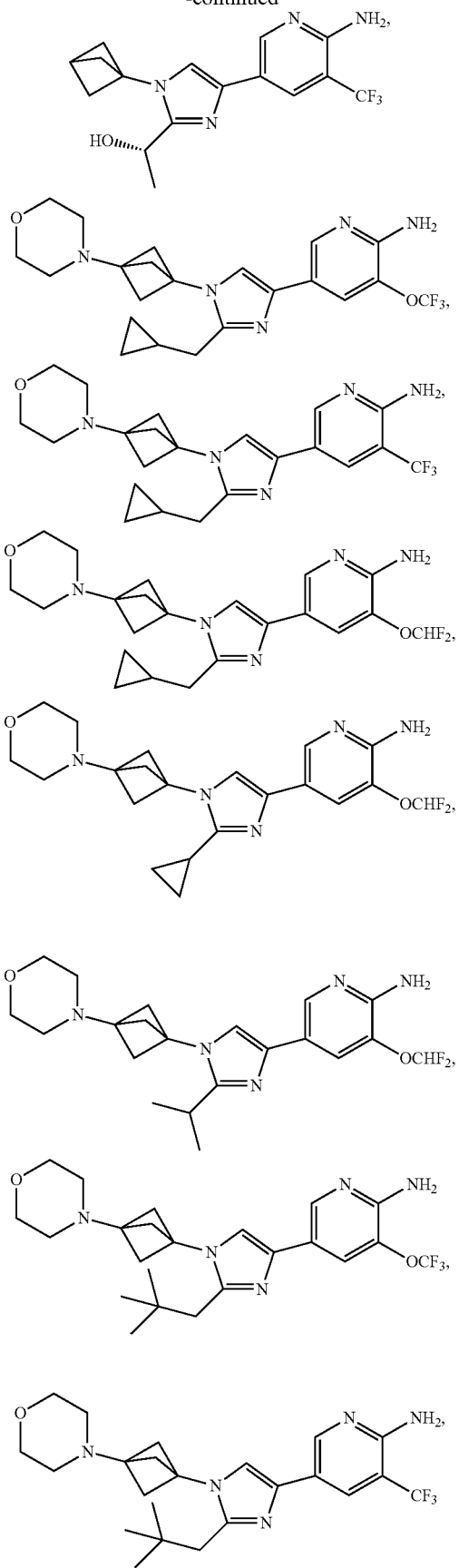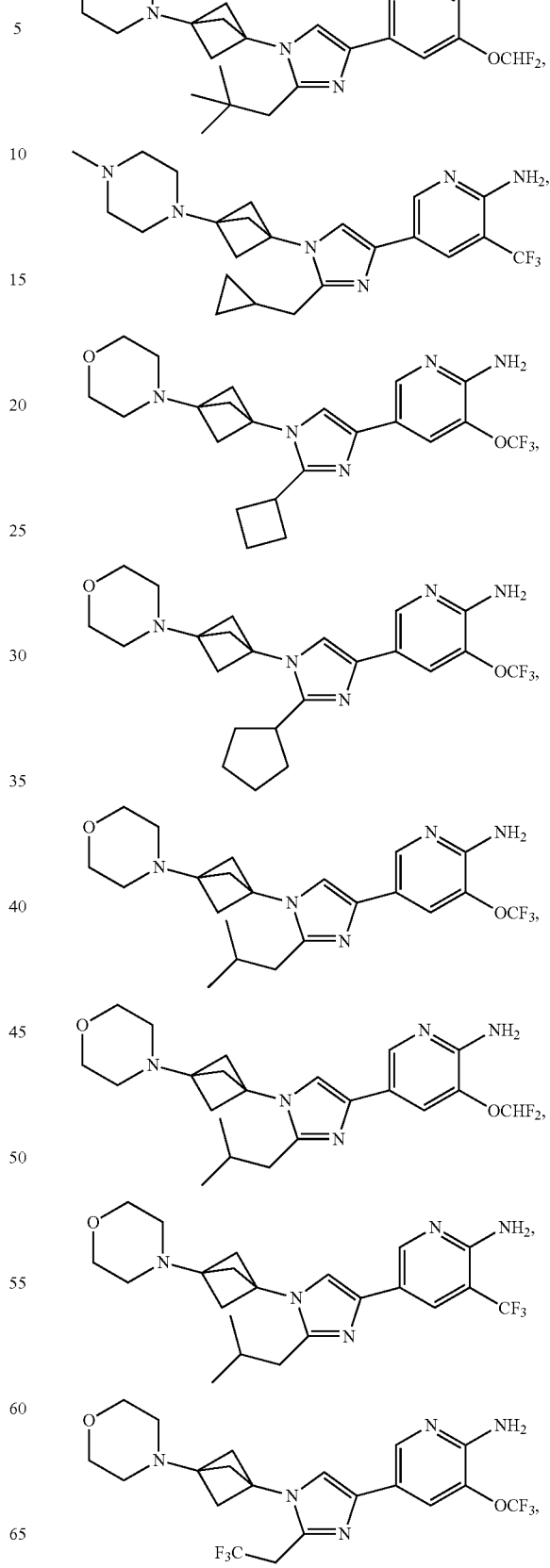

-continued
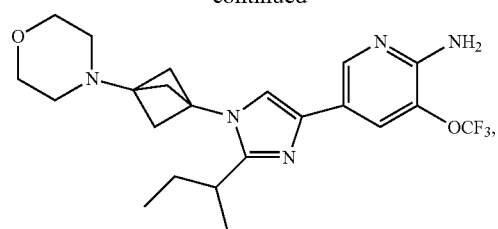
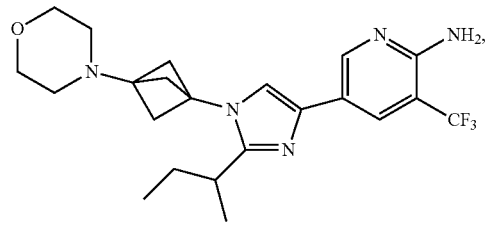
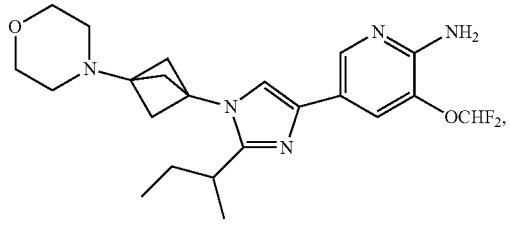
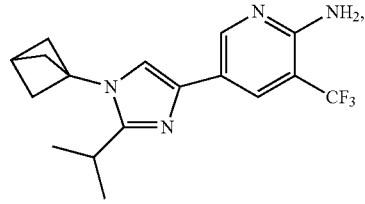
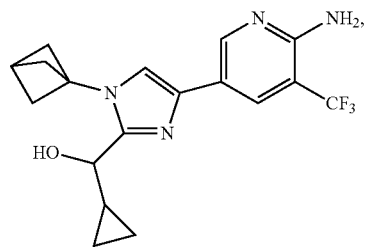
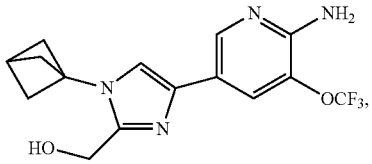
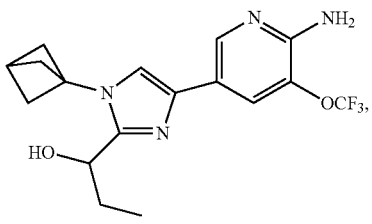
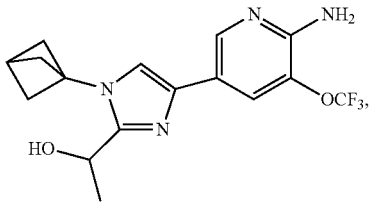
-continued
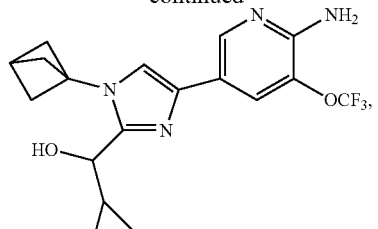
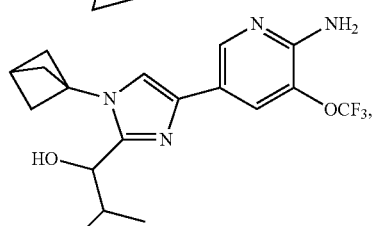
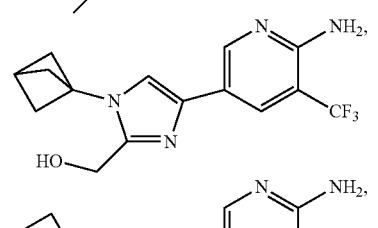
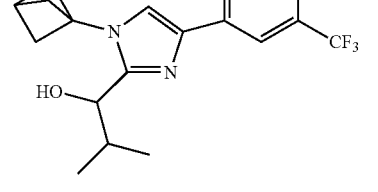
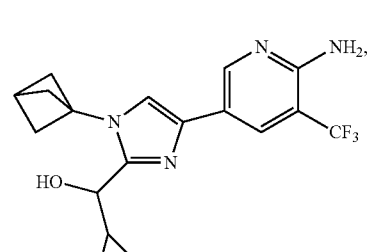
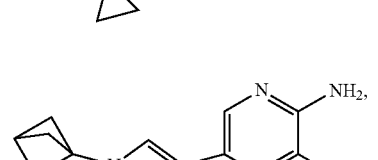
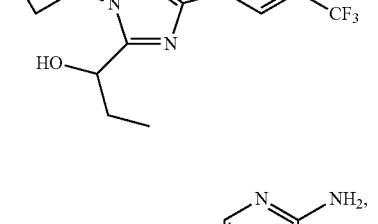
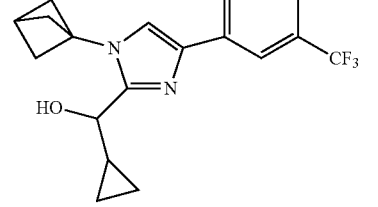

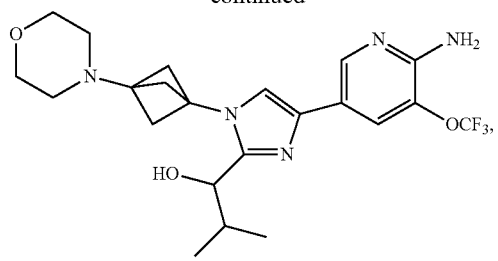
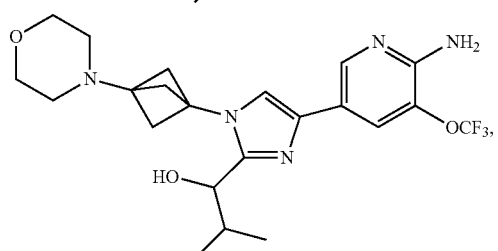
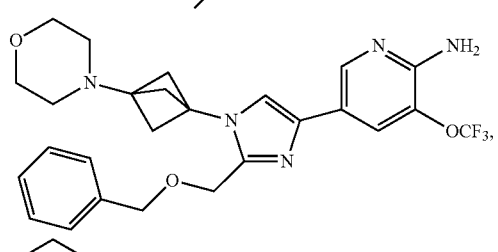
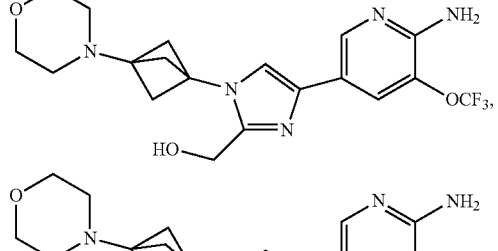
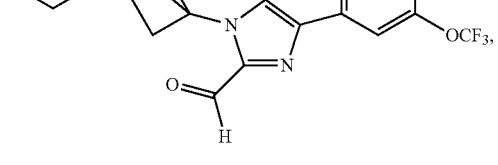
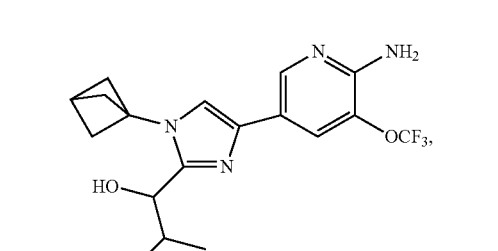
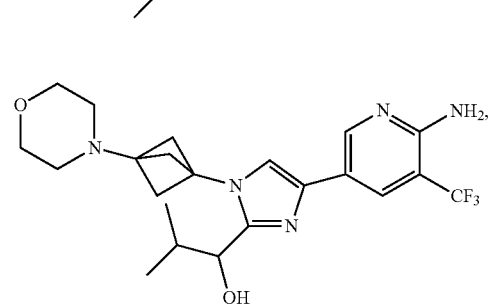
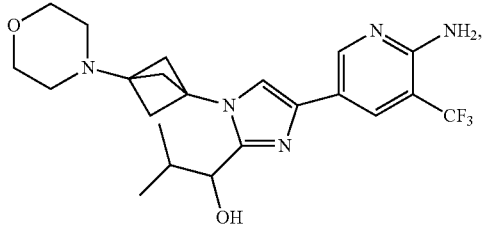
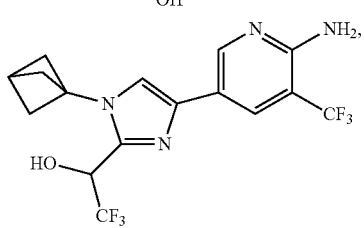
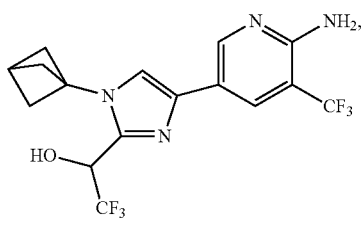
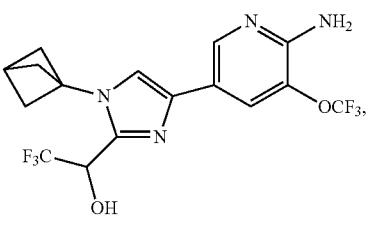
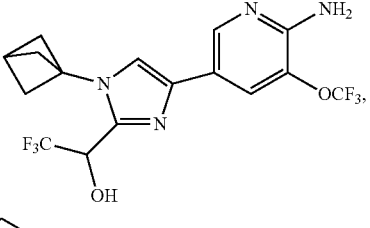
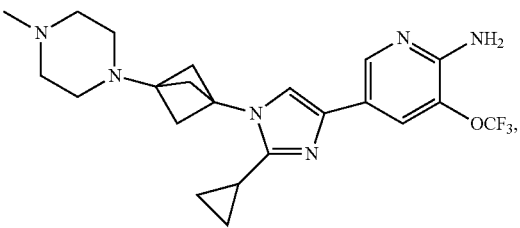
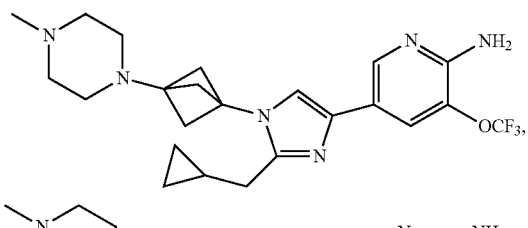
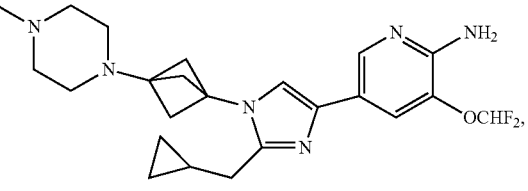

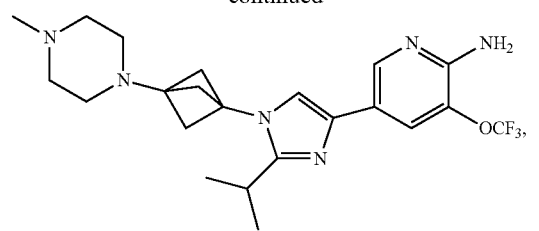
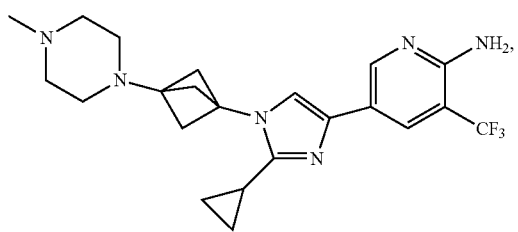
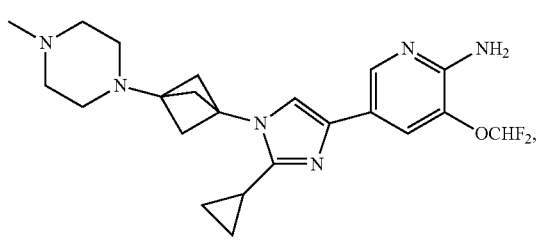
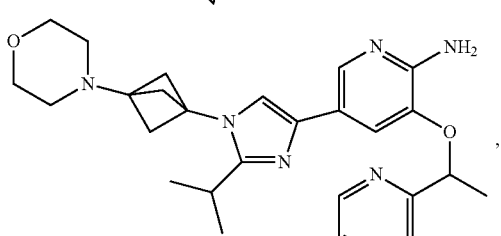
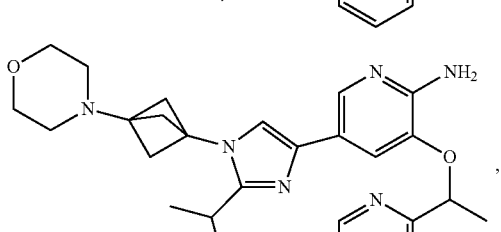
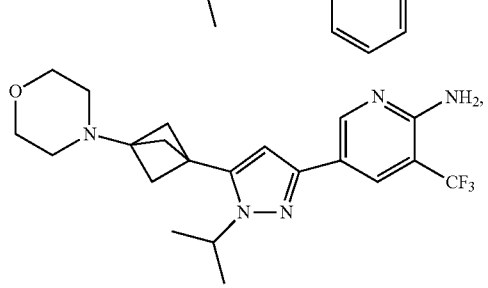
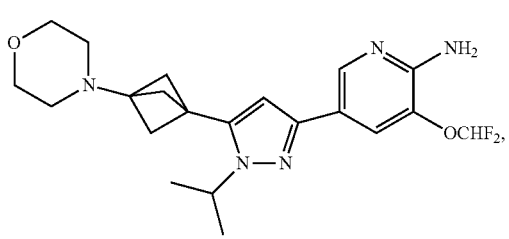
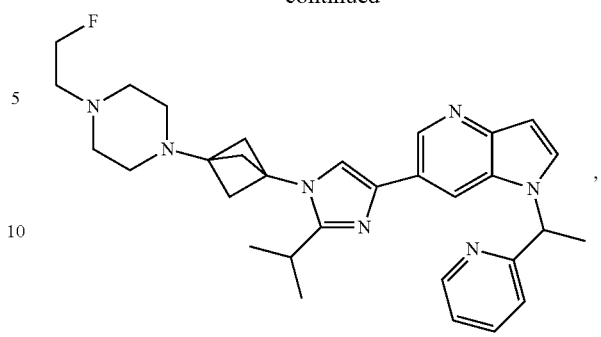
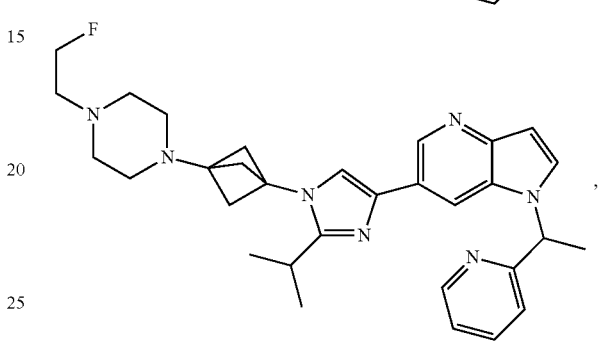
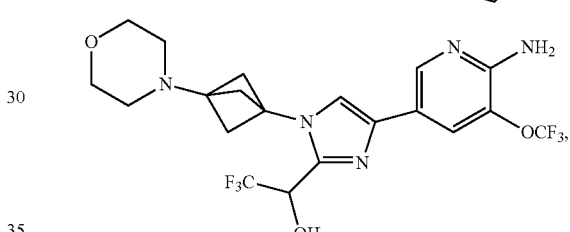
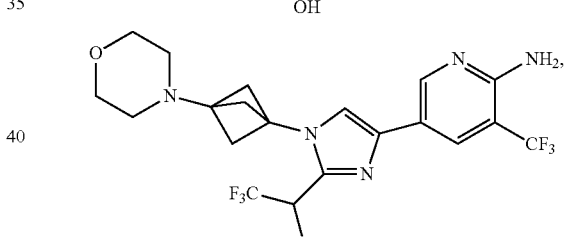
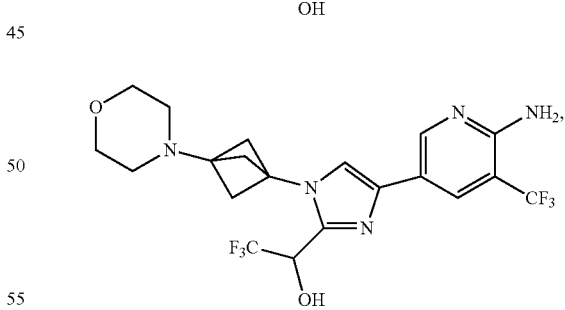
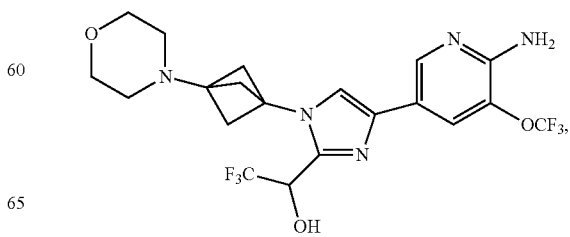

-continued
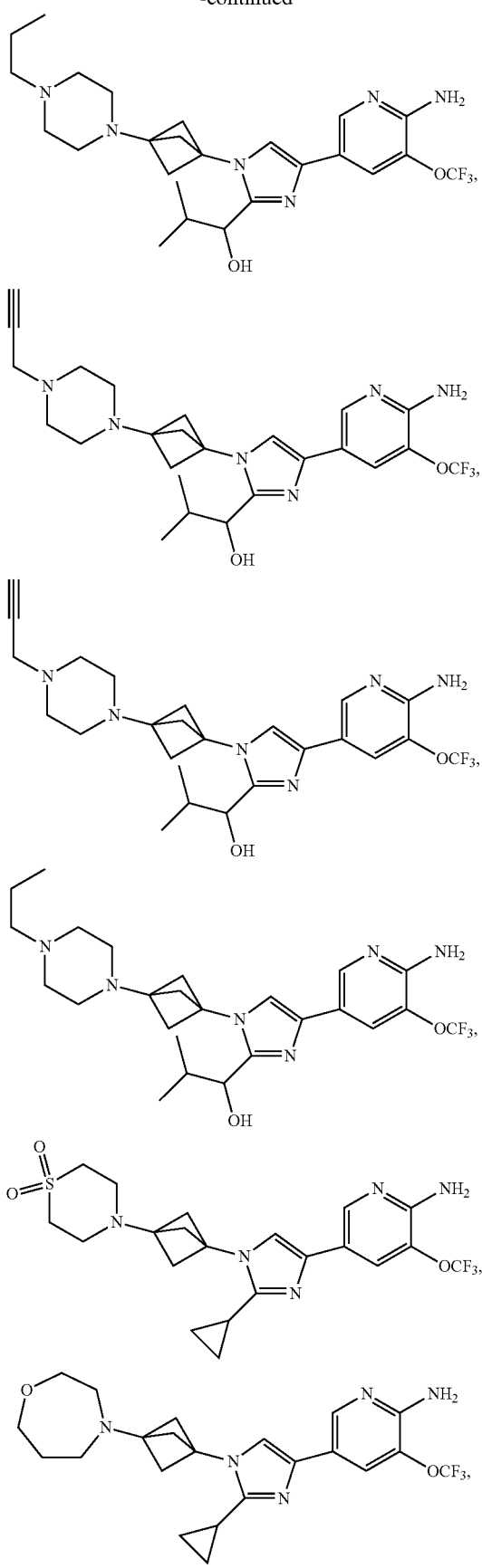
-continued
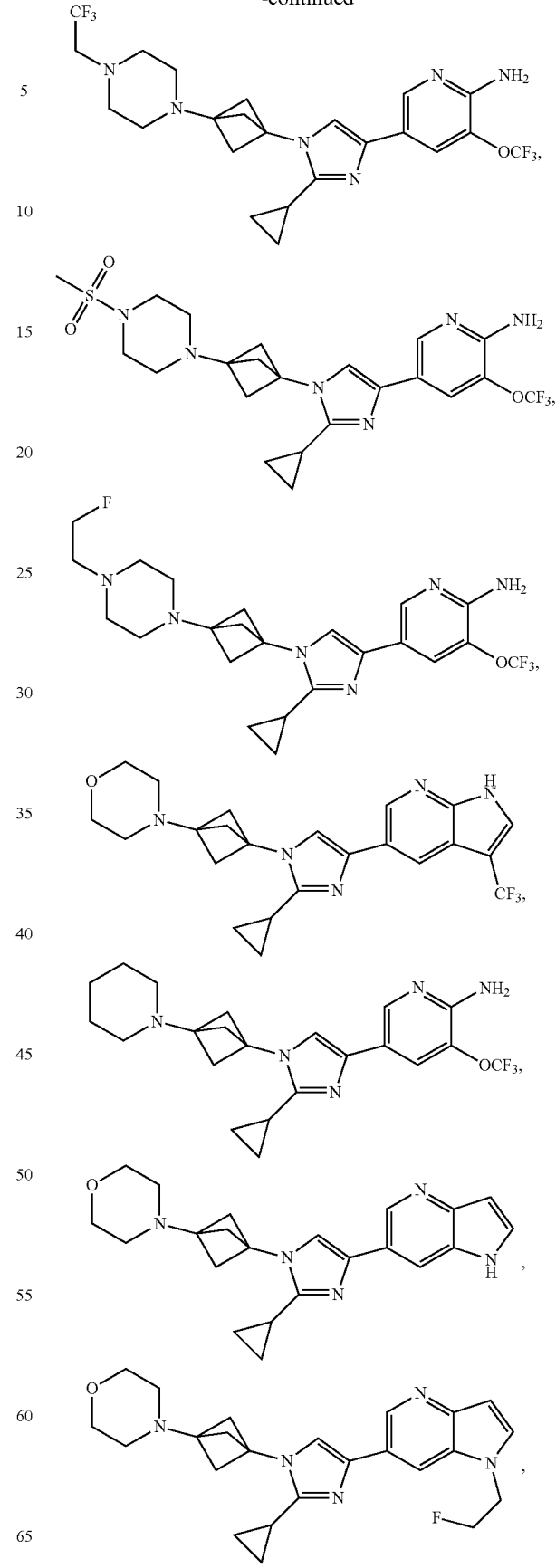

-continued

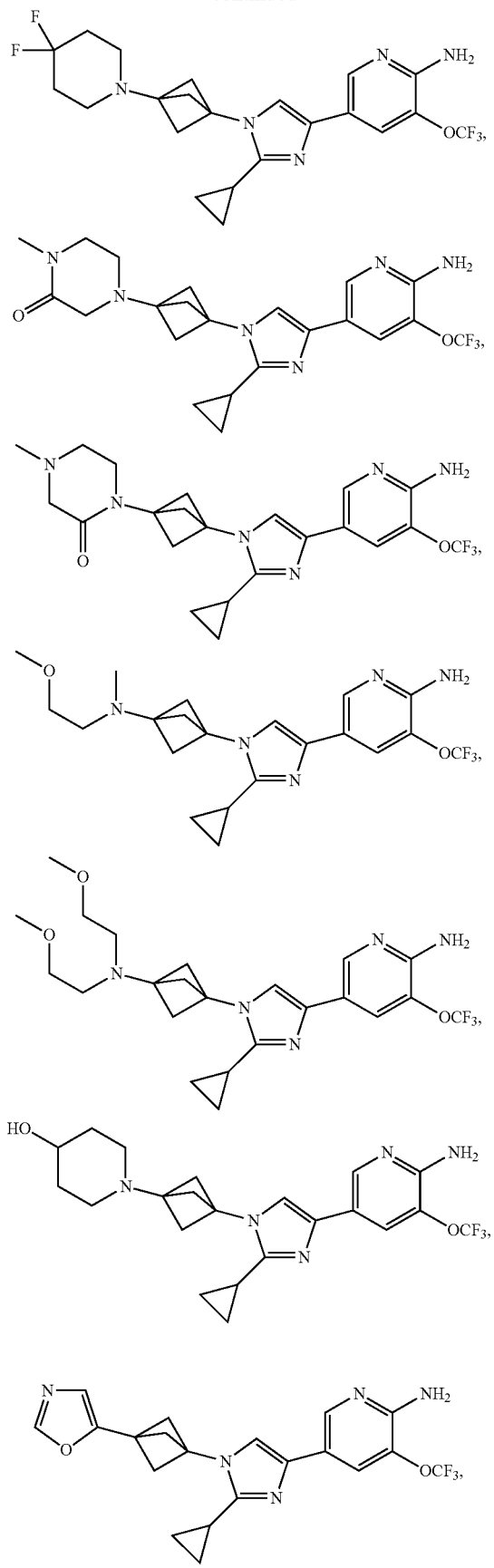

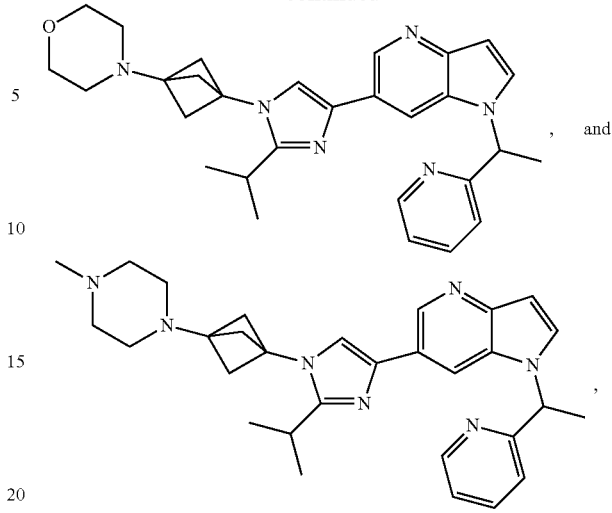

or a salt thereof.

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

Also provided is a compound chosen from the Examples disclosed herein.

Also provided are methods of inhibiting at least one DLK function comprising the step of contacting DLK with a compound as described herein. The cell phenotype, cell proliferation, activity of DLK, change in biochemical output produced by active DLK, expression of DLK, or binding of DLK with a natural binding partner may be monitored. Such methods may be modes of treatment of disease, biological assays, cellular assays, biochemical assays, or the like.

Also provided herein are methods of treatment of a DLK-mediated disease comprising the administration of a therapeutically effective amount of a compound as disclosed herein, or a salt thereof, to a patient in need thereof.

In certain embodiments, the disease is chosen from a neurodegenerative disease.

Also provided herein is a compound as disclosed herein for use as a medicament.

Also provided herein is a compound as disclosed herein for use as a medicament for the treatment of a DLK-mediated disease.

Also provided is the use of a compound as disclosed herein as a medicament.

Also provided is the use of a compound as disclosed herein as a medicament for the treatment of a DLK-mediated disease.

Also provided is a compound as disclosed herein for use in the manufacture of a medicament for the treatment of a DLK-mediated disease.

Also provided is the use of a compound as disclosed herein for the treatment of a DLK-mediated disease.

Also provided herein is a method of inhibition of DLK comprising contacting DLK with a compound as disclosed herein, or a salt thereof.

Also provided herein is a method for achieving an effect in a patient comprising the administration of a therapeutically effective amount of a compound as disclosed herein, or a salt thereof, to a patient, wherein the effect is chosen from cognition enhancement.

In certain embodiments, the DLK-mediated disease is chosen from a disease that results from traumatic injury to central nervous system and peripheral nervous system neurons (e.g. stroke, traumatic brain injury, spinal cord injury), a disease that results from a chronic neurodegenerative condition (e.g. Alzheimer's disease, frontotemporal dementia, Parkinson's disease, Huntington's disease, amyotrophic lateral sclerosis, spinocerebellar ataxia, progressive supranuclear palsy, Lewy body disease, Kennedy's disease, and other related conditions), a disease that results from neuropathies resulting from neurological damage (chemotherapy-induced peripheral neuropathy, diabetic neuropathy, and related conditions) and a disease that results from cognitive disorders caused by pharmacological intervention (e.g. chemotherapy induced cognitive disorder, also known as chemobrain).

Also provided is a method of modulation of a DLK-mediated function in a subject comprising the administration of a therapeutically effective amount of a compound as disclosed herein.

Also provided is a pharmaceutical composition comprising a compound as disclosed herein, together with a pharmaceutically acceptable carrier.

In certain embodiments, the pharmaceutical composition is formulated for oral administration.

In certain embodiments, the oral pharmaceutical composition is chosen from a tablet and a capsule.

Definitions

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH₃ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C:C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH₂—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3C(O)NH$—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. In certain embodiments, said cycloalkyl will comprise a spirocycle ring system. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1.1.1]pentane, camphor, adamantane, and bicyclo[3.2.1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—$CF_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —$CH_2$—NH—$OCH_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently chosen from nitrogen, oxygen, and sulfur. In certain embodiments, said heterocycloalkyl will comprise a spirocycle ring system. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS— group, where R is as defined herein.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "spirocycle ring system" refers to a polycyclic ring system comprising two rings such that a single atom is common to both rings.

The terms "sulfonate," "sulfonic acid," and "sulfonic," as used herein, alone or in combination, refer the —SO₃H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)₂—.

The term "N-sulfonamido" refers to a RS(=O)₂NR'— group with R and R' as defined herein.

The term "S-sulfonamido" refers to a —S(=O)₂NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X₃CS(O)₂NR— group with X is a halogen and R as defined herein.

The term "trihalomethanesulfonyl" refers to a X₃CS(O)₂— group where X is a halogen.

The term "trihalomethoxy" refers to a X₃CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N₃, SH, SCH₃, C(O)CH₃, CO₂CH₃, CO₂H, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH₂CH₃), fully substituted (e.g., —CF₂CF₃), monosubstituted (e.g., —CH₂CH₂F) or substituted at a level anywhere in-between fully substituted and monosubstituted (e.g., —CH₂CF₃). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R″ where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N (R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

A "cognitive disorder," as used herein refers to a mental health disorder in which loss of cognitive function is the primary symptom, and which primarily affects learning, memory, perception, and/or problem solving. Cognitive disorders include amnesia, dementia, and delirium. Causes may include damage to the memory portions of the brain, whether from trauma or chemotherapy.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"DLK binder" is used herein to refer to a compound that exhibits an $K_d$ with respect to DLK of no more than about 100 µM and more typically not more than about 50 µM, as measured in the DLK binding assay described generally herein. The DLK binding assay measures the $K_d$ (dissociation constant) for the binding of a compound with the active site of DLK. Certain compounds disclosed herein have been discovered to bind to DLK. In certain embodiments, compounds will exhibit an $K_d$ with respect to DLK of no more than about 10 µM; in further embodiments, compounds will exhibit a $K_d$ with respect to DLK of no more than about 1 µM; in yet further embodiments, compounds will exhibit a $K_d$ with respect to DLK of not more than about 0.1 µM; in yet further embodiments, compounds will exhibit a $K_d$ with respect to DLK of not more than about 10 nM, as measured in the DLK assay described herein.

The phrase "therapeutically effective" is intended to qualify the amount of active ingredients used in the treatment of a disease or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

Salts and Polymorphs

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

Formulations

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Administration and Treatment

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds of the invention with: donepezil, rivastigmine, galantamine, and memantine.

Further examples include anti-amyloid antibodies and vaccines, anti-Ab antibodies and vaccines, anti-tau antibodies and vaccines, β-secretase inhibitors, 5-HT4 agonists, 5-HT6 antagonists, 5-HT1a antagonists, α7 nicotinic receptor agonists, 5-HT3 receptor antagonists, PDE4 inhibitors, O-glycnacase inhibitors, and other medicines approved for the treatment of Alzheimer's disease. Further examples include metformin, minocycline, tissue plasminogen activator, and other therapies that improve neuronal survival.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating DLK-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein, in combination with one or more additional agents for the treatment of DLK-mediated disorders.

In certain embodiments, the compounds, compositions, and methods disclosed herein may be useful for the treatment of neurological diseases that result from traumatic injury to central nervous system and peripheral nervous system neurons.

In certain embodiments, the compounds, compositions, and methods disclosed herein may be useful for the treatment of stroke.

In certain embodiments, the compounds, compositions, and methods disclosed herein may be useful for the treatment of traumatic brain injury.

In certain embodiments, the compounds, compositions, and methods disclosed herein may be useful for the treatment of spinal cord injury.

In certain embodiments, the compounds, compositions, and methods disclosed herein may be useful for the treatment of neurologic diseases that result from a chronic neurodegenerative condition.

In certain embodiments, the neurodegenerative condition is Alzheimer's disease.

In certain embodiments, the neurodegenerative condition is frontotemporal dementia.

In certain embodiments, the neurodegenerative condition is Parkinson's disease.

In certain embodiments, the neurodegenerative condition is Huntington's disease.

In certain embodiments, the neurodegenerative condition is amyotrophic lateral sclerosis.

In certain embodiments, the neurodegenerative condition is Alzheimer's disease.

In certain embodiments, the neurodegenerative condition is spinocerebellar ataxia.

In certain embodiments, the neurodegenerative condition is progressive supranuclear palsy.

In certain embodiments, the neurodegenerative condition is Lewy body disease.

In certain embodiments, the neurodegenerative condition is Kennedy's disease.

In certain embodiments, the compounds, compositions, and methods disclosed herein may be useful for the treatment of neuropathies resulting from neural damage.

In certain embodiments, the neuropathy is chemotherapy-induced peripheral neuropathy.

In certain embodiments, the neuropathy is diabetic neuropathy.

In certain embodiments, the compounds, compositions, and methods disclosed herein may be useful for the treatment of cognitive disorders.

In certain embodiments, the cognitive disorder is caused by pharmacological intervention.

In certain embodiments, the cognitive disorder is chemotherapy induced cognitive disorder.

In certain embodiments, the compounds, compositions, and methods disclosed herein may be coadministered with another therapeutic agent.

In certain embodiments, the compounds, compositions, and methods disclosed herein may be coadministered with another therapeutic agent for the treatment of cognitive disorders.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

List of Abbreviations $Ac_2O$=acetic anhydride; AcCl=acetyl chloride; AcOH=acetic acid; AIBN=azobisisobutyronitrile; aq.=aqueous; BAST=bis(2-methoxyethyl)aminosulfur trifluoride; Bu=butyl; $Bu_3SnH$=tributyltin hydride; $CD_3OD$=deuterated methanol; $CDCl_3$=deuterated chloroform; CDI=1,1'-carbonyldiimidazole; DAST=(diethylamino)sulfur trifluoride; dba=dibenzylideneacetone DBU=1,8-diazabicyclo[5.4.0]undec-7-ene; DCM=dichloromethane; DEAD=diethyl azodicarboxylate; DIBAL-H=di-iso-butyl aluminium hydride; DIEA=DIPEA=N,N-diisopropylethylamine; DMAP=4-dimethylaminopyridine; DMF=N,N-dimethyl-formamide; $DMSO-d_6$=deuterated dimethyl sulfoxide; DMSO=dimethyl sulfoxide; DPPA=diphenylphosphoryl azide; dppf=1,1'-bis(diphenylphosphino)ferrocene; EDC.HCl=EDCI.HCl=1-ethyl-3-(3-dimethylaminopropyl)carbodiimide hydrochloride; Et=ethyl; $Et_2O$=diethyl ether; EtOAc=ethyl acetate; EtOH=ethanol; h=hour; HATU=2-(1H-7-azabenzotriazol-1-yl)-1,1,3,3-tetramethyl uronium hexafluorophosphate methanaminium; HMDS=hexamethyl-disilazane; HOBT=1-hydroxybenzotriazole; i-Pr=isopropyl=2-propyl; i-PrOH=isopropanol; LAH=lithium aluminiumhydride; LDA=lithium diisopropyl amide; LiHMDS=Lithium bis(trimethylsilyl)amide; MeCN=acetonitrile; MeI=methyl iodide; MeOH=methanol; MP-carbonate resin=macroporous triethylammonium methylpolystyrene carbonate resin; MsCl=mesyl chloride; MTBE=methyl tertiary butyl ether; n-BuLi=n-butyllithium; NaHMDS=Sodium bis(trimethylsilyl)amide; NaOEt=sodium ethoxide; NaOMe=sodium methoxide; NaOtBu=sodium t-butoxide; NBS=N-bromosuccinimide; NCS=N-chlorosuccinimide; NIS=N-iodosuccinimide; NMP=N-Methyl-2-pyrrolidone; $Pd(Ph_3)_4$=tetrakis(triphenylphosphine)-palladium(0); $Pd_2(dba)_3$=tris(dibenzylideneacetone)dipalladium(0); $PdCl_2(PPh_3)_2$=bis(triphenylphosphine)palladium(II) dichloride; PG=protecting group;

Ph=phenyl; prep-HPLC=preparative high-performance liquid chromatography; PMBCl=para-methoxybenzyl; PMBCl=para-methoxybenzyl chloride; PMBOH=para-methoxybenzyl alcohol; PyBop=(benzotriazol-1-yloxy)tripyrrolidinophosphonium hexafluorophosphate; Pyr=pyridine; RT=room temperature; RuPhos=2-dicyclohexylphosphino-2',6'-diisopropoxybiphenyl; sat.=saturated; ss=saturated solution; tBu=t-Bu=tert-butyl=1,1-dimethylethyl; TBAF=tetrabutylammonium fluoride; TBDPS=t-butyldiphenylsilyl; t-BuOH=tert-butanol; T3P=Propylphosphonic Anhydride; TEA=$Et_3N$=triethylamine; TFA=trifluoroacetic acid; TFAA=trifluoroacetic anhydride; THF=tetrahydrofuran; TIPS=triisopropylsilyl; Tol=toluene; TsCl=tosyl chloride=p-toluenesulfonyl chloride; TosMIC=p-toluenesulfonylmethyl isocyanide; Trt=trityl=(triphenyl)methyl; Xantphos=4,5-Bis(diphenylphosphino)-9,9-dimethylxanthene; XPhos=2-dicyclohexylphosphino-2',4',6'-triisopropylbiphenyl.

General Synthetic Methods for Preparing Compounds

The following schemes can be used to practice the present invention.

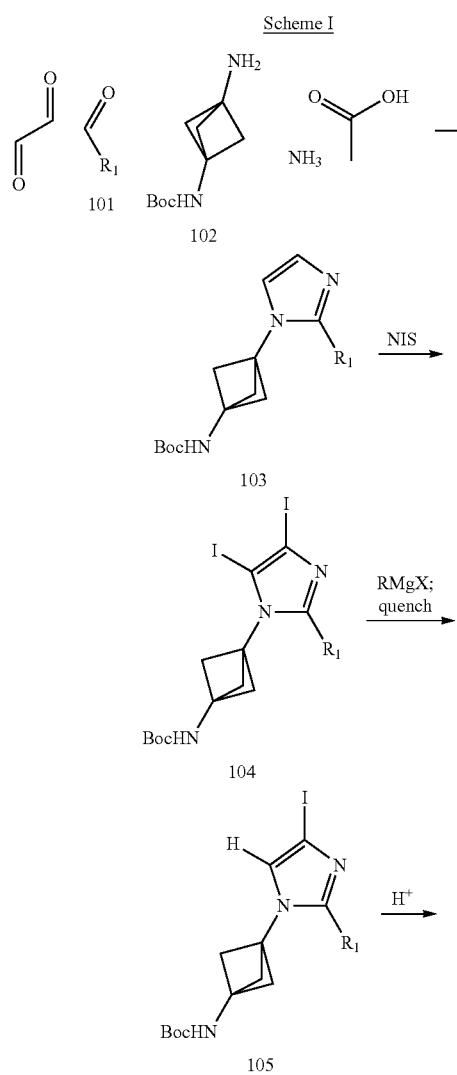

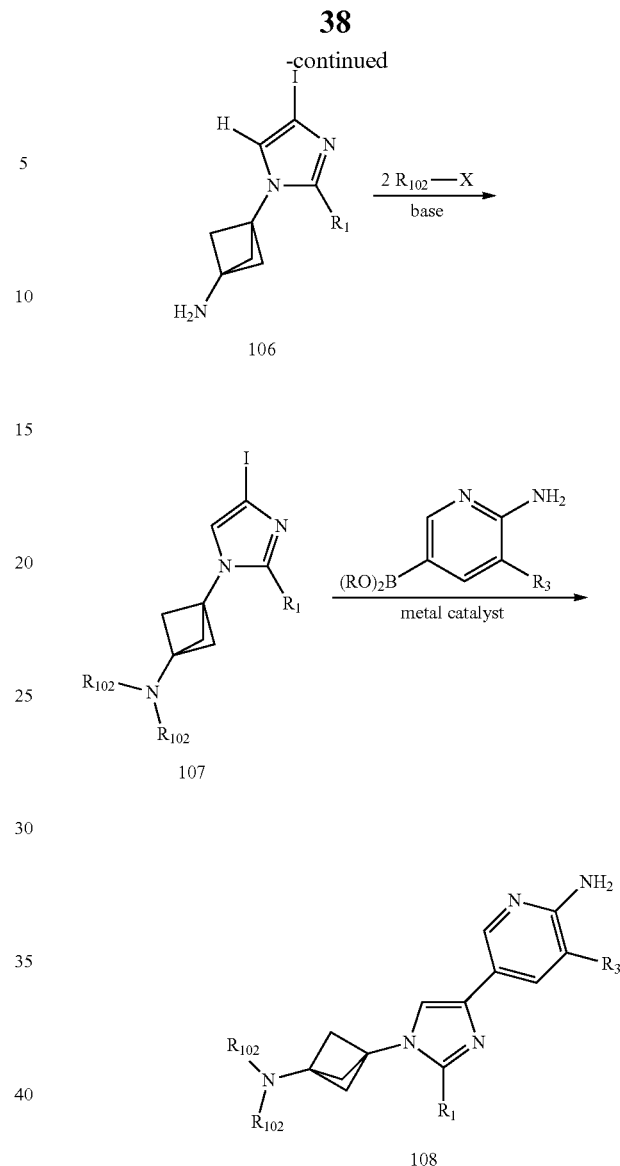

Example 1, and similar compounds, can be synthesized by using the general synthetic procedure set forth in Scheme I. Imidazole 103 is obtained from reaction of aldehyde 101, glyoxal, and amine 102. Reaction with two equivalents of NIS gives the 4,5-diiodo compound 104. Transmetalation with a Grignard reagent takes place selectively at the 5-position, and the resulting organometallic species is quenched with $H^+$ to give the 4-iodo compound 105. Removal of the t-butoxy carbonyl (Boc) protecting group gives amine 106, which is then reacted with an alkylating agent $R_{102}$—X, giving 107. Use of a difunctionalized reagent for alkylation, such as an α,ω-dihaloalkane, will provide a cyclic amine product. For example, use of 1-bromo-2-(2-bromoethoxy)ethane will provide a product with a morpholine moiety. The target compound 108 is obtained by reaction of an arylboronic ester with the iodo-imidazole using well-established coupling techniques. It is well understood by one trained in the art that many obvious modifications to the above general route can be envisioned to modify the $R_1$, $R_3$, and $R_{102}$ groups.

Scheme II

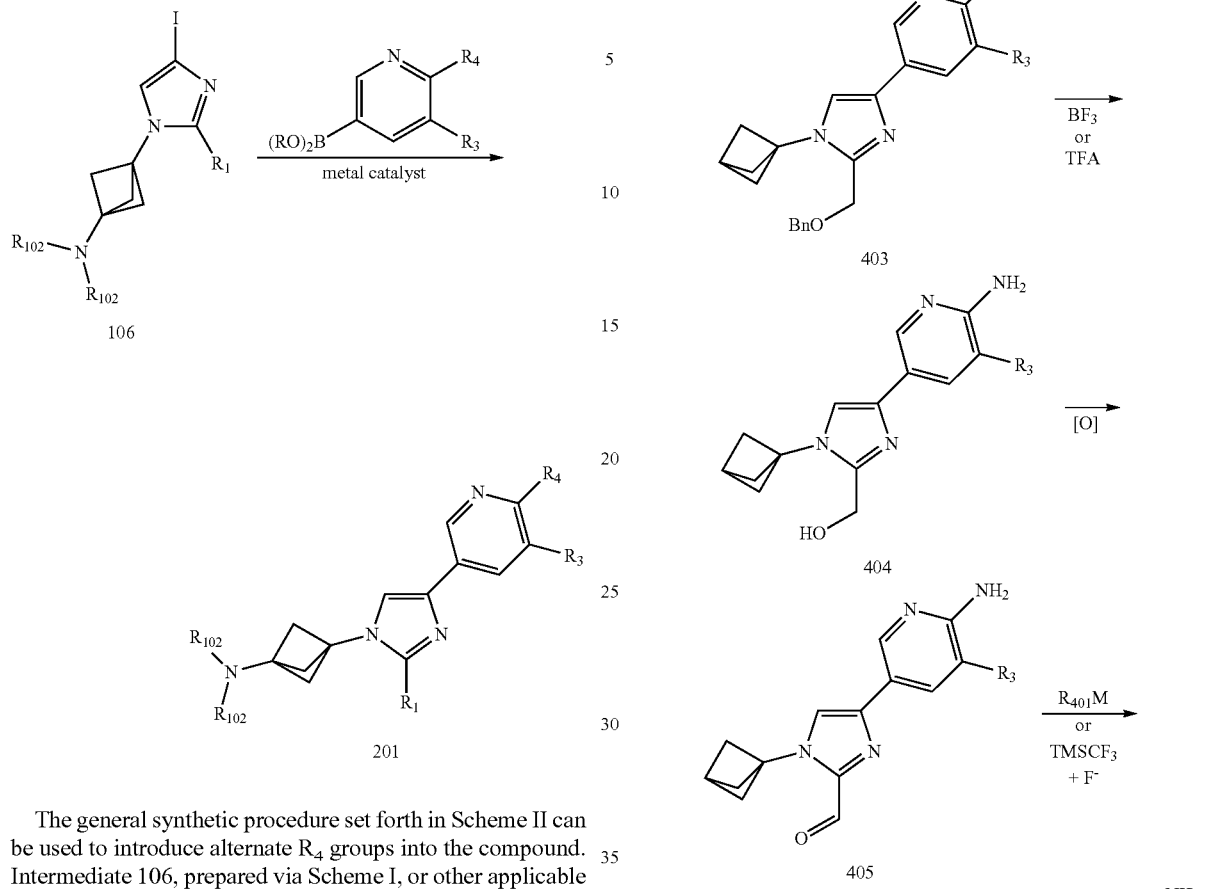

The general synthetic procedure set forth in Scheme II can be used to introduce alternate $R_4$ groups into the compound. Intermediate 106, prepared via Scheme I, or other applicable method, is reacted with an arylboronic ester using well-established coupling techniques. It is well understood by one trained in the art that many obvious modifications to the above general route can be envisioned to modify the $R_1$, $R_3$, $R_4$, and $R_{102}$ groups.

Scheme III

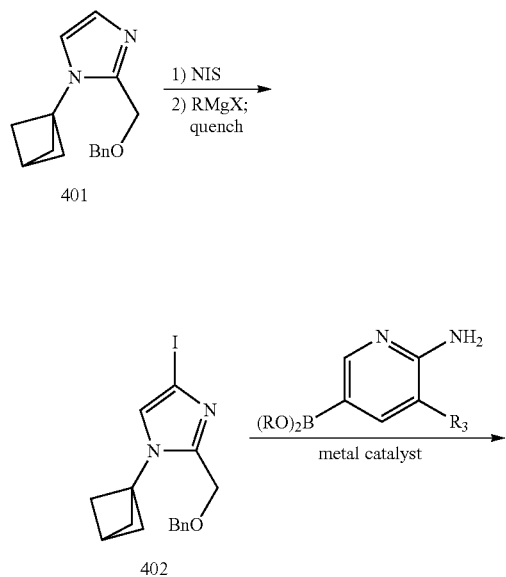

Example 5a/b, and similar compounds, can be synthesized by using the general synthetic procedure set forth in Scheme III (Bn=benzyl=PhCH$_2$—). The first step of Scheme I is performed with benzyl-protected glycolaldehyde 401 (obtained from Scheme I using $R_1$=BnOCH$_2$ and bicyclo[1.1.1]pentan-1-amine instead of amine 102) to give (benzyl)oxy compound 402. The procedure of Scheme I is continued up to the coupled (benzyl)oxy intermediate 403, which is deprotected under acidic conditions to give primary alcohol 404. The alcohol is oxidized to the corresponding aldehyde 405, then reacted with a suitable organometallic reagent to give secondary alcohol 406. Alternatively, aldehyde 405 is reacted with TMSCF$_3$ in the presence of F$^-$ to provide 406 ($R_{401}$=CF$_3$). Optionally, the enantiomers of 406 can be separated by methods known in the field (not shown), such as chromatography. It is well understood by one trained in the art that many obvious modifications to the above general route can be envisioned to modify the $R_3$ and $R_{401}$ groups.

Scheme IV

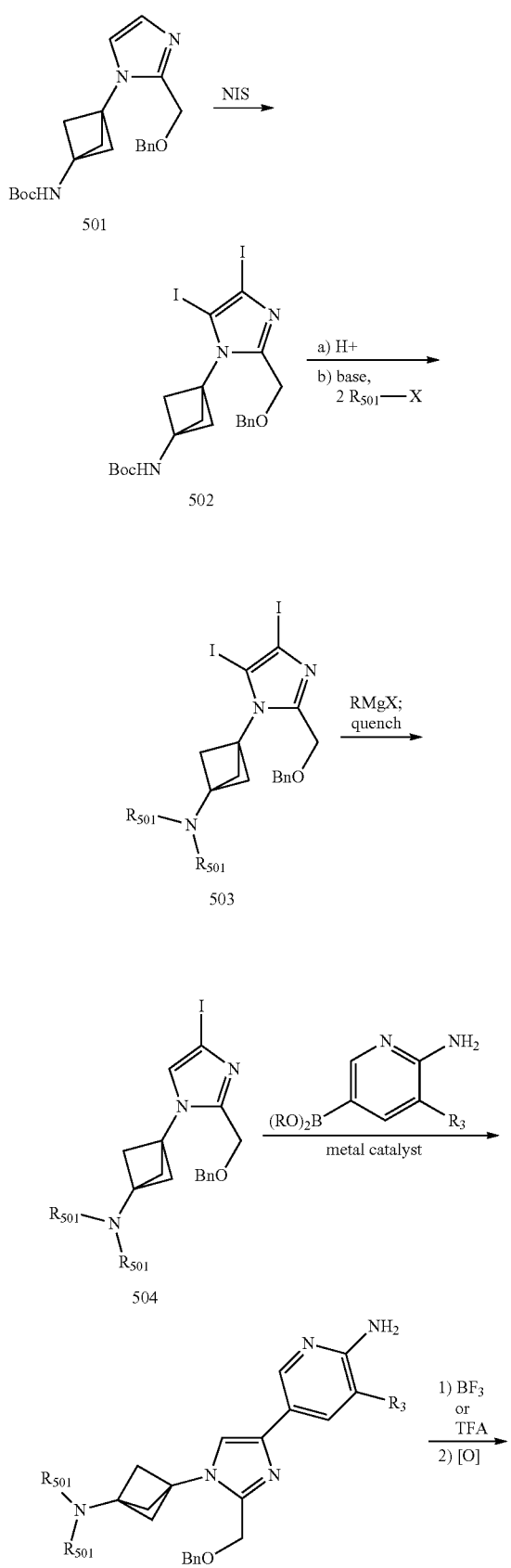

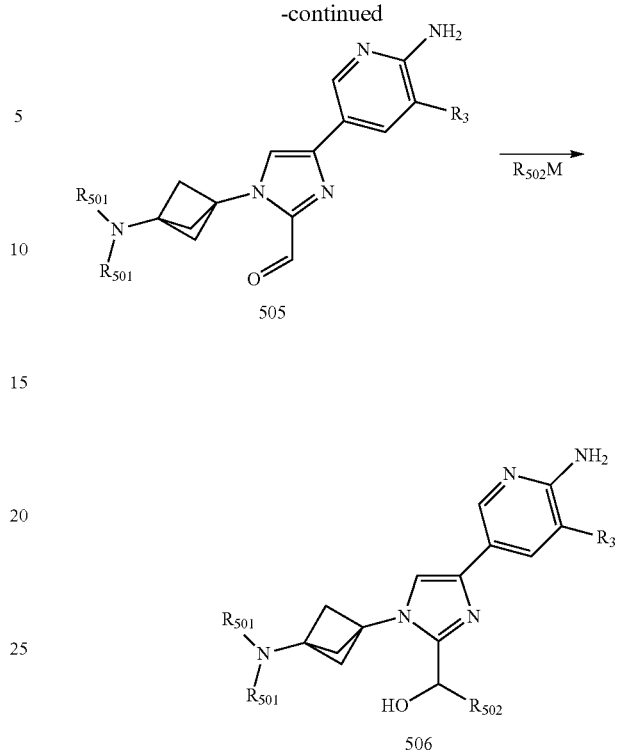

Example 7a/b, and similar compounds, can be synthesized by using the general synthetic procedure set forth in Scheme IV. The first step of Scheme I is performed using $R_1$=BnOCH$_2$ to give Boc/(benzyl)oxy compound 501. Conversion to the diiodo compound 502 is followed by Boc removal and amine alkylation to give tertiary amine 503. The monoiodo compound is obtained by reaction with Grignard reagent, followed by acid quench, to give 504. The procedure of Scheme IV is continued to afford aldehyde 505, which is transformed to secondary alcohol 506. Optionally, the enantiomers of 506 can be separated by methods known in the field (not shown), such as chromatography. It is well understood by one trained in the art that many obvious modifications to the above general route can be envisioned to modify the $R_3$, $R_{502}$, and $R_{502}$ groups.

Scheme V

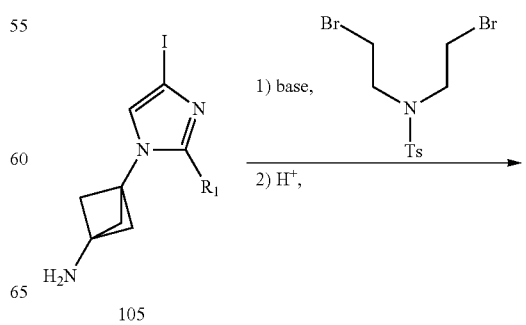

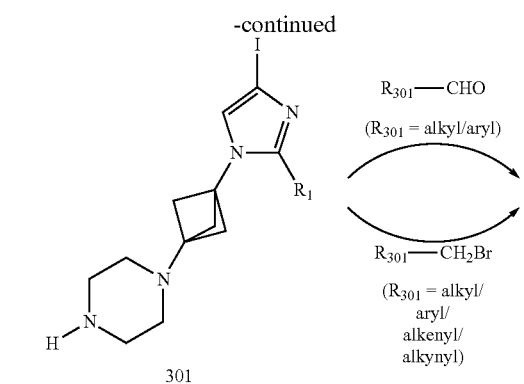

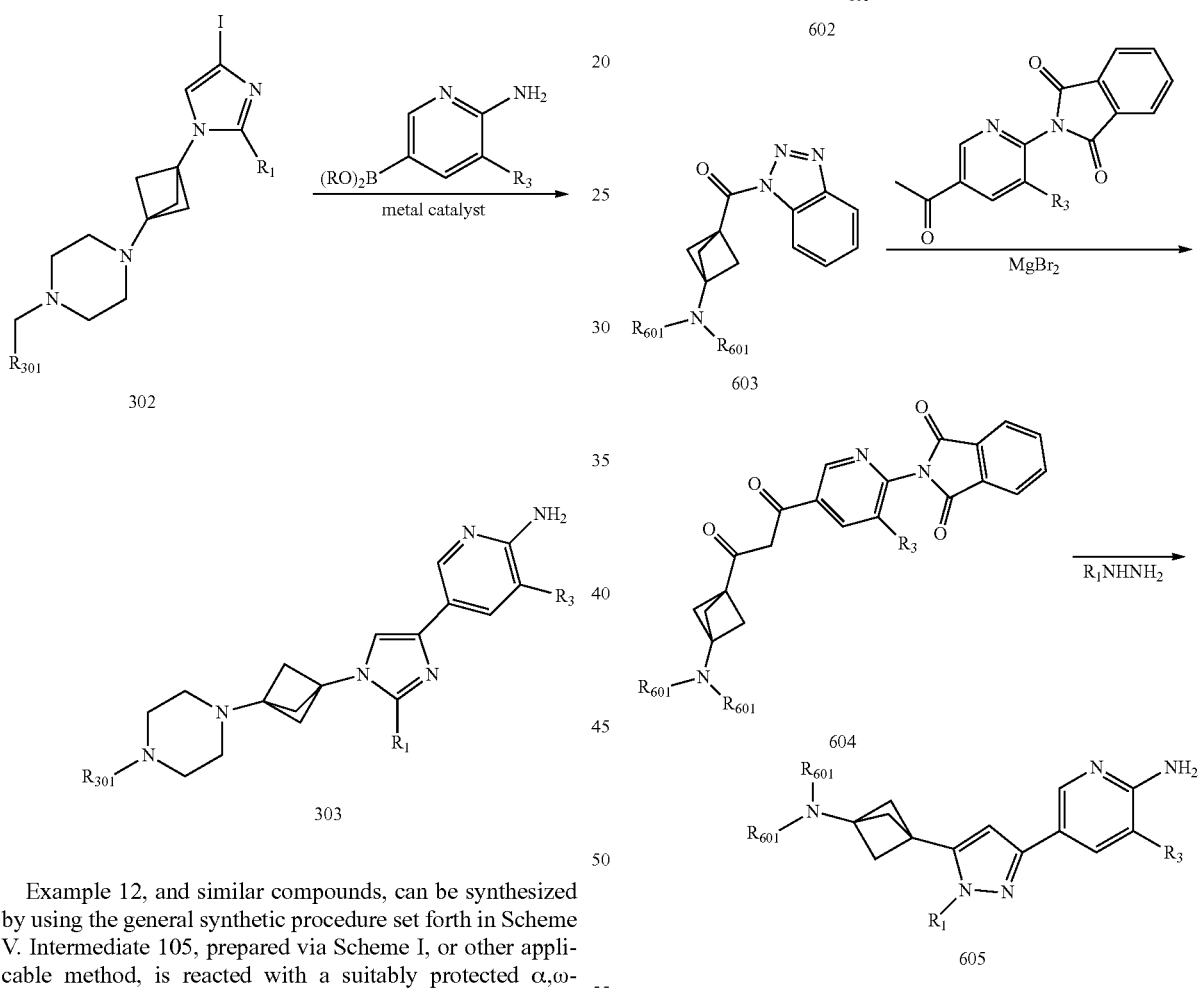

Example 12, and similar compounds, can be synthesized by using the general synthetic procedure set forth in Scheme V. Intermediate 105, prepared via Scheme I, or other applicable method, is reacted with a suitably protected α,ω-dibromo compound, such as the N-tosyl compound shown, to give a cyclic amine. Removal of the tosyl group is accomplished in acid to give 301. This compound can be carried on to the next step, or optionally modified under alkylation or reductive amination conditions with an appropriate alkylating agent or carboxaldehyde, to give 302. Synthesis is completed by coupling 302 as shown in Scheme I or Scheme II. The functional group $R_{301}$ can be modified at this point if desired. It is well understood by one trained in the art that many obvious modifications to the above general route can be envisioned to modify the $R_1$, $R_3$, and $R_{301}$ groups.

Example 11, and similar compounds, can be synthesized by using the general synthetic procedure set forth in Scheme VI. Boc-protected amino bicycloester 601 is deprotected with acid, then reacted with alkylating agent to give tertiary amine 602. The ester is hydrolyzed, and the resulting carboxylic acid is converted to benzotriazole amide 603. Reaction with phthalimide protectedacetylpyridine gives diketone 604, which is reacted with substituted hydrazine, which accomplishes both pyrazole formation and phthalimide cleavage. It is well understood by one trained in the art that many obvious modifications to the above general route can be envisioned to modify the $R_1$, $R_3$, and $R_{601}$ groups.

Scheme VII

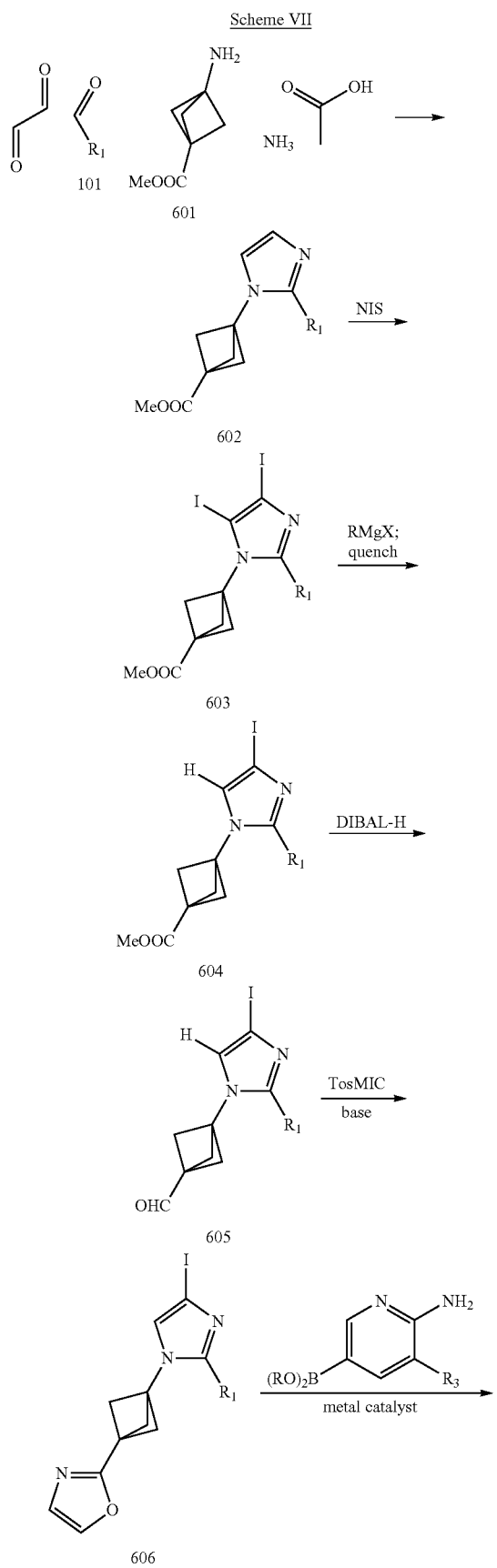

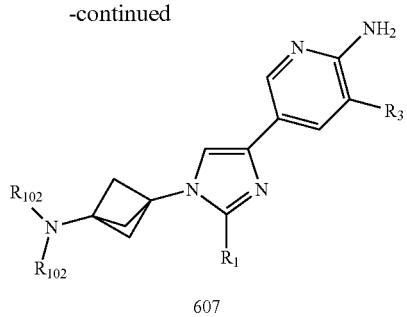

Example 27, and similar compounds, can be synthesized by using the general synthetic procedure set forth in Scheme VII. Imidazole 602 is obtained from reaction of aldehyde 101, glyoxal, and amine/ester 601. Reaction with two equivalents of NIS gives the 4,5-diiodo compound 603. Transmetalation with a Grignard reagent takes place selectively at the 5-position, and the resulting organometallic species is quenched with H$^+$ to give the 4-iodo compound 604. The ester group is reduced to the aldehyde with DIBAL-H to give carboxaldehyde 605. Reaction with p-toluenesulfonylmethyl isocyanide (TosMIC) forms the oxazole group of 606. The target compound 607 is obtained by the coupling techniques disclosed above. It is well understood by one trained in the art that many obvious modifications to the above general route can be envisioned to modify the R$_1$, R$_3$, and R$_{102}$ groups.

The invention is further illustrated by the following examples.

Example 1

5-(2-cyclopropyl-1-(3-morpholinobicyclo[1.1.1]pentan-1-yl)-1H-imidazol-4-yl)-3-(trifluoromethoxy)pyridin-2-amine

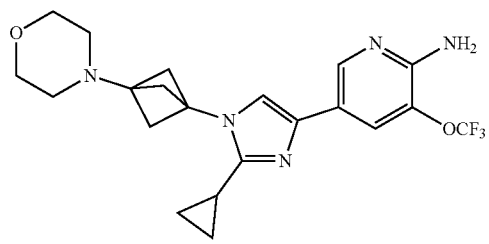 [SMILES: Nc1ncc(-c2cn(C34CC(N5CCOCC5)(C3)C4)c(C3CC3)n2)cc1OC(F)(F)F]

Step 1: tert-butyl (3-(2-cyclopropyl-1H-imidazol-1-yl)bicyclo[1.1.1]pentan-1-yl)carbamate To a solution of cyclopropanecarbaldehyde (0.70 g, 10 mmol) in MeOH (10 ml) at 25° C. was added tert-butyl (3-aminobicyclo[1.1.1]pentan-1-yl)carbamate (1.98 g, 10 mmol) dropwise followed by addition of NH$_4$OAc (0.77 g, 10 mmol). Glyoxal (1.45 g, 10 mmol) was then added dropwise and the mixture was allowed to stir at 25° C. for 24 h, then concentrated under reduced pressure. The residue was purified by SiO$_2$ gel chromatography (0% to 8% MeOH in CH$_2$Cl$_2$) to give the title compound as a pale yellow foamy solid (1.75 g, 60% yield). MS (ES$^+$) C$_{16}$H$_{23}$N$_3$O$_2$ requires: 289, found: 290 [M+H]$^+$.

Step 2: tert-Butyl (3-(2-cyclopropyl-4,5-diiodo-1H-imidazol-1-yl)bicyclo[1.1.1]pentan-1-yl)carbamate To a solution of the product from the previous step (1.75 g, 6.05 mmol) in DMF (20 ml) was added NIS (4.08 g, 18.1 mmol) and the resulting mixture was stirred at 60° C. for 1 h. Sat. aq. Na$_2$S$_2$O$_3$ (10 ml) and water (100 ml) were then added. The aqueous phase was extracted with EtOAc (3×50 mL), and the combined organic layers were washed with sat. aq. NaCl, dried over MgSO$_4$, filtered and concentrated under reduced pressure. The residue was purified by SiO$_2$ gel chromatography (0% to 30% EtOAc in hexanes) to give the title compound as a white foamy solid (1.94 g, 59%). MS (ES$^+$) C$_{16}$H$_{21}$I$_2$N$_3$O$_2$ requires: 541, found: 542 [M+H]$^+$.

Step 3: tert-Butyl (3-(2-cyclopropyl-4-iodo-1H-imidazol-1-yl)bicyclo[1.1.1]pentan-1-yl)carbamate To a solution of the product from the previous step (1.94 g, 3.58 mmol) in THF (30 ml) was added 2.0 M iPrMgCl in THF solution (2.69 ml, 5.38 mmol), and the resulting mixture was stirred at −15° C. for 1 h. Sat. aq. NH$_4$Cl (50 mL) was added, and the layers were separated. The aqueous layer was extracted with EtOAc (3×50 mL), and the combined organic layers were washed with sat. aq. NaCl, dried over MgSO$_4$, filtered and concentrated under reduced pressure. The residue was purified via SiO$_2$ gel chromatography (0% to 40% EtOAc in hexanes) to give the title compound as a white foamy solid (1.27 g, 85%). MS (ES$^+$) C$_{16}$H$_{22}$IN$_3$O$_2$ requires: 415, found: 416 [M+H]$^+$.

Step 4: 3-(2-cyclopropyl-4-iodo-1H-imidazol-1-yl)bicyclo[1.1.1]pentan-1-amine bis(2,2,2-trifluoroacetate)

A solution of the product from the previous step (1.27 g, 3.06 mmol) in TFA (10 ml) and CH$_2$Cl$_2$ (10 ml) was stirred at 20° C. for 2 h, then concentrated under reduced pressure. The residue was lyophilized to give the crude title compound as a white solid (assumed quantitative yield), which was used in the next step without further purification. MS (ES$^+$) C$_{11}$H$_{14}$IN$_3$ requires: 315, found: 316 [M+H]$^+$.

Step 5: 4-(3-(2-cyclopropyl-4-iodo-1H-imidazol-1-yl)bicyclo[1.1.1]pentan-1-yl)morpholine To a solution of the product from the previous step (1.2 g, 2.2 mmol) in MeCN (20 ml) were added K$_2$CO$_3$ (1.527 g, 11.05 mmol) and 1-bromo-2-(2-bromoethoxy)ethane (1.54 g, 6.63 mmol) and the resulting mixture was stirred at 90° C. for 16 h. The reaction mixture was filtered through CELITE®, and the filtrate was concentrated under reduced pressure. The residue was purified via SiO$_2$ gel chromatography (0% to 4% MeOH in CH$_2$Cl$_2$) to give the title compound as a white solid (630 mg, 74%). MS (ES$^+$) C$_{15}$H$_{20}$IN$_3$O requires: 385, found: 386 [M+H]$^+$.

Step 6: 5-(2-cyclopropyl-1-(3-morpholinobicyclo[1.1.1]pentan-1-yl)-1H-imidazol-4-yl)-3-(trifluoromethoxy)pyridin-2-amine A degassed solution of the product from the previous step (630 mg, 1.64 mmol), 5-(4,4,5,5-tetramethyl-1,3,2-dioxaborolan-2-yl)-3-(trifluoromethoxy)pyridin-2-amine (597 mg, 1.96 mmol), PdCl$_2$(dppf)-CH$_2$Cl$_2$ (66.8 mg, 0.082 mmol) and K$_2$CO$_3$ (2.45 ml, 4.91 mmol) in DMF (10 ml) was stirred at 90° C. for 1 h. Water (50 ml) and 1M aq. HCl (10 ml) were added, and the resulting mixture was extracted with EtOAc (3×30 ml). The aqueous layer was basified with 10% aq. NaOH to pH 5 and then with sat. aq. NaHCO$_3$ to pH 8. The aqueous layer was then extracted with EtOAc (3×50 ml). The combined organic layers were washed with sat. aq. NaCl, dried over MgSO$_4$, filtered and concentrated under reduced pressure. The residue was purified via SiO$_2$ gel chromatography (0% to 8% MeOH in CH$_2$Cl$_2$) to give the title compound as a white solid (560 mg, 79%). MS (ES$^+$) C$_{21}$H$_{24}$F$_3$N$_5$O$_2$ requires: 435, found: 436 [M+H]$^+$. $^1$H NMR (MeOD) δ: 8.22 (s, 1H), 7.78 (s, 1H), 7.31 (s, 1H), 3.73 (t, 4H, J=4.6 Hz), 2.56 (t, 4H, J=4.4 Hz), 2.44 (s, 6H), 2.05-1.99 (m, 1H), 1.03-0.96 (m, 4H).

Example 2

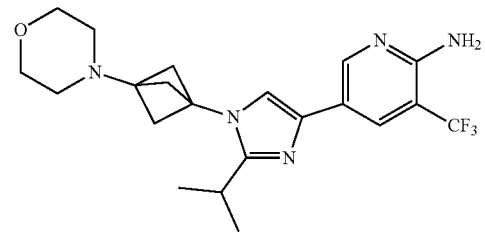 [SMILES: CC(C)c1nc(-c2cnc(N)c(C(F)(F)F)c2)cn1C12CC(N3CCOCC3)(C1)C2]

Example 2 was made in a similar fashion to example 1, using isobutyraldehyde in Step 1 and 5-(4,4,5,5-tetramethyl-1,3,2-dioxaborolan-2-yl)-3-(trifluoromethyl)pyridin-2-amine in Step 6. MS (ES$^+$) C$_{21}$H$_{26}$F$_3$N$_5$O requires: 421, found: 422 [M+H]$^+$. $^1$H NMR (MeOD) δ: 8.52 (d, 1H, J=2.0 Hz), 8.17 (d, 1H, J=1.9 Hz), 7.8 (s, 1H), 3.77 (t, 4H, J=4.6 Hz), 3.65-3.59 (m, 1H), 2.68 (t, 4H, J=4.6 Hz), 2.59 (s, 6H), 1.46 (d, 6H, J=7.0 Hz).

Example 3

5-(2-isopropyl-1-(3-morpholinobicyclo[1.1.1]pentan-1-yl)-1H-imidazol-4-yl)-3-(trifluoromethoxy)pyridin-2-amine

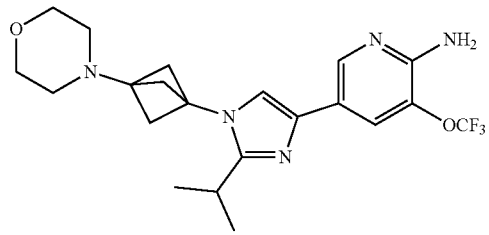 [SMILES: CC(C)c1nc(-c2cnc(N)c(OC(F)(F)F)c2)cn1C12CC(N3CCOCC3)(C1)C2]

Step 1: tert-Butyl (3-(2-isopropyl-1H-imidazol-1-yl)bicyclo[1.1.1]pentan-1-yl)carbamate To a solution of isobutyraldehyde (14.55 g, 201.8 mmol) in MeOH (500 ml) were added tert-butyl (3-aminobicyclo[1.1.1]pentan-1-yl)carbamate (40 g, 200 mmol), NH$_4$OAc (15.55 g, 201.7 mmol) and 40% aq. glyoxal (29.3 g, 202 mmol). The mixture was stirred at 25° C. for 16 h, then concentrated under reduced pressure. To the residue was added sat. aq. NaHCO$_3$ (500 mL) and the mixture was extracted with EtOAc (3×300 mL). The combined organic layers were washed with sat. aq. NaCl, dried over MgSO$_4$, filtered and concentrated under reduced pressure to give the crude title compound (52.5 g, 89%), which was used without further purification. MS (ES$^+$) C$_{16}$H$_{25}$N$_3$O$_2$ requires: 291, found: 292 [M+H]$^+$.

Step 2: tert-Butyl (3-(4,5-diiodo-2-isopropyl-1H-imidazol-1-yl)bicyclo[1.1.1]pentan-1-yl)carbamate To a solution of the product from the previous step (52.5 g, 180 mmol) in DMF (200 ml) was added NIS (122 g, 541 mmol) and the resulting mixture was stirred at 80° C. for 1 h. To the mixture were added water (1000 ml) and sat. aq. Na$_2$S$_2$O$_3$ (100 ml), and the mixture was extracted with EtOAc (3×300 mL). The combined organic layers were washed with sat. aq. NaCl, dried over MgSO$_4$, filtered and concentrated under reduced pressure. The residue was purified by SiO$_2$ gel chromatography (0 to 40% EtOAc in hexanes) to give the title compound as a white foamy solid (29.8 g, 30%). MS (ES$^+$) C$_{16}$H$_{23}$I$_2$N$_3$O$_2$ requires: 543, found: 544 [M+H]$^+$.

Step 3: tert-butyl (3-(4-iodo-2-isopropyl-1H-imidazol-1-yl)bicyclo[1.1.1]pentan-1-yl)carbamate To a solution of the product from the previous step (29.8 g, 54.9 mmol) in THF (300 ml) was added a 2.0 M iPrMgCl in THF solution (35.7 ml, 71.3 mmol), and the resulting mixture was stirred at −78° C. for 1 h then treated with sat. aq. NH$_4$Cl (500 mL). The aqueous phase was extracted with EtOAc (3×200 mL), and the combined organic layers were washed with sat. aq. NaCl, dried over MgSO$_4$, filtered and concentrated under reduced pressure. The residue was purified by SiO$_2$ gel chromatography (0 to 50% EtOAc in hexanes) to give the title compound as a white solid (21.4 g, 93%). MS (ES$^+$) C$_{16}$H$_{24}$IN$_3$O$_2$ requires: 417, found: 418 [M+H]$^+$.

Step 4: 3-(4-iodo-2-isopropyl-1H-imidazol-1-yl)bicyclo[1.1.1]pentan-1-amine dihydrochloride AcCl (72.9 ml, 1030 mmol) was added dropwise to MeOH (300 ml). The resulting solution was allowed to cool to RT, then added to a flask containing the product from the previous step (21.4 g, 51.3 mmol) The resulting mixture was stirred at RT for 6 h, then concentrated under reduced pressure to give the crude title compound as a white solid (22.3 g, 111%), which was used without further purification. MS (ES$^+$) C$_{11}$H$_{16}$IN$_3$ requires: 317, found: 318 [M+H]$^+$.

Step 5: 4-(3-(4-iodo-2-isopropyl-1H-imidazol-1-yl)bicyclo[1.1.1]pentan-1-yl)morpholine To a solution of the product from the previous step (20 g, 51 mmol) in MeCN (300 ml) were added 1-bromo-2-(2-bromoethoxy)ethane (35.7 g, 154 mmol) and K$_2$CO$_3$ (28.4 g, 205 mmol), and the resulting mixture was stirred at 90° C. for 16 h. The mixture was allowed to cool to RT, then filtered through CELITE® and the filtrate was concentrated under reduced pressure. The residue was purified by SiO$_2$ gel chromatography (0 to 4% MeOH in DCM) to give the title compound as a white solid (16.1 g, 81%). MS (ES$^+$) C$_{15}$H$_{22}$IN$_3$O requires: 387, found: 388 [M+H]$^+$.

Step 6: 5-(2-isopropyl-1-(3-morpholinobicyclo[1.1.1]pentan-1-yl)-1H-imidazol-4-yl)-3-(trifluoromethoxy)pyridin-2-amine A degassed solution of the product from the previous step (16.1 g, 41.6 mmol), 5-(4,4,5,5-tetramethyl-1,3,2-dioxaborolan-2-yl)-3-(trifluoromethoxy)pyridin-2-amine (12.6 g, 41.6 mmol), PdCl$_2$(dppf)-CH$_2$Cl$_2$ (1.698 g, 2.079 mmol) and 2.0 M aq. K$_2$CO$_3$ (41.6 ml, 83 mmol) in DMF (100 ml) was stirred at 90° C. for 2 h. The mixture was allowed to cool to RT, then water (1000 ml) and 1 M aq. HCl (100 mL) were added. The aqueous phase was extracted with EtOAc (3×300 mL). The aqueous layer was adjusted to pH 8-9 using 10% aq. NaOH, then extracted with EtOAc (3×300 ml). The second set of combined organic layers were washed with sat. aq. NaCl, dried over MgSO$_4$, filtered and concentrated under reduced pressure. The residue was purified by SiO$_2$ gel chromatography (0 to 10% MeOH in DCM) to give the title compound as a white solid (14.2 g, 78%). MS (ES$^+$) C$_{21}$H$_{26}$F$_3$N$_5$O$_2$ requires: 437, found: 438 [M+H]$^+$. $^1$H NMR (CD$_3$OD) δ 8.28 (d, 1H, J=2.0 Hz), 7.90 (s, 1H), 7.77 (s, 1H), 3.78 (t, 4H, J=4.7 Hz), 3.64-3.58 (m, 1H), 2.71 (t, 4H, J=4.7 Hz), 2.60 (s, 6H), 1.46 (d, 6H, J=7.0 Hz).

Example 4

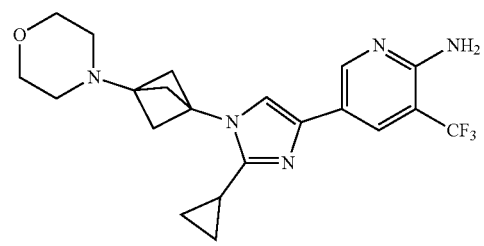 [SMILES: Nc1ncc(-c2cn(C34CC(N5CCOCC5)(C3)C4)c(C3CC3)n2)cc1C(F)(F)F]

Example 4 was made in a similar fashion to example 1, using 5-(4,4,5,5-tetramethyl-1,3,2-dioxaborolan-2-yl)-3-(trifluoromethyl)pyridin-2-amine in Step 6. MS (ES$^+$) C$_{21}$H$_{24}$F$_3$N$_5$O requires: 419, found: 420 [M+H]$^+$. $^1$H NMR (MeOD) δ: 8.48 (d, 1H, J=2.0 Hz), 8.14 (d, 1H, J=1.9 Hz), 7.82 (s, 1H), 3.80 (t, 4H, J=4.6 Hz), 2.79 (t, 4H, J=4.4 Hz), 2.66 (s, 6H), 2.34-2.29 (m, 1H), 1.39-1.23 (m, 4H).

Example 5a/b (S)-(4-(6-amino-5-(trifluoromethyl)pyridin-3-yl)-1-(bicyclo[1.1.1]pentan-1-yl)-1H-imidazol-2-yl)(cyclopropyl)methanol and (R)-(4-(6-amino-5-(trifluoromethyl)pyridin-3-yl)-1-(bicyclo[1.1.1]pentan-1-yl)-1H-imidazol-2-yl)(cyclopropyl)methanol

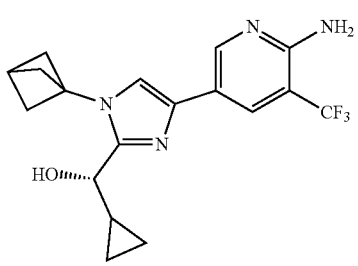

-continued

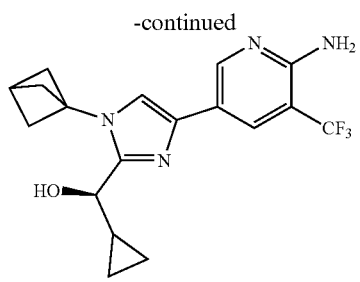

Step 1: (4-(6-amino-5-(trifluoromethyl)pyridin-3-yl)-1-(bicyclo[1.1.1]pentan-1-yl)-1H-imidazol-2-yl)(cyclopropyl)methanol A mixture of 4-(6-amino-5-(trifluoromethyl)pyridin-3-yl)-1-(bicyclo[1.1.1]pentan-1-yl)-1H-imidazole-2-carbaldehyde (180 mg, 0.559 mmol) and cyclopropylmagnesium chloride (56.3 mg, 0.559 mmol) in THF (2793 al) was stirred at 0° C. for 2 h. The mixture was diluted with EtOAc and washed with sat. aq. NH$_4$Cl. The organic layer was filtered through cotton and concentrated under reduced pressure. The residue was purified by reverse phase preparative HPLC (Mobile phase: A=0.1% TFA/water, B=0.1% TFA/MeCN; Gradient: B=10% to 30% in 12 min; Column: C18) to give the racemic title compound (90 mg, 44%). MS (ES$^+$): C$_{18}$H$_{19}$F$_3$N$_4$O requires: 364, found: 365 [M+H]+. The racemic title compound was separated by chiral HPLC (Column: Enantiopak AD (100×4.6 mm 5 um); eluant: 0.2% ammonia in MeOH) to obtain two enantiomers. Enantiomers were assigned by analogy to examples 7a and 7b.

5a: (Retention time=1.62 min) was isolated as a white solid (12.7 mg, 14%). MS (ES$^+$): C$_{18}$H$_{19}$F$_3$N$_4$O requires: 364, found: 365 [M+H]$^+$. $^1$H NMR (500 MHz, CDCl$_3$) δ: 8.56 (s, 1H), 8.09 (s, 1H), 7.03 (s, 1H), 4.94 (s, 2H), 4.67-4.49 (m, 1H), 2.83-2.73 (m, 1H), 2.66 (s, 1H), 2.35 (t, J=7.3 Hz, 6H), 1.32-1.15 (m, 1H), 0.71-0.29 (m, 4H).

5b: (Retention time=2.24 min) was isolated as a white solid (15.7 mg, 17%). MS (ES$^+$): C$_{18}$H$_{19}$F$_3$N$_4$O requires: 364, found: 365 [M+H]$^+$. $^1$H NMR (500 MHz, CDCl$_3$) δ 8.56 (s, 1H), 8.09 (s, 1H), 7.03 (s, 1H), 4.94 (s, 2H), 4.67-4.49 (m, 1H), 2.83-2.73 (m, 1H), 2.66 (s, 1H), 2.35 (t, J=7.3 Hz, 6H), 1.32-1.15 (m, 1H), 0.71-0.29 (m, 4H).

Example 6a/b (S)-1-(4-(6-amino-5-(trifluoromethyl)pyridin-3-yl)-1-(bicyclo[1.1.1]pentan-1-yl)-1H-imidazol-2-yl)-2,2,2-trifluoroethanol and (R)-1-(4-(6-amino-5-(trifluoromethyl)pyridin-3-yl)-1-(bicyclo[1.1.1]pentan-1-yl)-1H-imidazol-2-yl)-2,2,2-trifluoroethanol

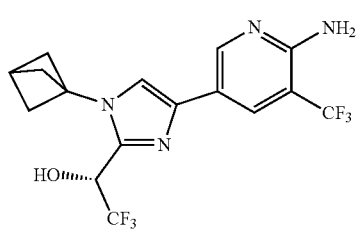

-continued

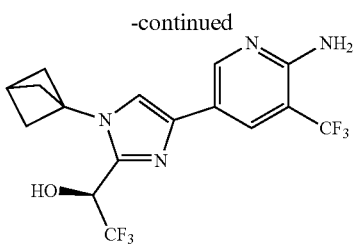

Step 1: 2-((benzyloxy)methyl)-1-(bicyclo[1.1.1]pentan-1-yl)-4,5-diiodo-1H-imidazole To a solution of 2-(benzyloxy)acetaldehyde (600 mg, 4.00 mmol) in MeOH (3.3 mL) were added bicyclo[1.1.1]pentan-1-amine (831 mg, 10.0 mmol), NH$_4$OAc (771 mg, 10.0 mmol) and 40% aq. glyoxal (1451 mg, 10.00 mmol). The resulting mixture was stirred at RT for 6 h, then concentrated under reduced pressure. The residue was diluted with EtOAc, washed with water, and concentrated under reduced pressure to give crude 2-(benzyloxymethyl)-1-(bicyclo[1.1.1]pentan-1-yl)-1H-imidazole (MS (ES$^+$) C$_{16}$H$_{18}$N$_2$O requires: 254, found: 255 [M+H]$^+$), which was dissolved in DMF (3.3 mL) then treated with NIS (6750 mg, 30.0 mmol). The mixture was stirred at 90° C. for 30 min, allowed to cool to RT, then treated with sat. aq. Na$_2$S$_2$O$_3$. The mixture was rapidly stirred at RT for 30 min, then partitioned between EtOAc and water. The organic layer was concentrated under reduced pressure, and the residue was purified by SiO$_2$ gel chromatography (0% to 100% EtOAc in hexanes) to give the title compound as a brown solid (1200 mg, 24%). MS (ES$^+$) C$_{16}$H$_{16}$I$_2$N$_2$O requires: 506, found: 507 [M+H]$^+$.

Step 2: 2-(benzyloxymethyl)-1-(bicyclo[1.1.1]pentan-1-yl)-4-iodo-1H-imidazole

To a solution of the product from the previous step (0.5 g, 1 mmol) in THF (10 mL) at −60° C. was added a 3.0 M EtMgBr in Et$_2$O solution (1 mL, 3 mmol), and the mixture was stirred for 30 min then treated with sat. aq. NH$_4$Cl. The mixture was extracted with EtOAc (3×50 mL), and the combined organic layers were washed with sat. aq. NaCl (30 mL), dried over Na$_2$SO$_4$, filtered and concentrated under reduced pressure to give the title compound as a yellow oil (0.35 g, 92%), which was used without further purification. MS (ES$^+$) C$_{16}$H$_{17}$IN$_2$O requires: 380, found: 381 [M+H]$^+$.

Step 3: 5-(2-(benzyloxymethyl)-1-(bicyclo[1.1.1]pentan-1-yl)-1H-imidazol-4-yl)-3-(trifluoromethyl)pyridin-2-amine A mixture of the product from the previous step (230 mg, 0.60 mmol), 5-(4,4,5,5-tetramethyl-1,3,2-dioxaborolan-2-yl)-3-(trifluoromethyl)pyridin-2-amine (208 mg, 0.722 mmol), 2 M aq. K$_2$CO$_3$ (2 mL, 4 mmol) and Pd(dppf)Cl$_2$ (54 mg, 0.065 mmol) in DMF (6 mL) was degassed and purged with N$_2$, then stirred at 90° C. for 30 min. The mixture was allowed to cool to RT, filtered, and the filtrate was concentrated under reduced pressure. The residue was purified by SiO$_2$ gel chromatography (1:1 EtOAc/petroleum ether) to give the title compound (180 mg, 72%). MS (ES$^+$): C$_{22}$H$_{21}$F$_3$N$_4$O requires: 414, found: 415 [M+H]$^+$.

Step 4: (4-(6-amino-5-(trifluoromethyl)pyridin-3-yl)-1-(bicyclo[1.1.1]pentan-1-yl)-1H-imidazol-2-yl)methanol To a mixture of the product from the previous step (180 mg, 0.43 mmol) in DCM (40 mL) at 0° C. was added BF$_3$—SMe$_2$ complex (0.8 mL). The mixture was stirred overnight, allowing to warm to RT, then treated with 1 M aq. NaOH until the aqueous phase had pH=11. The mixture was extracted with DCM (2×50 mL), and the combined organic layers were washed with sat. aq. NaCl (35 mL), dried over Na$_2$SO$_4$, filtered and concentrated under reduced pressure. The residue was purified by SiO$_2$ gel chromatography (10:1 DCM/MeOH) to give the title compound (100 mg, 71%). MS (ES$^+$): C$_{15}$H$_{15}$F$_3$N$_4$O requires: 324, found: 325 [M+H]$^+$.

Step 5: 4-(6-amino-5-(trifluoromethyl)pyridin-3-yl)-1-(bicyclo[1.1.1]pentan-1-yl)-1H-imidazole-2-carbaldehyde To a mixture of the product from the previous step (100 mg, 0.3 mmol) in DCM (40 mL) was added MnO$_2$ (254 mg, 2.92 mmol). The mixture was stirred overnight then filtered through CELITE®, and the filtrate was concentrated under reduced pressure to give the title compound (100 mg, 100%). MS (ES$^+$): C$_{15}$H$_{13}$F$_3$N$_4$O requires: 322, found: 323 [M+H]$^+$.

Step 6: 1-(4-(6-amino-5-(trifluoromethyl)pyridin-3-yl)-1-(bicyclo[1.1.1]pentan-1-yl)-1H-imidazol-2-yl)-2,2,2-trifluoroethanol To a solution of the product from the previous step (50 mg, 0.15 mmol) in THF (5 mL) at 0° C. was added TMSCF$_3$ (0.11 mL, 0.75 mmol). The mixture was stirred for 5 min, then a 1 M solution of TBAF in THF (0.75 mL, 0.75 mmol) was added dropwise. The mixture was stirred overnight, allowing to warm to RT, then treated with sat. aq. NaHCO$_3$ and extracted with EtOAc (3×20 mL). The combined organic layers were washed with sat. aq. NaCl (35 mL), dried over Na$_2$SO$_4$, filtered and concentrated under reduced pressure. The residue was purified by reverse phase preparative HPLC (Mobile phase: A=10 mM ammonium bicarbonate/water, B=MeCN; Gradient: B=5% to 95% in 18 min; Column: C18) to give the racemic title compound as a white solid (30 mg, 50%). MS (ES$^+$): C$_{16}$H$_{14}$F$_6$N$_4$O requires: 392, found: 393 [M+H]$^+$. The racemic title compound was separated by chiral HPLC (Column: Enantiopak AD (100×4.6 mm 5 um); eluant: 0.1% DEA in IPA) to obtain two enantiomers. Enantiomers were assigned by analogy to examples 7a and 7b.

6a: (Retention time=1.38 min) was isolated as a white solid (9 mg, 30%). MS (ES$^+$): C$_{16}$H$_{14}$F$_6$N$_4$O requires: 392, found: 393 [M+H]$^+$. $^1$H NMR (500 MHz, CDCl$_3$) δ: 8.56 (s, 1H), 8.08 (s, 1H), 7.14 (s, 1H), 5.19-5.09 (m, 1H), 5.00 (s, 2H), 4.35-4.15 (m, 1H), 2.71 (s, 1H), 2.40-2.35 (m, 6H).

6b: (Retention time=2.47 min) was isolated as a white solid (11 mg, 36%). MS (ES$^+$): C$_{16}$H$_{14}$F$_6$N$_4$O requires: 392, found: 393 [M+H]$^+$. $^1$H NMR (500 MHz, CDCl$_3$) δ 8.56 (s, 1H), 8.08 (s, 1H), 7.14 (s, 1H), 5.19-5.09 (m, 1H), 5.00 (s, 2H), 4.35-4.15 (m, 1H), 2.71 (s, 1H), 2.40-2.35 (m, 6H).

Examples 7a/7b (S)-1-(4-(6-amino-5-(trifluoromethoxy)pyridin-3-yl)-1-(3-morpholinobicyclo[1.1.1]pentan-1-yl)-1H-imidazol-2-yl)-2-methylpropan-1-ol and (R)-1-(4-(6-amino-5-(trifluoromethoxy)pyridin-3-yl)-1-(3-morpholinobicyclo[1.1.1]pentan-1-yl)-1H-imidazol-2-yl)-2-methylpropan-1-ol

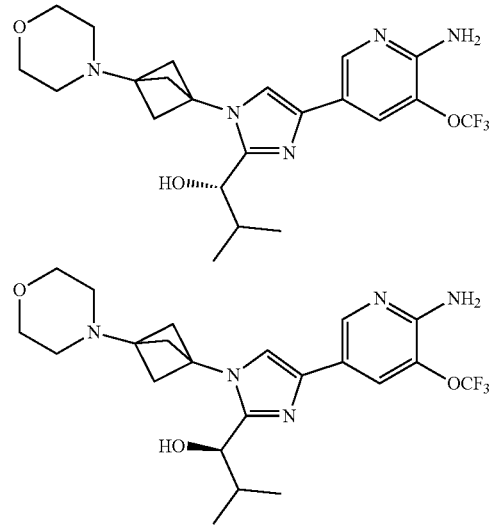

Step 1: tert-butyl N—[3-[2-(benzyloxymethyl)imidazol-1-yl]-1-bicyclo[1.1.1]pentanyl]carbamate To a mixture of benzyloxyacetaldehyde (1.90 mL, 13.1 mmol) in MeOH (60 mL) were added tert-butyl (3-aminobicyclo[1.1.1]pentan-1-yl)carbamate (2.0 g, 10 mmol), NH$_4$OAc (3.14 g, 40.4 mmol) and 40% aq. glyoxal (1.65 mL, 14.4 mmol). The mixture was stirred at RT overnight, then poured into water and extracted with EtOAc. The organic layer was washed with sat. aq. NaCl, dried over Na$_2$SO$_4$, filtered and concentrated under reduced pressure to give the crude title compound as a yellow oil (1.74 g; 47%), which was used directly in the next step. MS (ES$^+$): C$_{21}$H$_{27}$N$_3$O$_3$ requires: 369, found: 370 [M+H]$^+$.

Step 2: tert-butyl 3-(2-(benzyloxymethyl)-4,5-diiodo-1H-imidazol-1-yl)bicyclo[1.1.1]pentan-1-ylcarbamate To a mixture of the product from the previous step (1.74 g, 4.71 mmol) in DMF (50 mL) was added NIS (5.30 g, 23.6 mmol), and the mixture was stirred at 50° C. for 3 h then poured into water and extracted with EtOAc (2×60 mL). The combined organic layers were washed with sat. aq. NaCl (4×20 mL), dried over Na$_2$SO$_4$, filtered and concentrated under reduced pressure. The residue was purified by SiO$_2$ gel chromatography (0% to 40% EtOAc in petroleum ether) to give the title compound as a yellow solid (2.4 g, 82%). MS (ES$^+$): C$_{21}$H$_{25}$I$_2$N$_3$O$_3$ requires: 621, found: 622 [M+H]$^+$.

Step 3: tert-butyl 3-(2-(benzyloxymethyl)-4-iodo-1H-imidazol-1-yl)bicyclo[1.1.1]pentan-1-ylcarbamate To a mixture of the product from the previous step (2.4 g, 3.9 mmol) in THF (45 mL) at −78° C. was added a 3.0 M EtMgBr in Et$_2$O solution (2.58 mL, 7.74 mmol), and the mixture was stirred at −78° C. for 2 h then treated with sat. aq. NH$_4$Cl and extracted with EtOAc (3×60 mL). The combined organic layers were washed with sat. aq. NaCl (45 mL), dried over Na$_2$SO$_4$, filtered and concentrated under reduced pressure. The residue was purified by SiO$_2$ gel chromatography (10% to 60% EtOAc in petroleum ether) to give the title compound as a white solid (1.2 g, 63%). MS (ES$^+$): C$_{21}$H$_{26}$IN$_3$O$_3$ requires: 495, found: 496 [M+H]$^+$.

Step 4: 4-(3-(2-(benzyloxymethyl)-4-iodo-1H-imidazol-1-yl)bicyclo[1.1.1]pentan-1-yl)morpholine To a mixture of the product from the previous step (1.2 g, 2.4 mmol) in DCM (25 mL) was added TFA (5 mL), and the mixture was stirred at RT for 2 h then concentrated under reduced pressure to give crude 3-(2-(benzyloxymethyl)-4-iodo-1H-imidazol-1-yl)bicyclo[1.1.1]pentan-1-amine trifluoroacetate as a brown oil (MS (ES$^+$): C$_{16}$H$_{18}$IN$_3$O requires: 395, found: 396 [M+H]$^+$). The oil was treated with MeCN (25 mL), and to the mixture were added K$_2$CO$_3$ (1.59 g, 11.5 mmol) and bis(2-bromoethyl) ether (1.08 mL, 6.91 mmol). The resulting mixture was stirred at 90° C. for 16 h, then filtered through CELITE® and the filtrate was concentrated under reduced pressure. The residue was purified by SiO$_2$ gel chromatography (0% to 4% MeOH in CH$_2$Cl$_2$) to give the title compound as a white solid (841 mg, 75%). MS (ES$^+$): C$_{20}$H$_{24}$IN$_3$O$_2$, requires: 465, found: 466 [M+H]$^+$.

Step 5: 5-(2-(benzyloxymethyl)-1-(3-morpholinobicyclo[1.1.1]pentan-1-yl)-1H-imidazol-4-yl)-3-(trifluoromethoxy)pyridin-2-amine A mixture of the product from the previous step (445 mg, 956 μmol), 5-(4,4,5,5-tetramethyl-1,3,2-dioxaborolan-2-yl)-3-(trifluoromethoxy)pyridin-2-amine (436 mg, 1.43 mmol), 2 M aq. K$_2$CO$_3$ (2.39 mL, 4.78 mmol) and Pd(dppf)Cl$_2$ (119.54 mg, 143.45 μmol) in DMF (5 mL) was degassed and purged with N$_2$, then stirred at 90° C. for 30 min. The mixture was allowed to cool to RT, filtered, and the filtrate was concentrated under reduced pressure. The residue was purified by SiO$_2$ gel chromatography (10% to 80% EtOAc in petroleum ether) to give the title compound as a white solid (400 mg; 81%). MS (ES$^+$): C$_{26}$H$_{28}$F$_3$N$_5$O$_3$ requires: 515, found: 516 [M+H]$^+$. $^1$H NMR (500 MHz, CDCl$_3$) δ 8.35 (d, J=1.8 Hz, 1H), 7.80 (d, J=1.5 Hz, 1H), 7.41-7.29 (m, 5H), 7.09 (s, 1H), 4.72 (s, 2H), 4.64 (s, 2H), 4.55 (s, 2H), 3.86-3.67 (m, 4H), 2.53-2.44 (m, 4H), 2.31 (s, 6H).

Step 6: (4-(6-amino-5-(trifluoromethoxy)pyridin-3-yl)-1-(3-morpholinobicyclo[1.1.1]pentan-1-yl)-1H-imidazol-2-yl)methanol A mixture of the product from the previous step (436 mg; 846 μmol) in TFA (15 mL) was stirred at reflux overnight then concentrated under reduced pressure. The residue was partitioned between sat. aq. NaHCO$_3$ and DCM, and the organic layer was dried over MgSO$_4$, filtered and concentrated under reduced pressure to give the title compound as a white solid (324 mg, 90%). MS (ES$^+$): C$_{19}$H$_{22}$F$_3$N$_5$O$_3$ requires: 425, found: 426 [M+H]$^+$; $^1$H NMR (500 MHz, CDCl$_3$) δ 8.32 (appar br s, 1H), 7.77 (appar br s, 1H), 7.05 (s, 1H), 4.81 (appar br s, 2H), 4.73 (s, 2H), 3.77 (appar br s, 4H), 2.53 (appar br s, 4H), 2.36 (s, 6H).

Step 7: 4-(6-amino-5-(trifluoromethoxy)pyridin-3-yl)-1-(3-morpholinobicyclo[1.1.1]pentan-1-yl)-1H-imidazole-2-carbaldehyde To a mixture of the product from the previous step (297 mg; 698 μmol) in CHCl$_3$ (75 mL) was added MnO$_2$ (639 mg, 6.98 mmol), and the mixture was stirred at RT overnight, filtered, and the filtrate was concentrated under reduced pressure. The residue was purified by SiO$_2$ gel chromatography (25% to 60% EtOAc in petroleum ether) to give the title compound as a yellow solid (204 mg, 69%). MS (ES$^+$): C$_{19}$H$_{20}$F$_3$N$_5$O$_3$ requires: 423, found: 424 [M+H]$^+$; $^1$H NMR (500 MHz, CDCl$_3$) δ 9.81 (d, J=0.7 Hz, 1H), 8.39 (d, J=1.9 Hz, 1H), 7.87 (s, 1H), 7.29 (d, J=1.5 Hz, 1H), 4.83 (s, 2H), 3.80-3.68 (m, 4H), 2.62-2.50 (m, 4H), 2.45 (s, 6H).

Step 8: (S)-1-(4-(6-amino-5-(trifluoromethoxy)pyridin-3-yl)-1-(3-morpholino bicyclo[1.1.1]pentan-1-yl)-1H-imidazol-2-yl)-2-methylpropan-1-ol and (R)-1-(4-(6-amino-5-(trifluoromethoxy)pyridin-3-yl)-1-(3-morpholino bicyclo[1.1.1]pentan-1-yl)-1H-imidazol-2-yl)-2-methylpropan-1-ol To a mixture of the product from the previous step (186 mg, 439 μmol) in THF (5 mL) at −78° C. was added a 1.3 M iPrMgCl/LiCl solution in THF (5.07 mL, 6.59 mmol) and the mixture was stirred at −78° C. for 2 h, allowed to warm to RT overnight, then treated with sat. aq. NH$_4$Cl and extracted with EtOAc (3×60 mL). The combined organic layers were washed with sat. aq. NaCl (45 mL), dried over Na$_2$SO$_4$, filtered and concentrated under reduced pressure. The residue was purified by SiO$_2$ gel chromatography (0% to 5% MEOH in DCM) to give the racemic title compound as a yellow solid (50.5 mg, 25%). MS (ES$^+$): C$_{22}$H$_{28}$F$_3$N$_5$O$_3$ requires: 467, found: 468 [M+H]$^+$; $^1$H NMR (500 MHz, MeOD) δ 8.33 (d, J=1.9 Hz, 1H), 8.03 (s, 1H), 7.90 (s, 1H), 4.79 (d, J=6.9 Hz, 1H), 3.95-3.73 (m, 4H), 2.98-2.89 (m, 4H), 2.70 (q, J=9.3 Hz, 6H), 2.19 (dq, J=13.4, 6.7 Hz, 1H), 1.12 (d, J=6.6 Hz, 3H), 0.99 (d, J=6.8 Hz, 3H). The racemic title compound was separated by chiral HPLC (Column: OZ—H (100×4.6 mm 5 um); eluant: 0.2% ammonia in MeOH) to obtain two enantiomers. Enantiomers were assigned based on a crystal structure of example 7a bound to a DLK protein construct.

7a: (Retention time=1.74 min) was isolated as a white solid (9.8 mg, 39%). MS (ES$^+$): C$_{22}$H$_{28}$F$_3$N$_5$O$_3$ requires: 467, found: 468 [M+H]$^+$; $^1$H NMR (400 MHz, CDCl$_3$) δ 8.33 (d, J=1.8 Hz, 1H), 7.77 (s, 1H), 7.00 (s, 1H), 4.76 (s, 2H), 4.49 (br s, 1H), 3.79-3.71 (m, 4H), 2.96 (br s, 1H), 2.59-2.44 (m, 4H), 2.40-2.29 (m, 6H), 2.18-2.10 (m, 1H), 1.02 (d, J=6.7 Hz, 3H), 0.96 (d, J=6.8 Hz, 3H).

7b: (Retention time=2.37 min) was isolated as a white solid (9.6 mg, 38%). MS (ES$^+$): C$_{22}$H$_{28}$F$_3$N$_5$O$_3$ requires: 467, found: 468 [M+H]$^+$; $^1$H NMR (400 MHz, CDCl$_3$) δ 8.33 (d, J=1.8 Hz, 1H), 7.77 (s, 1H), 7.00 (s, 1H), 4.78 (s, 2H), 4.49 (br s, 1H), 3.80-3.68 (m, 4H), 3.02 (br s, 1H), 2.62-2.44 (m, 4H), 2.38-2.26 (m, 6H), 2.19-2.11 (m, 1H), 1.02 (d, J=6.7 Hz, 3H), 0.96 (d, J=6.8 Hz, 3H).

Examples 8a/8b (S)-1-(4-(6-amino-5-(trifluoromethoxy)pyridin-3-yl)-1-(3-morpholinobicyclo[1.1.1]pentan-1-yl)-1H-imidazol-2-yl)-2,2,2-trifluoroethanol and (R)-1-(4-(6-amino-5-(trifluoromethoxy)pyridin-3-yl)-1-(3-morpholinobicyclo[1.1.1]pentan-1-yl)-1H-imidazol-2-yl)-2,2,2-trifluoroethanol

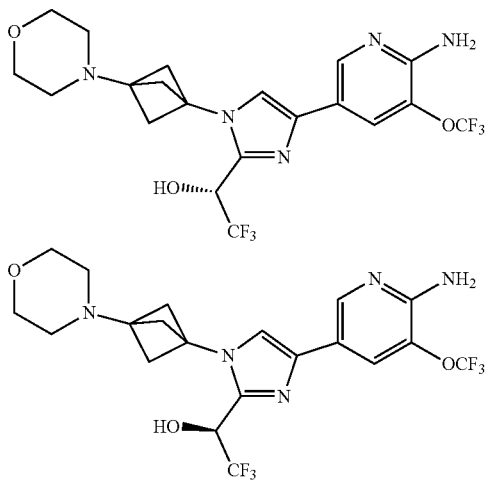

Step 1: 1-(4-(6-amino-5-(trifluoromethoxy)pyridin-3-yl)-1-(3-morpholinobicyclo[1.1.1]pentan-1-yl)-1H-imidazol-2-yl)-2,2,2-trifluoroethanol To a mixture of 4-(6-amino-5-(trifluoromethoxy)pyridin-3-yl)-1-(3-morpholinobicyclo[1.1.1]pentan-1-yl)-1H-imidazole-2-carbaldehyde (340 mg, 0.802 mmol) in THF (25 mL) at 0° C. was added TMSCF$_3$ (1.6 mL, 12 mmol), the mixture was stirred for 5 min, then to it was added dropwise a 1 M TBAF in THF solution (4 mL, 4 mmol). The mixture was stirred overnight, allowing to warm to RT, then treated with sat. aq. NaHCO$_3$ and extracted with EtOAc (3×50 mL). The combined organic layers were washed with sat. aq. NaCl (45 mL), dried over Na$_2$SO$_4$, filtered and concentrated under reduced pressure. The residue was purified by reverse phase preparative HPLC (Mobile phase: A=10 mM ammonium bicarbonate/water, B=MeCN; Gradient: B=5% to 95% in 18 min; Column: C18) to give the racemic title compound as a white solid. MS (ES$^+$): C$_{20}$H$_{21}$F$_6$N$_5$O$_3$ requires: 477, found: 478 [M+H]$^+$. The racemic title compound was separated by chiral HPLC (Column: Enantiopak AD (100×4.6 mm 5 um); eluant: 0.1% DEA in IPA) to obtain two enantiomers. Enantiomers were assigned by analogy to examples 7a and 7b.

8a: (Retention time=1.34 min) was isolated as a white solid (25 mg, 17%). MS (ES$^+$): C$_{20}$H$_{21}$F$_6$N$_5$O$_3$ requires: 493, found: 494 [M+H]$^+$; $^1$H NMR (500 MHz, CDCl$_3$) δ 8.35 (d, J=1.7 Hz, 1H), 7.76 (s, 1H), 7.12 (s, 1H), 5.13 (d, J=5.3 Hz, 1H), 4.81 (s, 2H), 4.56 (s, 1H), 3.93-3.56 (m, 4H), 2.63-2.44 (m, 4H), 2.36 (q, J=9.4 Hz, 6H).

8b: (Retention time=1.82 min) was isolated as a white solid (26 mg, 17%). MS (ES$^+$): C$_{20}$H$_{21}$F$_6$N$_5$O$_3$ requires: 493, found: 494 [M+H]$^+$; $^1$H NMR (500 MHz, CDCl$_3$) δ 8.35 (d, J=1.7 Hz, 1H), 7.76 (s, 1H), 7.12 (s, 1H), 5.13 (d, J=5.3 Hz, 1H), 4.81 (s, 2H), 4.56 (s, 1H), 3.93-3.56 (m, 4H), 2.63-2.44 (m, 4H), 2.36 (q, J=9.4 Hz, 6H).

Examples 9a/9b (S)-1-(4-(6-amino-5-(trifluoromethoxy)pyridin-3-yl)-1-(3-(4-(prop-2-ynyl)piperazin-1-yl)bicyclo[1.1.1]pentan-1-yl)-1H-imidazol-2-yl)-2-methylpropan-1-ol and (R)-1-(4-(6-amino-5-(trifluoromethoxy)pyridin-3-yl)-1-(3-(4-(prop-2-ynyl)piperazin-1-yl)bicyclo[1.1.1]pentan-1-yl)-1H-imidazol-2-yl)-2-methylpropan-1-ol

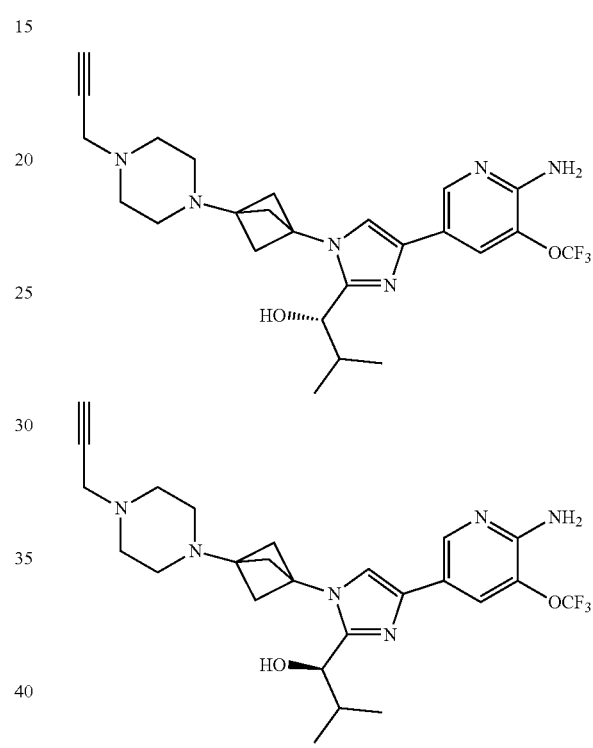

Step 1: 1-(3-(2-(1-(benzyloxy)-2-methylpropyl)-4-iodo-1H-imidazol-1-yl) bicyclo[1.1.1]pentan-1-yl)-4-tosylpiperazine To a solution of tert-butyl 3-(2-(1-(benzyloxy)-2-methylpropyl)-4-iodo-1H-imidazol-1-yl)bicyclo[1.1.1]pentan-1-ylcarbamate (1.00 g, 1.86 mmol) in DCM (10 mL) was added TFA (5 mL). The resulting mixture was stirred at RT for 3 h, then concentrated under reduced pressure to give crude 3-(2-(1-(benzyloxy)-2-methylpropyl)-4-iodo-1H-imidazol-1-yl) bicyclo[1.1.1]pentan-1-amine trifluoroacetate (MS (ES$^+$) C$_{19}$H$_{24}$IN$_3$O requires: 437, found: 438 [M+H]$^+$). This residue was treated with MeCN (15 mL) and to the resulting mixture were added N,N-bis(2-bromoethyl)-4-methylbenzenesulfonamide (2.15 g, 5.58 mmol) and K$_2$CO$_3$ (1.28 g, 9.26 mmol). The resulting mixture was stirred at 90° C. overnight, then filtered through CELITE® and the filtrate was concentrated under reduced pressure. The residue was purified by SiO$_2$ gel chromatography (0% to 90% EtOAc in petroleum ether) to give the title compound as a white solid (680 mg, 55%). MS (ES$^+$): C$_{30}$H$_{37}$IN$_4$O$_3$S requires: 660, found: 661 [M+H]$^+$.

Step 2: 1-(4-iodo-1-(3-(piperazin-1-yl)bicyclo[1.1.1]
pentan-1-yl)-1H-imidazol-2-yl)-2-methylpropan-1-ol To a solution of the product from the previous step (680 mg, 1.03 mmol) in AcOH (5 mL) were added a 40% HBr in AcOH solution (5 mL) and 4-hydroxybenzoic acid (427 mg, 3.09 mmol). The resulting mixture was stirred at RT overnight, then diluted with water (10 mL) and washed with EtOAc (3×20 mL). The aqueous layer was adjusted to pH=1 using NaOH, then extracted with EtOAc (3×20 mL). The second set of combined organic layers was dried over $Na_2SO_4$, filtered and concentrated under reduced pressure to give the crude title compound as a colorless oil (360 mg, 84%), which was used without further purification. MS ($ES^+$): $C_{16}H_{25}IN_4O$ requires: 416, found: 417 $[M+H]^+$.

Step 3: 1-(4-iodo-1-(3-(4-(prop-2-ynyl)piperazin-1-yl)bicyclo[1.1.1] pentan-1-yl)-1H-imidazol-2-yl)-2-methylpropan-1-ol To a solution of the product from the previous step (360 mg, 0.86 mmol) in $CHCl_3$ (8 mL) at 0° C. were added 3-bromoprop-1-yne (153 mg, 1.29 mmol) and DIEA (333 mg, 2.58 mmol). The resulting mixture was stirred at 0° C. for 6 h, then concentrated to give the crude title compound as a white solid (340 mg, 64%), which was used without further purification. MS ($ES^+$) $C_{19}H_{27}IN_4O$ requires: 454, found: 455 $[M+H]^+$.

Step 4: 1-(4-(6-amino-5-(trifluoromethoxy)pyridin-3-yl)-1-(3-(4-(prop-2-ynyl)piperazin-1-yl)bicyclo[1.1.1]pentan-1-yl)-1H-imidazol-2-yl)-2-methylpropan-1-ol To a solution of the crude product from the previous step from the previous step (340 mg, 0.75 mmol) in DMF (3 mL) were added 5-(4,4,5,5-tetramethyl-1,3,2-dioxaborolan-2-yl)-3-(trifluoromethoxy)pyridin-2-amine (456 mg, 1.50 mmol), Pd(dppf)Cl$_2$ (83 mg, 0.11 mmol) and 2 M aq. $K_2CO_3$ (1.875 mL, 3.75 mmol). The resulting mixture was degassed and purged with $N_2$, then stirred at 90° C. for 30 min. The mixture was allowed to cool to RT, filtered, and the filtrate was concentrated under reduced pressure. The residue was purified by reverse phase preparative HPLC (Mobile phase: A=10M NH$_4$HCO$_3$/water, B=MeCN; Gradient: B=30% to 60% in 9.5 min; Column: C18) to give the racemic title compound as a white solid (58 mg, 15%). MS ($ES^+$) $C_{25}H_{31}F_3N_6O_2$ requires: 504, found: 505 $[M+H]^+$. The racemic title compound was separated by chiral HPLC Column: OZ—H (100×4.6 mm 5 um); eluant: 0.1% NH$_3$ in MeOH) to obtain two enantiomers. Enantiomers were assigned by analogy to examples 7a and 7b.

9a: (Retention time=1.29 min) (25 mg, 43%). MS ($ES^+$) $C_{25}H_{31}F_3N_6O_2$ requires: 504, found: 505 $[M+H]^+$. $^1$H NMR (500 MHz, CDCl$_3$) δ 8.33 (d, J=1.8 Hz, 1H), 7.76 (s, 1H), 6.99 (s, 1H), 4.74 (s, 2H), 4.49 (s, 1H), 3.34 (d, J=2.3 Hz, 2H), 2.95 (s, 1H), 2.64 (d, J=27.8 Hz, 8H), 2.35 (q, J=9.4 Hz, 6H), 2.27 (t, J=2.3 Hz, 1H), 2.14 (dd, J=13.2, 6.6 Hz, 1H), 0.99 (dd, J=28.1, 6.7 Hz, 6H).

9b: (Retention time=1.99 min) (19 mg, 32%). MS ($ES^+$) $C_{25}H_{31}F_3N_6O_2$ requires: 504, found: 505 $[M+H]^+$. $^1$H NMR (500 MHz, CDCl$_3$) δ 8.33 (d, J=1.8 Hz, 1H), 7.77 (s, 1H), 7.00 (s, 1H), 4.72 (s, 2H), 4.50 (s, 1H), 3.34 (d, J=2.4 Hz, 2H), 2.85 (s, 1H), 2.64 (d, J=29.2 Hz, 8H), 2.35 (q, J=9.4 Hz, 6H), 2.27 (t, J=2.4 Hz, 1H), 2.13 (dd, J=13.1, 6.6 Hz, 1H), 0.99 (dd, J=21.7, 6.7 Hz, 6H).

Example 10

(S)-1-(4-(6-amino-5-(trifluoromethoxy)pyridin-3-yl)-1-(3-(4-(propyl)piperazin-1-yl)bicyclo[1.1.1]
pentan-1-yl)-1H-imidazol-2-yl)-2-methylpropan-1-ol

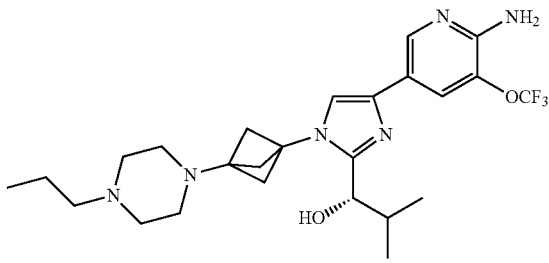 [SMILES: CCCN1CCN(C23CC(n4cc(-c5cnc(N)c(OC(F)(F)F)c5)nc4[C@@H](O)C(C)C)(C2)C3)CC1]

Step 1: (S)-1-(4-(6-amino-5-(trifluoromethoxy)pyridin-3-yl)-1-(3-(4-(propyl) piperazin-1-yl)bicyclo[1.1.1]pentan-1-yl)-1H-imidazol-2-yl)-2-methylpropan-1-ol To a solution of compound 9a (12 mg, 0.024 mmol) in MeOH (3 mL) was added 10% Pd/C (10 mg). The resulting mixture was stirred at RT for 3 h under an atmosphere of H$_2$, then filtered and concentrated under reduced pressure. The residue was purified by reverse phase preparative HPLC (Mobile phase: A=10 mM ammonium bicarbonate/water, B=MeCN; Gradient: B=40% to 70% in 9.7 min; Column: C18) to give the title compound as a white solid (1.2 mg, 9%). MS ($ES^+$) $C_{25}H_{35}F_3N_6O_2$ requires: 508, found: 509 $[M+H]^+$. $^1$H NMR (500 MHz, CDCl$_3$) δ 8.25 (d, J=1.7 Hz, 1H), 7.69 (s, 1H), 6.92 (s, 1H), 4.68 (s, 2H), 4.41 (d, J=6.1 Hz, 1H), 2.52 (br s, 5H), 2.27 (q, J=9.1 Hz, 8H), 2.06 (dd, J=13.3, 6.6 Hz, 1H), 1.50-1.42 (m, 6H), 0.95 (d, J=6.7 Hz, 3H), 0.89-0.82 (m, 6H).

Example 11

5-(1-isopropyl-5-(3-morpholinobicyclo[1.1.1]pentan-1-yl)-1H-pyrazol-3-yl)-3-(trifluoromethyl)pyridin-2-amine

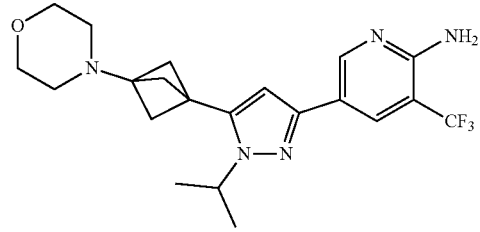 [SMILES: CC(C)n1nc(-c2cnc(N)c(C(F)(F)F)c2)cc1C12CC(N3CCOCC3)(C1)C2]

Preparation of 2-(5-acetyl-3-(trifluoromethyl)pyridin-2-yl)isoindoline-1,3-dione A mixture of 5-bromo-3-(trifluoromethyl)pyridin-2-amine (1500 mg, 6.22 mmol), phthaloyl dichloride (1516 mg, 7.467 mmol), 4-dimethylaminopyridine (152 mg, 1.24 mmol) and TEA (2588 al, 18.67 mmol) in DCM (24.9 ml) was stirred at RT for 1 h, then treated with 1 M aq. HCl (30 mL) and stirred for 3 h. The mixture was diluted with EtOAc (30 mL), washed with sat. aq. NH$_4$Cl (30 mL), and concentrated under reduced pressure. The residue was purified by SiO$_2$ gel chromatography (0% to 100% EtOAc in hexanes) to give 2-(5-bromo-3-(trifluoromethyl)pyridin-2-yl)isoindoline-1,3-dione (600 mg, 26%). MS (ES$^+$) C$_{14}$H$_6$BrF$_3$N$_2$O$_2$ requires: 370, found: 371 [M+H]$^+$.

A mixture of the product from the previous step (630 mg, 1.70 mmol), (Ph$_3$P)$_2$PdCl$_2$ (179 mg, 0.255 mmol), and tributyl(1-ethoxyvinyl)stannane (644 mg, 1.78 mmol) in 1,4-dioxane (6790 al) was stirred at 100° C. for 7 h, then allowed to cool to RT and treated with 10 M aq. KF (3 mL). The resulting mixture was stirred at RT for 1 h, then filtered to remove white solid, diluted with EtOAc (50 mL), washed with sat. aq. NH$_4$Cl (50 mL), and concentrated under reduced pressure. The residue was dissolved in MeOH (50 mL), treated with 1 M aq. HCl (50 mL), and the mixture was stirred at RT for 30 min. The mixture was concentrated under reduced pressure, then partitioned between EtOAc (100 mL) and sat. aq. NaHCO$_3$ (50 mL). The organic layer was concentrated under reduced pressure. The residue was purified by SiO$_2$ gel chromatography (20% to 100% EtOAc in hexanes) to give 2-(5-acetyl-(trifluoromethyl)-pyridin-2-yl)isoindoline-1,3-dione as a white solid (480 mg, 85%). MS (ES$^+$) C$_{16}$H$_9$F$_3$N$_2$O$_3$ requires: 334, found: 335 [M+H]$^+$.

Step 1: methyl 3-morpholinobicyclo[1.1.1]pentane-1-carboxylate

A mixture of methyl 3-((tert-butoxycarbonyl)amino)bicyclo[1.1.1]pentane-1-carboxylate (200 mg, 0.829 mmol) in DCM (2072 al) and TFA (2072 al) was stirred for 2 h and then concentrated under reduced pressure. The residue was treated with MeCN (4150 al), and to the resulting solution were added K$_2$CO$_3$ (574 mg, 4.15 mmol) and 1-bromo-2-(2-bromoethoxy)ethane (577 mg, 2.49 mmol). The resulting mixture was stirred at 90° C. for 2 h, then filtered through CELITE®, and the filtrate was concentrated under reduced pressure. The residue was purified by SiO$_2$ gel chromatography (0% to 4% MeOH in DCM) to give the title compound as a white solid (110 mg, 63%). MS (ES$^+$) C$_{11}$H$_{17}$NO$_3$ requires: 211, found: 212 [M+H]$^+$.

Step 2: (1H-benzo[d][ ][1,2,3]triazol-1-yl)(3-morpholinobicyclo[1.1.1]pentan-1-yl)methanone To a solution of the product from the previous step (1.00 g, 4.73 mmol) in 1:1:1 THF/MeOH/water (12 mL) at RT was added LiOH.H$_2$O (570 mg, 13.6 mmol), and the mixture was stirred at RT for 4 h. The resulting solution was concentrated under reduced pressure, and the residue was diluted with water (15 mL) then extracted with EtOAc (2×15 ml). The aqueous layer was acidified with 1 M aq. HCl to pH=5-6 then concentrated under reduced pressure to obtain 1.2 g of a residue (assumed to be crude 3-morpholinobicyclo[1.1.1]pentane-1-carboxylic acid). The residue was treated with SOCl$_2$ (10 mL), and the resulting mixture was stirred at reflux for 2 h then concentrated under reduced pressure to a residue, which was dissolved in 20 mL of DCM and added dropwise to a solution of 1H-benzo[d][1,2,3]triazole (720 mg, 6.05 mmol) in DCM (10 mL) and Et$_3$N (2.48 mL, 17.8 mmol) at 0° C. The mixture was stirred at RT for 4 h, then treated with sat. aq. NH$_4$Cl (10 mL) at 0° C., then extracted with DCM (20 mL). The organic layer was washed with sat. aq. NaHCO$_3$ (2×20 mL), dried over Na$_2$SO$_4$, and concentrated under reduced pressure to give crude title compound as a grey solid (700 mg, 50%), which was used without further purification. MS (ESI+) C$_{16}$H$_{18}$N$_4$O$_2$ requires: 298, found: 299 [M+H]$^+$.

Step 3: 2-(5-(3-(3-morpholinobicyclo[1.1.1]pentan-1-yl)-3-oxopropanoyl)-3-(trifluoromethyl)-pyridin-2-yl)isoindoline-1,3-dione 2,2,2-trifluoroacetate To a suspension of MgBr2.OEt$_2$ (87 mg, 0.34 mmol), TEA (93 µl, 0.670 mmol) and the product from the previous step (50.0 mg, 0.168 mmol) in DCM (419 µl) was added a solution of 2-(5-acetyl-3-(trifluoromethyl)pyridin-2-yl)isoindoline-1,3-dione (56.0 mg, 0.168 mmol) in DCM (419 al) dropwise. The mixture was stirred for 1 h, then diluted with EtOAc (30 mL), filtered to remove solids, and concentrated under reduced pressure. The residue was purified by reverse phase preparative HPLC (Mobile phase: A=0.1% TFA/water, B=0.1% TFA/MeCN; Gradient: B=30% to 70% in 12 min; Column: C18) to give the title compound as a white solid (67.0 mg, 64%). MS (ES$^+$) C$_{26}$H$_{22}$F$_3$N$_3$O$_5$ requires: 513, found: 514 [M+H]$^+$.

Step 4: 5-(1-isopropyl-5-(3-morpholinobicyclo[1.1.1]pentan-1-yl)-1H-pyrazol-3-yl)-3-(trifluoromethyl)pyridin-2-amine A solution of isopropylhydrazine hydrochloride (35.5 mg, 0.321 mmol) and the product from the previous step (67.0 mg, 0.107 mmol) in EtOH (536 al) was stirred at 70° C. for 2 h, then allowed to cool to RT. To the solution was added NH$_2$NH$_2$.H$_2$O (107 mg, 2.14 mmol) and the mixture was stirred at RT for 20 min then concentrated under reduced pressure. The residue was purified by reverse phase preparative HPLC (Mobile phase: A=0.1% TFA/water, B=0.1% TFA/MeCN; Gradient: B=20% to 50% in 12 min; Column: C18) to give two products as a mixture of TFA salts, which were separated by basic reverse phase preparative HPLC (Mobile phase: A=0.1% NH$_3$/water, B=0.1% NH$_3$/MeCN; Gradient: B=0% to 90% in 20 min; Column: C18) to give the title compound as a white solid (4 mg, 9%). MS (ES$^+$) C$_{21}$H$_{26}$F$_3$N$_5$O requires: 421, found: 422 [M+H]$^+$. $^1$H NMR (600 MHz, CD$_3$OD) δ 8.51 (d, J=1.95 Hz, 1H), 8.11 (d, J=1.95 Hz, 1H), 6.35 (s, 1H), 4.66 (q, J=6.6 Hz, 1H), 3.72 (t, J=4.6 Hz, 4H), 2.55 (t, J=4.5 Hz, 4H), 2.21 (s, 6H), 1.48 (d, J=6.9 Hz, 6H). Another isomer, 5-(1-isopropyl-3-(3-morpholinobicyclo[1.1.1]pentan-1-yl)-1H-pyrazol-5-yl)-3-(trifluoromethyl)pyridin-2-amine, was also isolated as a white solid (10 mg, 22%). MS (ES$^+$) C$_{21}$H$_{26}$F$_3$N$_5$O requires: 421, found: 422 [M+H]$^+$. $^1$H NMR (600 MHz, CDCl$_3$) δ 8.21 (d, J=1.95 Hz, 1H), 7.66 (d, J=1.95 Hz, 1H), 6.07 (s, 1H), 5.11 (s, 2H), 4.36 (q, J=6.6 Hz, 1H), 3.77 (s, 4H), 2.53 (s, 4H), 2.11 (s, 6H), 1.45 (d, J=6.9 Hz, 6H).

Example 12

5-(2-cyclopropyl-1-(3-(4-methylpiperazin-1-yl)bicyclo[1.1.1]pentan-1-yl)-1H-imidazol-4-yl)-3-(trifluoromethoxy)pyridin-2-amine

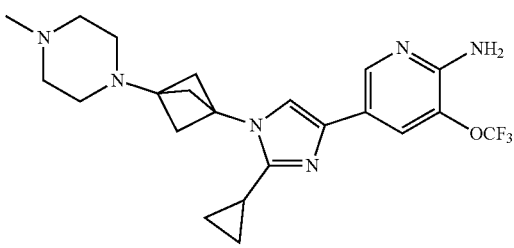 [SMILES: CN1CCN(C23CC(n4cc(-c5cnc(N)c(OC(F)(F)F)c5)nc4C4CC4)(C2)C3)CC1]

Step 1: 1-(3-(2-cyclopropyl-4-iodo-1H-imidazol-1-yl)bicyclo[1.1.1]pentan-1-yl)-4-tosylpiperazine To a solution of 3-(2-cyclopropyl-4-iodo-1H-imidazol-1-yl)bicyclo[1.1.1]pentan-1-amine 2,2,2-trifluoroacetate (600 mg, 1.4 mmol) in MeCN (20 mL) were added N,N-bis(2-bromoethyl)-4-methylbenzenesulfonamide (1.29 g, 3.36 mmol) and $K_2CO_3$ (774 mg, 5.60 mmol). The resulting mixture was stirred at 90° C. overnight, then filtered through CELITE®, and the filtrate was concentrated under reduced pressure. The residue was purified by $SiO_2$ gel chromatography (0% to 90% EtOAc in petroleum ether) to give the title compound (200 mg, 26%). MS (ES+): $C_{22}H_{27}IN_4O_2S$ requires: 538, found: 539 [M+H]+.

Step 2: 1-(3-(2-cyclopropyl-4-iodo-1H-imidazol-1-yl)bicyclo[1.1.1]pentan-1-yl)piperazine To a solution of the product from the previous step (200 mg, 0.37 mmol) in AcOH (0.5 mL) was added a 40% HBr in AcOH solution (0.5 mL). The resulting mixture was stirred at 90° C. for 1 h. The mixture was concentrated under reduced pressure, the residue was slurried with 0.5 mL MeOH, and solid was collected to give the title compound (100 mg, 71%). MS (ES+): $C_{15}H_{21}IN_4$ requires: 384, found: 385 [M+H]+.

Step 3: 1-(3-(2-cyclopropyl-4-iodo-1H-imidazol-1-yl)bicyclo[1.1.1]pentan-1-yl)-4-methylpiperazine To a mixture of the product from the previous step (100 mg, 0.26 mmol) in MeOH (5 mL) was added a 38% aq. formaldehyde solution (2.0 ml). The mixture was stirred at RT for 1 h, then treated with $NaBH_3CN$ (20 mg, 0.31 mmol) and stirred at RT overnight. The mixture was concentrated under reduced pressure, and the residue was purified by reverse phase preparative HPLC (Mobile phase: A=10 mM ammonium bicarbonate/water, B=MeCN; Gradient: B=60% to 95% in 18 min; Column: C18) to give the title compound as a white solid (40.0 mg; 40%). MS (ES+): $C_{16}H_{23}IN_4$ requires: 398, found: 399 [M+H]+.

Step 4: 5-(2-cyclopropyl-1-(3-(4-methylpiperazin-1-yl)bicyclo[1.1.1]pentan-1-yl)-1H-imidazol-4-yl)-3-(trifluoromethoxy)pyridin-2-amine A mixture of the product from the previous step (40 mg, 0.1 mmol), 5-(4,4,5,5-tetramethyl-1,3,2-dioxaborolan-2-yl)-3-(trifluoromethoxy)pyridin-2-amine (36 mg, 0.12 mmol), 2 M aq. $K_2CO_3$ (0.19 mL, 0.38 mmol) and Pd(dppf)$Cl_2$ (13.54 mg, 16.25 μmol) in DMF (1 mL) was degassed and purged with $N_2$, then stirred at 90° C. for 30 min. The mixture was allowed to cool to RT, filtered, and concentrated under reduced pressure. The residue was purified by reverse phase preparative HPLC (Mobile phase: A=10 mM $NH_4HCO_3$/$H_2O$, B=MeCN; Gradient: B=0% to 45% in 18 min; Column: C18) to give the title compound as a yellow solid (5.5 mg; 12%). MS (ES+): $C_{22}H_{27}F_3N_6O$ requires: 448, found: 449 [M+H]+; 1H NMR (500 MHz, CDCl$_3$) δ 8.30 (s, 1H), 7.75 (s, 1H), 6.97 (s, 1H), 4.67 (s, 2H), 2.48-2.40 (m, 17H), 1.89 (tt, J=8.3, 5.0 Hz, 1H), 1.13-0.83 (m, 4H).

Example 13

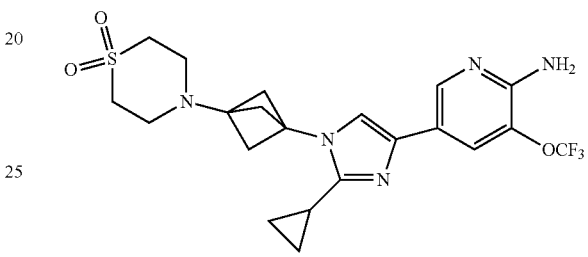

4-(3-(4-(6-amino-5-(trifluoromethoxy)pyridin-3-yl)-2-cyclopropyl-1H-imidazol-1-yl)bicyclo[1.1.1]pentan-1-yl)thiomorpholine 1,1-dioxide

Step 1: 4-(3-(2-cyclopropyl-4-iodo-1H-imidazol-1-yl)bicyclo[1.1.1]pentan-1-yl)thiomorpholine 1,1-dioxide To a solution of 3-(2-cyclopropyl-4-iodo-1H-imidazol-1-yl)bicyclo[1.1.1]pentan-1-amine bis(2,2,2-trifluoroacetate) (150 mg, 0.276 mmol) in EtOH (1 ml) were added DIEA (0.241 ml, 1.38 mmol) and (vinylsulfonyl)ethene (65.3 mg, 0.552 mmol), and the resulting mixture was stirred at 60° C. for 2 h. The precipitate that formed was collected by filtration to give the title compound as a white solid (95 mg, 79%). MS (ES+) $C_{15}H_{20}IN_3O_2S$ requires: 433, found: 434 [M+H]+.

Step 2: 4-(3-(4-(6-amino-5-(trifluoromethoxy)pyridin-3-yl)-2-cyclopropyl-1H-imidazol-1-yl)bicyclo[1.1.1]pentan-1-yl)thiomorpholine 1,1-dioxide A degassed solution of the product from the previous step (94 mg, 0.22 mmol), 5-(4,4,5,5-tetramethyl-1,3,2-dioxaborolan-2-yl)-3-(trifluoromethoxy)pyridin-2-amine (79 mg, 0.26 mmol), PdCl$_2$(dppf)-CH$_2$Cl$_2$ (17.7 mg, 0.022 mmol) and 2 M aq. $K_2CO_3$ (0.325 ml, 0.650 mmol) in DMF (1 ml) was stirred at 90° C. for 1 h. To the mixture were added 1 M aq. HCl (1 mL) and water (10 ml) and the mixture was extracted with EtOAc (3×5 mL). The aqueous phase was adjusted to pH=5 with 10% aq. NaOH, then to pH=8-9 with sat. aq. NaHCO$_3$. The aqueous phase was then extracted with EtOAc (3×10 ml). The combined organic layers were washed with sat aq. NaCl, dried over MgSO$_4$, filtered and concentrated under reduced pressure. The residue was purified by SiO$_2$ gel chromatography (0% to 5% MeOH in DCM) to give the title compound as a white solid (62 mg, 59%). MS (ES⁺) $C_{21}H_{24}F_3N_5O_3S$ requires: 483, found: 484 [M+H]⁺. ¹H NMR (CD₃OD) δ 8.21 (d, 1H, J=2.0 Hz), 7.77 (s, 1H), 7.30 (s, 1H), 3.17-3.07 (m, 8H), 2.48 (s, 6H), 2.05-1.98 (m, 1H), 1.03-0.96 (m, 4H).

Example 14

5-(1-(3-(1,4-oxazepan-4-yl)bicyclo[1.1.1]pentan-1-yl)-2-cyclopropyl-1H-imidazol-4-yl)-3-(trifluoromethoxy)pyridin-2-amine

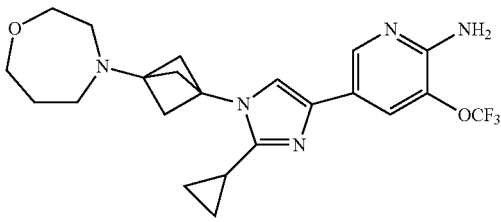 [SMILES: Nc1ncc(-c2cn(C34CC(N5CCCOCC5)(C3)C4)c(C3CC3)n2)cc1OC(F)(F)F]

Step 1: 3-(2-(tosyloxy)ethoxy)propyl 4-methylbenzenesulfonate

To a solution of 3-(2-hydroxyethoxy)propan-1-ol (240 mg, 2.00 mmol) in pyridine (2 ml) at 0° C. was added 4-toluenesulfonyl chloride (800 mg, 4.19 mmol) and the resulting mixture was stirred at 0° C. for 2 h. The mixture was poured into ice water, and precipitate was isolated by filtration to give the title compound as a white solid (658 mg, 77%). MS (ES⁺) $C_{19}H_{24}O_7S_2$ requires: 428, found: 429 [M+H]⁺.

Step 2: 4-(3-(2-cyclopropyl-4-iodo-1H-imidazol-1-yl)bicyclo[1.1.1]pentan-1-yl)-1,4-oxazepane To a solution of 3-(2-cyclopropyl-4-iodo-1H-imidazol-1-yl)bicyclo[1.1.1]pentan-1-amine bis(2,2,2-trifluoroacetate) (50 mg, 0.092 mmol) in MeCN (1 mL) were added K₂CO₃ (63.6 mg, 0.460 mmol) and the product from the previous step (79 mg, 0.18 mmol), and the resulting mixture was stirred at 90° C. for 8 h. The mixture was filtered through CELITE®, and the filtrate was concentrated under reduced pressure. The residue was purified by SiO₂ gel chromatography (0% to 8% MeOH in DCM) to give the title compound as a white solid (15 mg, 41%). MS (ES⁺) $C_{16}H_{22}IN_3O$ requires: 399, found: 400 [M+H]⁺.

Step 3: 5-(1-(3-(1,4-oxazepan-4-yl)bicyclo[1.1.1]pentan-1-yl)-2-cyclopropyl-1H-imidazol-4-yl)-3-(trifluoromethoxy)pyridin-2-amine bis(2,2,2-trifluoroacetate)

A degassed solution of the product from the previous step (15 mg, 0.038 mmol), 5-(4,4,5,5-tetramethyl-1,3,2-dioxaborolan-2-yl)-3-(trifluoromethoxy)pyridin-2-amine (13.7 mg, 0.045 mmol), PdCl₂(dppf)-CH₂Cl₂ (3.07 mg, 3.76 μmol) and 2 M aq. K₂CO₃ (0.056 ml, 0.112 mmol) in DMF (0.5 ml) was stirred at 90° C. for 1 h. The mixture was diluted with EtOAc, filtered through CELITE®, and the filtrate was concentrated under reduced pressure. The residue was purified by reverse phase preparative HPLC (Mobile phase: A=0.1% TFA/water, B=0.1% TFA/MeCN; Gradient: B=0% to 30% in 12 min; Column: C18) to give the title compound as a white powder (5 mg, 20%). MS (ES⁺) $C_{22}H_{26}F_3N_5O_2$ requires: 449, found: 450 [M+H]⁺. ¹H NMR (MeOD) δ 8.25 (d, 1H, J=2.0 Hz), 7.94 (s, 1H), 7.82 (s, 1H), 3.95 (t, 2H, J=4.8 Hz), 3.87 (t, 2H, 6.1 Hz), 3.52 (t, 2H, J=5.4 Hz), 3.46 (t, 2H, J=4.8 Hz), 2.92 (s, 6H), 2.29-2.18 (m, 3H), 1.35-1.22 (m, 4H).

Example 15

5-(2-cyclopropyl-1-(3-(4-(2,2,2-trifluoroethyl)piperazin-1-yl)bicyclo[1.1.1]pentan-1-yl)-1H-imidazol-4-yl)-3-(trifluoromethoxy)pyridin-2-amine

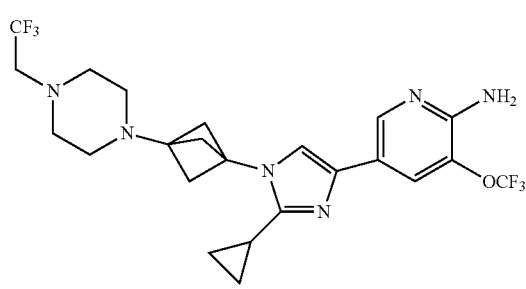 [SMILES: Nc1ncc(-c2cn(C34CC(N5CCN(CC(F)(F)F)CC5)(C3)C4)c(C3CC3)n2)cc1OC(F)(F)F]

Step 1: 1-(3-(2-cyclopropyl-4-iodo-1H-imidazol-1-yl)bicyclo[1.1.1]pentan-1-yl)piperazine bis(2,2,2-trifluoroacetate)

To a solution of 1-(3-(2-cyclopropyl-4-iodo-1H-imidazol-1-yl)bicyclo[1.1.1]pentan-1-yl)-4-tosylpiperazine (100 mg, 0.186 mmol) in AcOH (1 ml) was added a 30% HBr in AcOH solution (0.336 ml) and the resulting mixture was stirred at RT for 16 h then concentrated under reduced pressure. The residue was purified by reverse phase preparative HPLC (Mobile phase: A=0.1% TFA/water, B=0.1% TFA/MeCN; Gradient: B=0% to 30% in 12 min; Column: C18) to give the title compound as a white solid (66 mg, 58%). MS (ES⁺) $C_{15}H_{21}IN_4$ requires: 384, found: 385 [M+H]⁺.

Step 2: 1-(3-(2-cyclopropyl-4-iodo-1H-imidazol-1-yl)bicyclo[1.1.1]pentan-1-yl)-4-(2,2,2-trifluoroethyl) piperazine To a solution of the product from the previous step (15 mg, 0.024 mmol) in MeCN (0.5 ml) were added DIEA (0.021 ml, 0.122 mmol) and 2,2,2-trifluoroethyl trifluoromethanesulfonate (11.4 mg, 0.049 mmol). The resulting mixture was stirred at 60° C. for 1 h, then concentrated under reduced pressure. The residue was purified by reverse phase preparative HPLC (Mobile phase: A=0.1% TFA/water, B=0.1% TFA/MeCN; Gradient: B=10% to 40% in 12 min; Column: C18) to give the title compound as a white solid (7 mg, 41%). MS (ES⁺) $C_{17}H_{22}F_3IN_4$ requires: 466, found: 467 [M+H]⁺.

Step 3: 5-(2-cyclopropyl-1-(3-(4-(2,2,2-trifluoroethyl)piperazin-1-yl)bicyclo[1.1.1]pentan-1-yl)-1H-imidazol-4-yl)-3-(trifluoromethoxy)pyridin-2-amine A degassed solution of the product from the previous step (7 mg, 10 μmol), 5-(4,4,5,5-tetramethyl-1,3,2-dioxaborolan-2-yl)-3-(trifluoromethoxy)pyridin-2-amine (3.68 mg, 0.012 mmol), PdCl$_2$(dppf)-CH$_2$Cl$_2$ (0.823 mg, 1.01 μmol) and 3.0 M aq. K$_2$CO$_3$ (10 al, 0.030 mmol) in DMF (0.5 ml) was stirred at 90° C. for 1 h. The residue was purified by reverse phase preparative HPLC (Mobile phase: A=0.1% TFA/water, B=0.1% TFA/MeCN; Gradient: B=10% to 40% in 12 min; Column: C18) to give the title compound as a white solid (4 mg, 46%). MS (ES$^+$) C$_{23}$H$_{26}$F$_6$N$_6$O requires: 516, found: 517 [M+H]$^+$. $^1$H NMR (CD$_3$OD) δ 8.25 (d, 1H, J=1.9 Hz), 7.94 (s, 1H), 7.83 (s, 1H), 3.31-3.26 (m, 2H), 3.23-3.14 (m, 4H), 3.07-2.98 (m, 4H), 2.81 (s, 6H), 2.30-2.25 (m, 1H), 1.35-1.22 (m, 4H).

Example 16

5-(2-cyclopropyl-1-(3-(4-(methylsulfonyl)piperazin-1-yl)bicyclo[1.1.1]pentan-1-yl)-1H-imidazol-4-yl)-3-(trifluoromethoxy)pyridin-2-amine

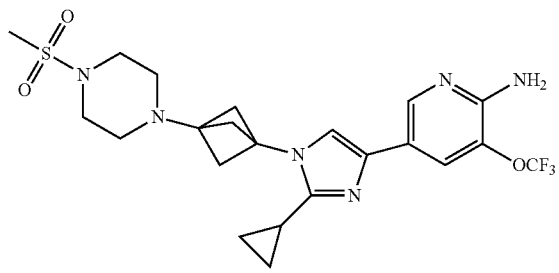 [SMILES: CS(=O)(=O)N1CCN(C23CC(n4cc(-c5cnc(N)c(OC(F)(F)F)c5)nc4C4CC4)(C2)C3)CC1]

Step 1: 1-(3-(2-cyclopropyl-4-iodo-1H-imidazol-1-yl)bicyclo[1.1.1]pentan-1-yl)-4-(methylsulfonyl)piperazine bis(2,2,2-trifluoroacetate)

To a solution of 1-(3-(2-cyclopropyl-4-iodo-1H-imidazol-1-yl)bicyclo[1.1.1]pentan-1-yl)piperazine bis(2,2,2-trifluoroacetate) (15 mg, 0.024 mmol) in MeCN (0.5 ml) were added DIEA (0.021 ml, 0.122 mmol) and methanesulfonyl chloride (3.82 al, 0.049 mmol). The resulting mixture was stirred at 60° C. for 1 h then concentrated under reduced pressure. The residue was purified by reverse phase preparative HPLC (Mobile phase: A=0.1% TFA/water, B=0.1% TFA/MeCN; Gradient: B=10% to 40% in 12 min; Column: C18) to give the title compound as a colorless liquid (9 mg, 53%). MS (ES$^+$) C$_{16}$H$_{23}$IN$_4$O$_2$S requires: 462, found: 463 [M+H]$^+$.

Step 2: 5-(2-cyclopropyl-1-(3-(4-(methylsulfonyl)piperazin-1-yl)bicyclo[1.1.1]pentan-1-yl)-1H-imidazol-4-yl)-3-(trifluoromethoxy)pyridin-2-amine bis(2,2,2-trifluoroacetate)

A degassed solution of the product from the previous step (9.0 mg, 0.013 mmol), 5-(4,4,5,5-tetramethyl-1,3,2-dioxaborolan-2-yl)-3-(trifluoromethoxy)pyridin-2-amine (4.76 mg, 0.016 mmol), PdCl$_2$(dppf)-CH$_2$Cl$_2$ (1.065 mg, 1.304 μmol) and 3 M aq. K$_2$CO$_3$ (0.013 ml, 0.039 mmol) in DMF (0.5 ml) was stirred at 90° C. for 1 h then concentrated under reduced pressure. The residue was purified by reverse phase preparative HPLC (Mobile phase: A=0.1% TFA/water, B=0.1% TFA/MeCN; Gradient: B=0% to 30% in 12 min; Column: C18) to give the title compound as a white powder (5 mg, 52%). MS (ES$^+$) C$_{22}$H$_{27}$F$_3$N$_6$O$_3$S requires: 512, found: 513 [M+H]$^+$. $^1$H NMR (MeOD) δ 8.26 (d, 1H, J=1.8 Hz), 7.92 (s, 1H), 7.82 (s, 1H), 3.34-3.30 (m, 4H), 2.88 (s, 3H), 2.78-2.73 (m, 4H), 2.60 (s, 6H), 2.34-2.29 (m, 1H), 1.36-1.23 (m, 4H).

Example 17

5-(2-cyclopropyl-1-(3-(4-(2-fluoroethyl)piperazin-1-yl)bicyclo[1.1.1]pentan-1-yl)-1H-imidazol-4-yl)-3-(trifluoromethoxy)pyridin-2-amine

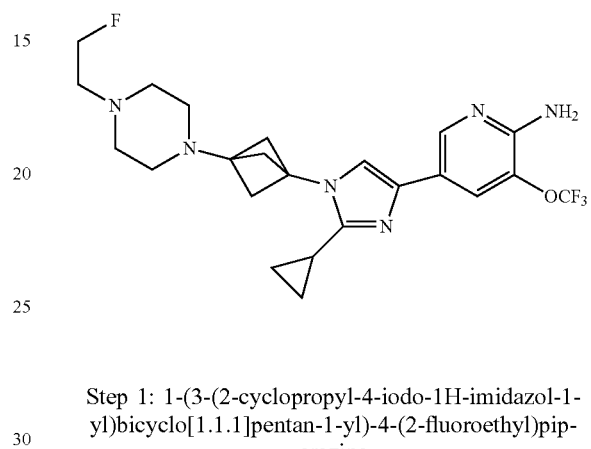

Step 1: 1-(3-(2-cyclopropyl-4-iodo-1H-imidazol-1-yl)bicyclo[1.1.1]pentan-1-yl)-4-(2-fluoroethyl)piperazine To a solution of 1-(3-(2-cyclopropyl-4-iodo-1H-imidazol-1-yl)bicyclo[1.1.1]pentan-1-yl)piperazine bis(2,2,2-trifluoroacetate) (30 mg, 0.049 mmol) in MeCN (1 ml) were added K$_2$CO$_3$ (33.9 mg, 0.245 mmol) and 1-fluoro-2-iodoethane (17.0 mg, 0.098 mmol) and the resulting mixture was stirred at 60° C. for 1 h then concentrated under reduced pressure. The residue was purified by reverse phase preparative HPLC (Mobile phase: A=0.1% TFA/water, B=0.1% TFA/MeCN; Gradient: B=10% to 40% in 12 min; Column: C18) to give the title compound as a colorless liquid (9.0 mg, 42%). MS (ES$^+$) C$_{17}$H$_{24}$F$_1$N$_4$ requires: 430, found: 431 [M+H]$^+$.

Step 2: 5-(2-cyclopropyl-1-(3-(4-(2-fluoroethyl)piperazin-1-yl)bicyclo[1.1.1]pentan-1-yl)-1H-imidazol-4-yl)-3-(trifluoromethoxy)pyridin-2-amine tris(2,2,2-trifluoroacetate)

A degassed solution of the product from the previous step, 5-(4,4,5,5-tetramethyl-1,3,2-dioxaborolan-2-yl)-3-(trifluoromethoxy)pyridin-2-amine (6.22 mg, 0.020 mmol), PdCl$_2$(dppf)-CH$_2$Cl$_2$ (1.518 mg, 1.859 μmol) and K$_2$CO$_3$ (7.71 mg, 0.056 mmol) in DMF (1 ml) was stirred at 90° C. for 1 h. The mixture was diluted with EtOAc, filtered through CELITE®, and the filtrate was concentrated under reduced pressure. The residue was purified by reverse phase preparative HPLC (Mobile phase: A=0.1% TFA/water, B=0.1% TFA/MeCN; Gradient: B=10% to 40% in 12 min; Column: C18) to give the title compound as a white solid (10 mg, 65% yield). MS (ES$^+$) C$_{23}$H$_{28}$F$_4$N$_6$O requires: 480, found: 481 [M+H]$^+$. $^1$H NMR (CD$_3$OD) δ 8.27 (d, 1H, J=1.6 Hz), 7.99 (s, 1H), 7.84 (s, 1H), 4.91 (t, 1H, J=4.3 Hz), 4.83 (t, 1H, J=4.3 Hz), 3.61 (t, 1H, J=4.3 Hz), 3.57 (t, 1H, J=4.3 Hz), 3.21-2.90 (m, 8H), 2.59 (s, 6H), 2.34-2.29 (m, 1H), 1.36-1.23 (m, 4H).

Example 18

4-(3-(2-cyclopropyl-4-(3-(trifluoromethyl)-1H-pyr-rolo[2,3-b]pyridin-5-yl)-1H-imidazol-1-yl)bicyclo[1.1.1]pentan-1-yl)morpholine

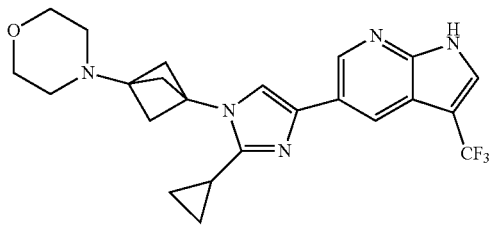 [SMILES: FC(F)(F)c1c[nH]c2ncc(-c3cn(C45CC(N6CCOCC6)(C4)C5)c(C4CC4)n3)cc12]

Step 1: 4-(3-(2-cyclopropyl-4-(3-(trifluoromethyl)-1-((2-(trimethylsilyl)ethoxy)methyl)-1H-pyrrolo[2,3-b]pyridin-5-yl)-1H-imidazol-1-yl)bicyclo[1.1.1]pentan-1-yl)morpholine bis(2,2,2-trifluoroacetate)

A degassed solution of 4-(3-(2-cyclopropyl-4-iodo-1H-imidazol-1-yl)bicyclo[1.1.1]pentan-1-yl)morpholine (Example 1, Step 5, 30 mg, 0.078 mmol), 5-(4,4,5,5-tetramethyl-1,3,2-dioxaborolan-2-yl)-3-(trifluoromethyl)-1-((2-(trimethylsilyl)ethoxy)methyl)-1H-pyrrolo[2,3-b]pyridine (41.3 mg, 0.093 mmol), PdCl$_2$(dppf)-CH$_2$Cl$_2$ (6.36 mg, 7.79 μmol) and 2 M aq. K$_2$CO$_3$ (0.117 ml, 0.234 mmol) in DMF (1 ml) was stirred at 90° C. for 2 h. The mixture was diluted with EtOAc, filtered through CELITE®, and the filtrate was concentrated under reduced pressure. The residue was purified by reverse phase preparative HPLC (Mobile phase: A=0.1% TFA/water, B=0.1% TFA/MeCN; Gradient: B=20% to 60% in 12 min; Column: C18) to give the title compound as a white powder (23 mg, 37%). MS (ES$^+$) C$_{29}$H$_{38}$F$_3$N$_5$O$_2$Si requires: 573, found: 574 [M+H]$^+$.

Step 2: 4-(3-(2-cyclopropyl-4-(3-(trifluoromethyl)-1H-pyrrolo[2,3-b]pyridin-5-yl)-1H-imidazol-1-yl)bicyclo[1.1.1]pentan-1-yl)morpholine bis(2,2,2-trifluoroacetate)

A solution of 4-(3-(2-cyclopropyl-4-(3-(trifluoromethyl)-1-((2-(trimethylsilyl)ethoxy)methyl)-1H-pyrrolo[2,3-b]pyridin-5-yl)-1H-imidazol-1-yl)bicyclo[1.1.1]pentan-1-yl)morpholine bis(2,2,2-trifluoroacetate) (22 mg, 0.027 mmol) in TFA (0.5 ml) and DCM (0.5 ml) was stirred at RT for 6 h, then concentrated under reduced pressure. The residue was dissolved in MeOH, and then ethylenediamine (18.5 al, 0.274 mmol) was added and the resulting mixture was stirred at RT for 3 h then concentrated under reduced pressure. The residue was purified by reverse phase preparative HPLC (Mobile phase: A=0.1% TFA/water, B=0.1% TFA/MeCN; Gradient: B=10% to 40% in 12 min; Column: C18) to give the title compound as a white powder (13 mg, 71%). MS (ES$^+$) C$_{23}$H$_{24}$F$_3$N$_5$O requires: 443, found: 444 [M+H]$^+$. $^1$H NMR (CD$_3$OD) δ 8.27 (d, 1H, J=1.6 Hz), 7.99 (s, 1H), 7.84 (s, 1H), 4.91 (t, 1H, J=4.3 Hz), 4.83 (t, 1H, J=4.3 Hz), 3.61 (t, 1H, J=4.3 Hz), 3.57 (t, 1H, J=4.3 Hz), 3.21-2.90 (m, 8H), 2.59 (s, 6H), 2.34-2.29 (m, 1H), 1.36-1.23 (m, 4H).

Example 19

5-(2-cyclopropyl-1-(3-(piperidin-1-yl)bicyclo[1.1.1]pentan-1-yl)-1H-imidazol-4-yl)-3-(trifluoromethoxy)pyridin-2-amine

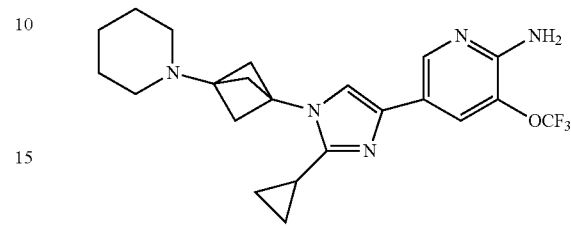

Step 1: 1-(3-(2-cyclopropyl-4-iodo-1H-imidazol-1-yl)bicyclo[1.1.1]pentan-1-yl)piperidine To a solution of 3-(2-cyclopropyl-4-iodo-1H-imidazol-1-yl)bicyclo[1.1.1]pentan-1-amine bis(2,2,2-trifluoroacetate) (50 mg, 0.092 mmol) in MeCN (1 ml) were added K$_2$CO$_3$ (63.6 mg, 0.460 mmol) and 1,5-dibromopentane (63.5 mg, 0.276 mmol), and the resulting mixture was stirred at 90° C. for 8 h. The mixture was filtered through CELITE®, and the filtrate was concentrated under reduced pressure. The residue was purified by SiO$_2$ gel chromatography (0% to 4% MeOH in DCM) to give the title compound as a white solid (26 mg, 74%). MS (ES$^+$) C$_{16}$H$_{22}$IN$_3$ requires: 383, found: 384 [M+H]$^+$.

Step 2: 5-(2-cyclopropyl-1-(3-(piperidin-1-yl)bicyclo[1.1.1]pentan-1-yl)-1H-imidazol-4-yl)-3-(trifluoromethoxy)pyridin-2-amine A degassed solution of the product from the previous step (20 mg, 0.052 mmol), 5-(4,4,5,5-tetramethyl-1,3,2-dioxaborolan-2-yl)-3-(trifluoromethoxy)pyridin-2-amine (26 mg, 0.086 mmol), PdCl$_2$(dppf)-CH$_2$Cl$_2$ (5.82 mg, 7.13 μmol) and 2.0 M aq. K$_2$CO$_3$ (0.107 ml, 0.214 mmol) in DMF (1 ml) was stirred at 90° C. for 2 h. The mixture was diluted with EtOAc, filtered through CELITE®, and the filtrate was concentrated under reduced pressure. The residue was purified by reverse phase preparative HPLC (Mobile phase: A=0.1% TFA/water, B=0.1% TFA/MeCN; Gradient: B=10% to 40% in 12 min; Column: C18) to give the title compound as a bis-trifluoroacetate salt. The salt was dissolved in water (2 ml), and the mixture was adjusted to pH=9 using sat. aq. NaHCO$_3$. The precipitate was isolated by filtration to give the title compound as a white solid (16 mg, 52%). MS (ES$^+$) C$_{22}$H$_{26}$F$_3$N$_5$O requires: 433, found: 434 [M+H]$^+$. $^1$H NMR (CD$_3$OD) δ 8.22 (d, 1H, J=2.0 Hz), 7.80 (s, 1H), 7.49 (s, 1H), 3.10-2.69 (m, 4H), 2.65 (s, 6H), 2.15-2.06 (m, 1H), 1.90-1.48 (m, 6H), 1.16-1.03 (m, 4H).

Example 20

4-(3-(2-cyclopropyl-4-(1H-pyrrolo[3,2-b]pyridin-6-yl)-1H-imidazol-1-yl)bicyclo[1.1.1]pentan-1-yl)morpholine

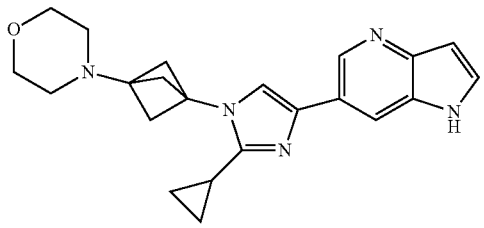 [SMILES: c1cc2ncc(-c3cn(C45CC(N6CCOCC6)(C4)C5)c(C4CC4)n3)cc2[nH]1]

Step 1: 6-bromo-1-((2-(trimethylsilyl)ethoxy)methyl)-1H-pyrrolo[3,2-b]pyridine To a suspension of 60% NaH in mineral oil (120 mg, 3.0 mmol) in DMF (5 ml) at 0° C. was added 6-bromo-1H-pyrrolo[3,2-b]pyridine (394 mg, 2.00 mmol), and the resulting mixture was stirred at 0° C. for 5 min. The mixture was treated with trimethylsilylethoxymethyl chloride (0.532 ml, 3.00 mmol), then stirred at RT for 2 h. The mixture was treated with sat. aq. NH$_4$Cl (10 mL) and extracted with EtOAc (3×5 mL). The combined organic layers were washed with sat. aq. NaCl, dried over MgSO$_4$, filtered and concentrated under reduced pressure. The residue was purified by SiO$_2$ gel chromatography (10% to 60% EtOAc in hexanes) to give the title compound as a yellow liquid (455 mg, 70%). MS (ES$^+$) C$_{13}$H$_{19}$BrN$_2$OSi requires: 326, found: 327 [M+H]$^+$.

Step 2: 6-(4,4,5,5-tetramethyl-, 3,2-dioxaborolan-2-yl)-1-((2-(trimethylsilyl)ethoxy)methyl)-1H-pyrrolo[3,2-b]pyridine A degassed mixture of the product from the previous step (200 mg, 0.611 mmol), bis(pinacolato)diboron (233 mg, 0.917 mmol), PdCl$_2$(dppf)-CH$_2$Cl$_2$ (49.9 mg, 0.061 mmol) and KOAc (180 mg, 1.83 mmol) in 1,4-dioxane (5 ml) was stirred at 90° C. for 2 h. Water (10 mL) was added, and the layers were separated. The aqueous phase was extracted with EtOAc (3×5 mL), and the combined organic layers were washed with sat. aq. NaCl, dried over MgSO$_4$, filtered and concentrated under reduced pressure to give the crude title compound as a brown oil (229 mg, 100%), which was used without further purification. MS (ES$^+$) C$_{19}$H$_{31}$BN$_2$O$_3$Si requires: 374, found: 293 [M−82+H]$^+$.

Step 3: 4-(3-(2-cyclopropyl-4-(1-((2-(trimethylsilyl)ethoxy)methyl)-1H-pyrrolo[3,2-b]pyridin-6-yl)-1H-imidazol-1-yl)bicyclo[1.1.1]pentan-1-yl)morpholine A degassed solution of the product from the previous step (58.3 mg, 0.156 mmol), 4-(3-(2-cyclopropyl-4-iodo-1H-imidazol-1-yl)bicyclo[1.1.1]pentan-1-yl)morpholine (Example 1, Step 5, 60 mg, 0.16 mmol), PdCl$_2$(dppf)-CH$_2$Cl$_2$ (12.7 mg, 0.016 mmol) and 2.0 M aq. K$_2$CO$_3$ (0.234 ml, 0.467 mmol) in DMF (1 ml) was stirred at 90° C. for 2 h. Water (10 mL) was added, and the layers were separated. The aqueous phase was extracted with EtOAc (3×5 mL), and the combined organic layers were washed with sat. aq. NaCl, dried over MgSO$_4$, filtered and concentrated under reduced pressure. The residue was purified by SiO$_2$ gel chromatography (0% to 8% MeOH in DCM) to give the title compound as a tan foamy solid (45 mg, 57%). MS (ES$^+$) C$_{28}$H$_{39}$N$_5$O$_2$Si requires: 505, found: 506 [M+H]$^+$.

Step 4: 4-(3-(2-cyclopropyl-4-(1H-pyrrolo[3,2-b]pyridin-6-yl)-1H-imidazol-1-yl)bicyclo[1.1.1]pentan-1-yl)morpholine bis(2,2,2-trifluoroacetate)

A solution of the product from the previous step (43 mg, 0.085 mmol) in TFA (1 ml) and DCM (1 ml) was stirred at RT for 3 h, then concentrated under reduced pressure. The residue was dissolved in MeOH (1 ml), ethylenediamine (0.115 ml, 1.70 mmol) was added, and the resulting mixture was stirred at RT for 16 h then concentrated under reduced pressure. The residue was purified by reverse phase preparative HPLC (Mobile phase: A=0.1% TFA/water, B=0.1% TFA/MeCN; Gradient: B=0% to 30% in 12 min; Column: C18) to give the title compound as a yellow solid (39 mg, 76%). MS (ES$^+$) C$_{22}$H$_{25}$N$_5$O requires: 375, found: 376 [M+H]$^+$. $^1$H NMR (DMSO-d$_6$) δ 12.49 (s, br, 1H), 8.93 (s, 1H), 8.68 (s, 1H), 8.14 (s, 1H), 7.99 (s, 1H), 6.80 (s, 1H), 3.73-3.64 (m, 4H), 2.66-2.55 (m, 4H), 2.46 (s, 6H), 2.20-2.12 (m, 1H), 1.09-0.97 (m, 4H).

Example 21

4-(3-(2-cyclopropyl-4-(1-(2-fluoroethyl)-1H-pyrrolo[3,2-b]pyridin-6-yl)-1H-imidazol-1-yl)bicyclo[1.1.1]pentan-1-yl)morpholine

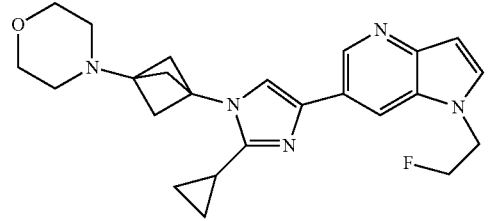 [SMILES: FCCn1ccc2ncc(-c3cn(C45CC(N6CCOCC6)(C4)C5)c(C4CC4)n3)cc21]

Step 1: 4-(3-(2-cyclopropyl-4-(1-(2-fluoroethyl)-1H-pyrrolo[3,2-b]pyridin-6-yl)-1H-imidazol-1-yl)bicyclo[1.1.1]pentan-1-yl)morpholine bis(2,2,2-trifluoroacetate)

To a solution of 4-(3-(2-cyclopropyl-4-(1H-pyrrolo[3,2-b]pyridin-6-yl)-1H-imidazol-1-yl)bicyclo[1.1.1]pentan-1-yl)morpholine bis(2,2,2-trifluoroacetate) (15 mg, 0.025 mmol) in MeCN (0.5 ml) were added K$_2$CO$_3$ (10.3 mg, 0.075 mmol) and 1-fluoro-2-iodoethane (6.49 mg, 0.037 mmol), and the resulting mixture was stirred at 80° C. for 3 h. The mixture was filtered and the filtrate was concentrated under reduced pressure. The residue was purified by reverse phase preparative HPLC (Mobile phase: A=0.1% TFA/water, B=0.1% TFA/MeCN; Gradient: B=10% to 40% in 12 min; Column: C18) to give the title compound as a white solid (8 mg, 50%). MS (ES$^+$) C$_{24}$H$_{28}$FN$_5$O requires: 421, found: 422 [M+H]$^+$. $^1$H NMR (CD$_3$OD) δ 8.87 (d, 1H, J=1.2 Hz), 8.83 (s, 1H), 8.07 (d, 1H, J=3.3 Hz), 7.85 (s, 1H), 6.85 (d, 1H, J=3.3 Hz), 4.87-4.84 (m, 1H), 4.79-4.74 (m, 2H), 4.73-4.70 (m, 1H), 3.81 (t, 4H, J=4.6 Hz), 2.80 (t, 4H, J=4.6 Hz), 2.63 (s, 6H), 2.23-2.17 (m, 1H), 1.22-1.13 (m, 4H).

Example 22

4-(3-(4-(6-amino-5-(trifluoromethoxy)pyridin-3-yl)-2-cyclopropyl-1H-imidazol-1-yl)bicyclo[1.1.1]pentan-1-yl)-1-methylpiperazin-2-one

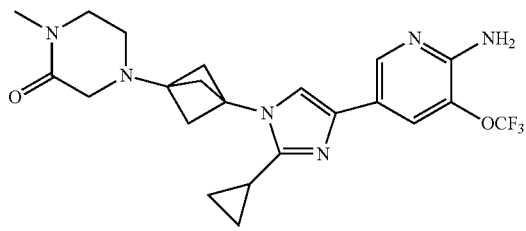 [SMILES: CN1CCN(C23CC(n4cc(-c5cnc(N)c(OC(F)(F)F)c5)nc4C4CC4)(C2)C3)CC1=O]

Step 1: methyl (3-(2-cyclopropyl-4-iodo-1H-imidazol-1-yl)bicyclo[1.1.1]pentan-1-yl)glycinate To a solution of 3-(2-cyclopropyl-4-iodo-1H-imidazol-1-yl)bicyclo[1.1.1]pentan-1-amine bis(2,2,2-trifluoroacetate) (200 mg, 0.368 mmol) in MeCN (3 ml) were added $K_2CO_3$ (254 mg, 1.84 mmol) and methyl 2-bromoacetate (84 mg, 0.55 mmol), and the resulting mixture was stirred at RT for 16 h. The mixture was filtered, and the filtrate was concentrated under reduced pressure. The residue was purified by $SiO_2$ gel chromatography (0% to 5% MeOH in DCM) to give the title compound as a colorless liquid (126 mg, 88%). MS (ES$^+$) $C_{14}H_{18}IN_3O_2$ requires: 387, found: 388 [M+H]$^+$.

Step 2: (3-(2-cyclopropyl-4-iodo-1H-imidazol-1-yl)bicyclo[1.1.1]pentan-1-yl)glycine To a solution of the product from the previous step (125 mg, 0.323 mmol) in THF (1 ml) and water (1 ml) was added LiOH (23.2 mg, 0.968 mmol), and the resulting mixture was stirred at RT for 2 h then concentrated under reduced pressure. The residue was purified by reverse phase preparative HPLC (Mobile phase: A=0.1% TFA/water, B=0.1% TFA/MeCN; Gradient: B=0% to 30% in 12 min; Column: C18) to give the title compound as a white solid (152 mg, 78% yield). MS (ES$^+$) $C_{13}H_{16}IN_3O_2$ requires: 373, found: 374 [M+H]$^+$.

Step 3: 4-(3-(2-cyclopropyl-4-iodo-1H-imidazol-1-yl)bicyclo[1.1.1]pentan-1-yl)-1-methylpiperazin-2-one To a solution of the product from the previous step (150 mg, 0.249 mmol) in DMF (1 ml) were added 2-bromo-N-methylethanamine hydrobromide (65.5 mg, 0.299 mmol), HATU (114 mg, 0.299 mmol) and DIEA (0.218 ml, 1.25 mmol) and the resulting mixture was stirred at RT for 16 h. Water (10 mL) was added, and the layers were separated. The aqueous phase was extracted with EtOAc (3×5 mL), and the combined organic layers were washed with sat. aq. NaCl, dried over $MgSO_4$, filtered and concentrated under reduced pressure. The residue was purified by $SiO_2$ gel chromatography (0% to 5% MeOH in DCM) to give the title compound as a white solid (52 mg, 51%). MS (ES$^+$) $C_{16}H_{21}IN_4O$ requires: 412, found: 413 [M+H]$^+$.

Step 4: 4-(3-(4-(6-amino-5-(trifluoromethoxy)pyridin-3-yl)-2-cyclopropyl-1H-imidazol-1-yl)bicyclo[1.1.1]pentan-1-yl)-1-methylpiperazin-2-one A degassed solution of the product from the previous step (50 mg, 0.12 mmol), 5-(4,4,5,5-tetramethyl-1,3,2-dioxaborolan-2-yl)-3-(trifluoromethoxy)pyridin-2-amine (44.3 mg, 0.146 mmol), PdCl$_2$(dppf)-CH$_2$Cl$_2$ (9.90 mg, 0.012 mmol) and 2.0 M aq. $K_2CO_3$ (0.182 ml, 0.364 mmol) in DMF (0.5 ml) was stirred at 90° C. for 2 h. The mixture was diluted with EtOAc, filtered through CELITE®, and the filtrate was concentrated under reduced pressure. The residue was purified by reverse phase preparative HPLC (Mobile phase: A=0.1% TFA/water, B=0.1% TFA/MeCN; Gradient: B=10% to 40% in 12 min; Column: C18) to give a residue. The residue was dissolved in water, and the mixture adjusted to pH=8 with sat. aq. NaHCO$_3$. Precipitate was isolated by filtration to give the title compound as a white solid (25 mg, 45% yield). MS (ES$^+$) $C_{22}H_{25}F_3N_6O_2$ requires: 462, found: 463 [M+H]$^+$. $^1$H NMR (DMSO-d$_6$) δ 8.28 (d, 1H, J=1.8 Hz), 7.69 (s, 1H), 7.46 (s, 1H), 6.29 (s, 2H), 3.33-3.30 (t, 2H, J=5.5 Hz), 3.06 (s, 2H), 2.84 (s, 3H), 2.73-2.70 (t, 2H, J=5.5 Hz), 2.35 (s, 6H), 2.04-1.98 (m, 1H), 0.93-0.85 (m, 4H).

Example 23

1-(3-(4-(6-amino-5-(trifluoromethoxy)pyridin-3-yl)-2-cyclopropyl-1H-imidazol-1-yl)bicyclo[1.1.1]pentan-1-yl)-4-methylpiperazin-2-one

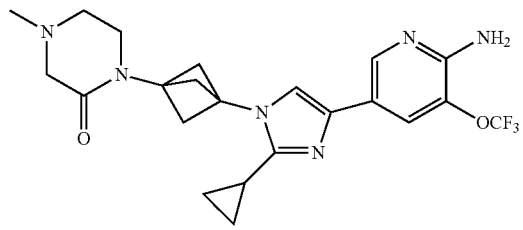 [SMILES: CN1CCN(C23CC(n4cc(-c5cnc(N)c(OC(F)(F)F)c5)nc4C4CC4)(C2)C3)C(=O)C1]

Step 1: 2-bromo-N-(3-(2-cyclopropyl-4-iodo-1H-imidazol-1-yl)bicyclo[1.1.1]pentan-1-yl)acetamide To a solution of 3-(2-cyclopropyl-4-iodo-1H-imidazol-1-yl)bicyclo[1.1.1]pentan-1-amine bis(2,2,2-trifluoroacetate) (272 mg, 0.500 mmol) in DMF (1 ml) at 0° C. were added 2-bromoacetic acid (83 mg, 0.60 mmol), HATU (228 mg, 0.600 mmol) and DIEA (0.437 ml, 2.50 mmol). The resulting mixture was stirred for 1 h, then treated with sat. aq. NH$_4$Cl (10 ml). The mixture was extracted with EtOAc (3×5 mL), and the combined organic layers were washed with sat. aq. NaCl, dried over MgSO$_4$, filtered and concentrated under reduced pressure. The residue was purified by SiO$_2$ gel chromatography (0% to 5% MeOH in DCM) to give the title compound as a colorless liquid (212 mg, 97%). MS (ES$^+$) $C_{13}H_{15}BrIN_3O$ requires: 435 and 437, found: 436 and 438 [M+H]$^+$.

Step 2: 2-((2-bromoethyl)(methyl)amino)-N-(3-(2-cyclopropyl-4-iodo-1H-imidazol-1-yl)bicyclo[1.1.1]pentan-1-yl)acetamide To a solution of the product from the previous step (210 mg, 0.482 mmol) in MeCN (2 ml) were added K$_2$CO$_3$ (333 mg, 2.41 mmol) and 2-bromo-N-methylethanamine (199 mg, 1.44 mmol) and the resulting mixture was stirred at RT for 1 h. The mixture was filtered and the filtrate was concentrated under reduced pressure. The residue was purified by SiO$_2$ gel chromatography (0% to 5% MeOH in DCM) to give the title compound as a colorless liquid (155 mg, 65%). MS (ES$^+$) C$_{16}$H$_{22}$BrIN$_4$O requires: 492, found: 493 [M+H]$^+$.

Step 3: 1-(3-(2-cyclopropyl-4-iodo-1H-imidazol-1-yl)bicyclo[1.1.1]pentan-1-yl)-4-methylpiperazin-2-one To a solution of the product from the previous step (150 mg, 0.304 mmol) in MeCN (3 ml) was added K$_2$CO$_3$ (126 mg, 0.912 mmol) and the resulting mixture was stirred at 80° C. for 2 h. The mixture was filtered and the filtrate was concentrated under reduced pressure. The residue was purified by SiO$_2$ gel chromatography (0% to 5% MeOH in DCM) to give the title compound as a white solid (25 mg, 20%). MS (ES$^+$) C$_{16}$H$_{21}$IN$_4$O requires: 412, found: 413 [M+H]$^+$.

Step 4: 1-(3-(4-(6-amino-5-(trifluoromethoxy)pyridin-3-yl)-2-cyclopropyl-1H-imidazol-1-yl)bicyclo[1.1.1]pentan-1-yl)-4-methylpiperazin-2-one A degassed solution of the product from the previous step (23 mg, 0.056 mmol), 5-(4,4,5,5-tetramethyl-1,3,2-dioxaborolan-2-yl)-3-(trifluoromethoxy)pyridin-2-amine (13.1 mg, 0.043 mmol), PdCl$_2$(dppf)-CH$_2$Cl$_2$ (2.93 mg, 3.59 μmol) and 2.0 M aq. K$_2$CO$_3$ (0.090 ml, 0.180 mmol) in DMF (0.5 ml) was stirred at 90° C. for 2 h. The mixture was diluted with EtOAc, filtered through CELITE®, and the filtrate was concentrated under reduced pressure. The residue was purified by reverse phase preparative HPLC (Mobile phase: A=0.1% TFA/water, B=0.1% TFA/MeCN; Gradient: B=10% to 40% in 12 min; Column: C18) to give a residue. The residue was dissolved in water, and the mixture was adjusted to pH=8 with sat. aq. NaHCO$_3$. Precipitate was isolated by filtration to give the title compound as a white solid (9 mg, 54%). MS (ES$^+$) C$_{22}$H$_{25}$F$_3$N$_6$O$_2$ requires: 462, found: 463 [M+H]$^+$. $^1$H NMR (CD$_3$OD) δ 8.22 (d, 1H, J=1.6 Hz), 7.78 (s, 1H), 7.33 (s, 1H), 3.45 (t, 2H, J=5.6 Hz), 3.09 (s, 2H), 2.81 (s, 6H), 2.73 (t, 2H, J=5.6 Hz), 2.35 (s, 3H), 2.05-2.00 (m, 1H), 1.03-0.97 (m, 4H).

Example 24

5-(2-cyclopropyl-1-(3-((2-methoxyethyl)(methyl)amino)bicyclo[1.1.1]pentan-1-yl)-1H-imidazol-4-yl)-3-(trifluoromethoxy)pyridin-2-amine

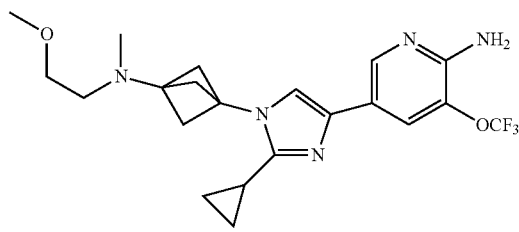 [SMILES: COCCN(C)C12CC(n3cc(-c4cnc(N)c(OC(F)(F)F)c4)nc3C3CC3)(C1)C2]

Step 1: 3-(2-cyclopropyl-4-iodo-1H-imidazol-1-yl)-N-(2-methoxyethyl)bicyclo[1.1.1]pentan-1-amine To a solution of 3-(2-cyclopropyl-4-iodo-1H-imidazol-1-yl)bicyclo[1.1.1]pentan-1-amine bis(2,2,2-trifluoroacetate) (200 mg, 0.368 mmol) in MeCN (1 ml) were added K$_2$CO$_3$ (50.9 mg, 0.368 mmol) and 1-bromo-2-methoxyethane (154 mg, 1.10 mmol), and the resulting mixture was stirred at 90° C. for 16 h. The mixture was filtered and the filtrate was concentrated under reduced pressure. The residue was purified by SiO$_2$ gel chromatography (0% to 5% MeOH in DCM) to give the title compound as a colorless liquid (30 mg, 22%). MS (ES$^+$) C$_{14}$H$_{20}$IN$_3$O requires: 373, found: 374 [M+H]$^+$.

Also isolated from this reaction mixture was the dialkylated product, 3-(2-cyclopropyl-4-iodo-1H-imidazol-1-yl)-N,N-bis(2-methoxyethyl)bicyclo[1.1.1]pentan-1-amine (56 mg, 35%). MS (ES$^+$) C$_{17}$H$_{26}$IN$_3$O$_2$ requires: 431, found: 432 [M+H]$^+$. This compound was used in the synthesis of the Example 25 compound, below.

Step 2: 3-(2-cyclopropyl-4-iodo-1H-imidazol-1-yl)-N-(2-methoxyethyl)-N-methylbicyclo[1.1.1]pentan-1-amine To a solution of the product from the previous step (20 mg, 0.054 mmol) in DCM (1 ml) was added formalin (0.015 ml, 0.201 mmol), and the resulting mixture was stirred at RT for 10 min. NaBH(OAc)$_3$ (114 mg, 0.536 mmol) was added and the mixture was stirred at RT for 1 h. Sat. aq. NaHCO$_3$ (5 mL) was added, and the layers were separated. The aqueous layer was extracted with DCM (3×5 mL), and the combined organic layers were washed with sat. aq. NaCl, dried over MgSO$_4$, filtered and concentrated under reduced pressure. The residue was purified by SiO$_2$ gel chromatography (0% to 5% MeOH in DCM) to give the title compound as a white solid (16 mg, 77%). MS (ES$^+$) C$_{15}$H$_{22}$IN$_3$O requires: 387, found: 388 [M+H]$^+$.

Step 3: 5-(2-cyclopropyl-1-(3-((2-methoxyethyl)(methyl)amino)bicyclo[1.1.1]pentan-1-yl)-1H-imidazol-4-yl)-3-(trifluoromethoxy)pyridin-2-amine A degassed solution of the product from the previous step (15 mg. 0.039 mmol), 5-(4,4,5,5-tetramethyl-1,3,2-dioxaborolan-2-yl)-3-(trifluoromethoxy)pyridin-2-amine (14 mg, 0.046 mmol), PdCl$_2$(dppf)-CH$_2$Cl$_2$ (3.16 mg, 3.87 μmol) and 2.0 M aq. K$_2$CO$_3$ (0.058 ml, 0.116 mmol) in DMF (0.5 ml) was stirred at 90° C. for 2 h. The mixture was diluted with EtOAc, filtered through CELITE®, and the filtrate was concentrated under reduced pressure. The residue was purified by reverse phase preparative HPLC (Mobile phase: A=0.1% TFA/water, B=0.1% TFA/MeCN; Gradient: B=10% to 40% in 12 min; Column: C18) to give a residue. The residue was dissolved in water, and the mixture was adjusted to pH=8 with sat. aq. NaHCO$_3$. Precipitate was isolated by filtration to give the title compound as a white solid (8 mg, 47%). MS (ES$^+$) C$_{21}$H$_{26}$F$_3$N$_5$O$_2$ requires: 437, found: 438 [M+H]$^+$. $^1$H NMR (DMSO-d$_6$) δ 8.28 (d, 1H, J=1.7 Hz), 7.69 (s, 1H), 7.45 (s, 1H), 6.32 (s, 2H), 3.42 (t, 2H, 6.0 Hz), 3.25 (s, 3H), 2.57 (t, 2H, J=6.0 Hz), 2.31 (s, 6H), 2.23 (s, 3H), 2.04-1.99 (m, 1H), 0.93-0.84 (m, 4H).

Example 25

5-(1-(3-(bis(2-methoxyethyl)amino)bicyclo[1.1.1]pentan-1-yl)-2-cyclopropyl-1H-imidazol-4-yl)-3-(trifluoromethoxy)pyridin-2-amine

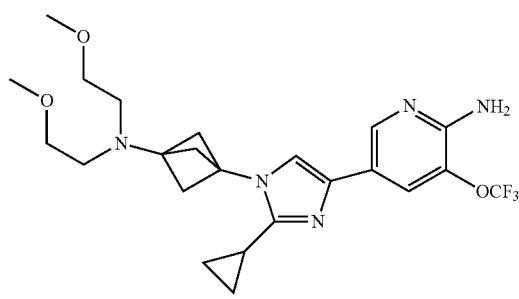 [SMILES: COCCN(CCOC)C12CC(n3cc(-c4cnc(N)c(OC(F)(F)F)c4)nc3C3CC3)(C1)C2]

Step 1: 3-(2-cyclopropyl-4-iodo-1H-imidazol-1-yl)-N,N-bis(2-methoxyethyl)bicyclo[1.1.1]-pentan-1-amine This compound was obtained in Step 1 of the synthesis of the Example 24 compound, as described above.

Step 2: 5-(1-(3-(bis(2-methoxyethyl)amino)bicyclo[1.1.1]pentan-1-yl)-2-cyclopropyl-1H-imidazol-4-yl)-3-(trifluoromethoxy)pyridin-2-amine A degassed solution of 3-(2-cyclopropyl-4-iodo-1H-imidazol-1-yl)-N,N-bis(2-methoxyethyl)bicyclo[1.1.1]pentan-1-amine (40 mg, 0.093 mmol), 5-(4,4,5,5-tetramethyl-1,3,2-dioxaborolan-2-yl)-3-(trifluoromethoxy)pyridin-2-amine (33.8 mg, 0.111 mmol), PdCl$_2$(dppf)-CH$_2$Cl$_2$ (7.57 mg, 9.27 µmol) and 2.0 M aq. K$_2$CO$_3$ (0.139 ml, 0.278 mmol) in DMF (1 ml) was stirred at 90° C. for 2 h. The mixture was diluted with EtOAc, filtered through CELITE®, and the filtrate was concentrated under reduced pressure. The residue was purified by reverse phase preparative HPLC (Mobile phase: A=0.1% TFA/water, B=0.1% TFA/MeCN; Gradient: B=10% to 40% in 12 min; Column: C18) to give a residue. The residue was dissolved in water, and the mixture adjusted to pH=8 with sat. aq. NaHCO$_3$. Precipitate was isolated by filtration to give the title compound as a white solid (22 mg, 49%). MS (ES$^+$) C$_{23}$H$_{30}$F$_3$N$_5$O$_3$ requires: 481, found: 482 [M+H]$^+$. $^1$H NMR (DMSO-d$_6$) δ 8.28 (d, 1H, J=1.6 Hz), 7.68 (s, 1H), 7.45 (s, 1H), 6.32 (s, 2H), 3.37 (t, 4H, J=6.3 Hz), 3.25 (s, 6H), 2.74 (t, 4H, J=6.3 Hz), 2.34 (s, 6H), 2.05-2.00 (m, 1H), 0.93-0.84 (m, 4H).

Example 26

1-(3-(4-(6-amino-5-(trifluoromethoxy)pyridin-3-yl)-2-cyclopropyl-1H-imidazol-1-yl)bicyclo[1.1.1]pentan-1-yl)piperidin-4-ol

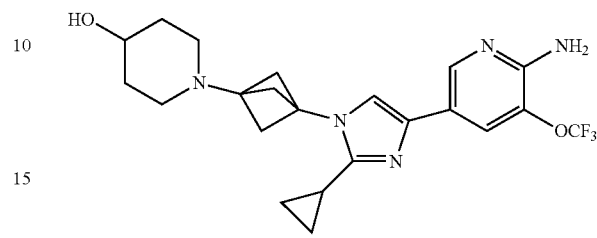

Step 1: 1-(3-(2-cyclopropyl-4-iodo-1H-imidazol-1-yl)bicyclo[1.1.1]pentan-1-yl)piperidin-4-one To a solution of 3-(2-cyclopropyl-4-iodo-1H-imidazol-1-yl)bicyclo[1.1.1]pentan-1-amine bis(2,2,2-trifluoroacetate) (200 mg, 0.368 mmol) in MeCN (3 ml) were added K$_2$CO$_3$ (254 mg, 1.84 mmol) and 1,5-dibromopentan-3-one (135 mg, 0.552 mmol) and the resulting mixture was stirred at 75° C. for 16 h. The mixture was filtered through a Büchner funnel, and the filtrate was concentrated under reduced pressure. The residue was purified by SiO$_2$ gel chromatography (0% to 5% MeOH in DCM) to give the title compound as a colorless liquid (82 mg, 56%). MS (ES$^+$) C$_{16}$H$_{20}$IN$_3$O requires: 397, found: 398 [M+H]$^+$.

Step 2: 1-(3-(2-cyclopropyl-4-iodo-1H-imidazol-1-yl)bicyclo[1.1.1]pentan-1-yl)piperidin-4-ol To a solution of the product from the previous step (300 mg, 0.755 mmol) in MeOH (5 ml) was added NaBH$_4$, (86 mg, 2.3 mmol), and the resulting mixture was stirred at RT for 0.5 h. Sat. aq. NaHCO$_3$ (1 mL) was added, and the mixture was concentrated under reduced pressure. Water (10 mL) was added, and the mixture was extracted with EtOAc (3×10 mL). The combined organic layers were washed with sat. aq. NaCl, dried over MgSO$_4$, filtered and concentrated under reduced pressure. The residue was purified by SiO$_2$ gel chromatography (0% to 10% MeOH in DCM) to give the title compound as a white foamy solid (212 mg, 70%). MS (ES$^+$) C$_{16}$H$_{22}$IN$_3$O. requires: 399, found: 400 [M+H]$^+$.

Step 3: 1-(3-(4-(6-amino-5-(trifluoromethoxy)pyridin-3-yl)-2-cyclopropyl-1H-imidazol-1-yl)bicyclo[1.1.1]pentan-1-yl)piperidin-4-ol A degassed solution of the product from the previous step (40 mg, 0.10 mmol), 5-(4,4,5,5-tetramethyl-1,3,2-dioxaborolan-2-yl)-3-(trifluoromethoxy)pyridin-2-amine (36.6 mg, 0.120 mmol), PdCl$_2$(dppf)-CH$_2$Cl$_2$ (8.18 mg, 10.0 µmol) and 2.0 M aq. K$_2$CO$_3$ (0.150 ml, 0.301 mmol) in DMF (0.5 ml) was stirred at 90° C. for 2 h. The mixture was diluted with EtOAc, filtered through CELITE®, and the filtrate was concentrated under reduced pressure. The residue was purified by reverse phase preparative HPLC (Mobile phase: A=0.1% TFA/water, B=0.1% TFA/MeCN; Gradient: B=0% to 30% in 12 min; Column: C18) to give a residue. The residue was dissolved in water, and the mixture was adjusted to pH=8 with sat. aq. NaHCO$_3$. Precipitate was isolated by filtration to give the title compound as a white solid (31 mg, 69%). MS (ES+) $C_{22}H_{26}F_3N_5O_2$ requires: 449, found: 450 [M+H]+. 1H NMR (DMSO-$d_6$) δ 8.28 (s, 1H), 7.69 (s, 1H), 7.46 (s, 1H), 6.32 (s, 2H), 4.60 (s, 1H), 3.50-3.42 (m, 1H), 2.74-2.68 (m, 2H), 2.30 (s, 6H), 2.18-2.10 (m, 2H), 2.05-1.97 (m, 1H), 1.77-1.70 (m, 2H), 1.44-1.35 (m, 2H), 0.94-0.83 (m, 4H).

Example 27

5-(2-cyclopropyl-1-(3-(oxazol-5-yl)bicyclo[1.1.1]pentan-1-yl)-1H-imidazol-4-yl)-3-(trifluoromethoxy)pyridin-2-amine

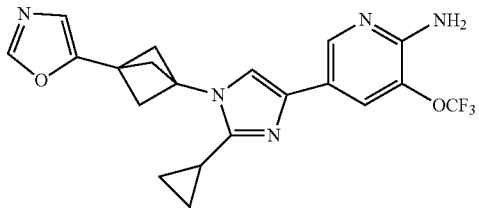 [SMILES: Nc1ncc(-c2cn(C34CC(c5cnco5)(C3)C4)c(C3CC3)n2)cc1OC(F)(F)F]

Step 1: methyl 3-(2-cyclopropyl-1H-imidazol-1-yl)bicyclo[1.1.1]pentane-1-carboxylate To a solution of cyclopropanecarbaldehyde (70.0 mg, 0.999 mmol) in MeOH (5 ml) were added methyl 3-aminobicyclo[1.1.1]pentane-1-carboxylate (141 mg, 0.999 mmol), NH4OAc (77 mg, 0.10 mmol) and 40% aq. glyoxal (145 mg, 0.999 mmol), and the mixture was stirred at RT for 16 h then concentrated under reduced pressure. The residue was purified by SiO2 gel chromatography (0% to 5% MeOH in DCM) to give the title compound as a white solid (93 mg, 40%). MS (ES+) $C_{13}H_{16}N_2O_2$ requires: 232, found: 233 [M+H]+.

Step 2: methyl 3-(2-cyclopropyl-4-iodo-1H-imidazol-1-yl)bicyclo[1.1.1]pentane-1-carboxylate To a solution of the product from the previous step (92 mg, 0.40 mmol) in DMF (2 ml) was added NIS (267 mg, 1.19 mmol) and the resulting mixture was stirred at 60° C. for 2 h. Sat. aq. Na2S2O3 (1 ml) and water (10 ml) were added, and the mixture was extracted with EtOAc (3×5 mL). The combined organic layers were washed with sat. aq. NaCl, dried over MgSO4, filtered and concentrated under reduced pressure. The residue was purified by SiO2 gel chromatography (0% to 40% EtOAc in hexanes) to give a pale yellow liquid, which was dissolved in THF (2 mL) and cooled to −78° C. To the mixture was added a 2.0 M iPrMgCl in THF solution (200 μL, 0.400 mmol) and the resulting mixture was stirred at −78° C. for 1 h. Sat. aq. NH4Cl (10 mL) was added, and the layers were separated. The aqueous layer was extracted with EtOAc (3×5 mL), and the combined organic layers were washed with sat. aq. NaCl, dried over MgSO4, filtered and concentrated under reduced pressure. The residue was purified by SiO2 gel chromatography (0% to 50% EtOAc in hexanes) to give the title compound as a white solid (58 mg, 41%). MS (ES+) $C_{13}H_{15}IN_2O_2$ requires: 358, found: 359 [M+H]+.

Step 3: 5-(3-(2-cyclopropyl-4-iodo-1H-imidazol-1-yl)bicyclo[1.1.1]pentan-1-yl)oxazole To a solution of the product from the previous step (58 mg, 0.16 mmol) in DCM (2 ml) at −78° C. was added DIBAL-H (46.1 mg, 0.324 mmol) and the resulting mixture was stirred at −78° C. for 1 h. Sat. aq. NH4Cl (10 mL) was added, and the mixture was extracted with EtOAc (3×5 mL). The combined organic layers were washed with sat. aq. NaCl, dried over MgSO4, filtered and concentrated under reduced pressure to give crude 3-(2-cyclopropyl-4-iodo-1H-imidazol-1-yl)bicyclo[1.1.1]pentane-1-carbaldehyde (MS (ES+) $C_{12}H_{13}IN_2O$ requires: 328, found: 329 [M+H]+), which was dissolved in MeOH (2 mL). To the mixture were added K2CO3 (67.0 mg, 0.485 mmol) and toluenesulfonylmethyl isocyanide (37.8 mg, 0.194 mmol), and the resulting mixture was stirred at 60° C. for 16 h then concentrated under reduced pressure. The residue was purified by SiO2 gel chromatography (0% to 5% MeOH in DCM) to give the title compound as a white solid (26 mg, 44%). MS (ES+) $C_{14}H_{14}IN_3O$ requires: 367, found: 368 [M+H]+.

Step 4: 5-(2-cyclopropyl-1-(3-(oxazol-5-yl)bicyclo[1.1.1]pentan-1-yl)-1H-imidazol-4-yl)-3-(trifluoromethoxy)pyridin-2-amine A degassed solution of the product from the previous step (25 mg, 0.068 mmol), 5-(4,4,5,5-tetramethyl-1,3,2-dioxaborolan-2-yl)-3-(trifluoromethoxy)pyridin-2-amine (24.8 mg, 0.082 mmol), PdCl2(dppf)-CH2Cl2 (5.56 mg, 6.81 μmol) and 2.0 M aq. K2CO3 (0.102 ml, 0.204 mmol) in DMF (0.5 ml) was stirred at 90° C. for 2 h. The mixture was diluted with EtOAc, filtered through CELITE®, and the filtrate was concentrated under reduced pressure. The residue was purified by reverse phase preparative HPLC (Mobile phase: A=0.1% TFA/water, B=0.1% TFA/MeCN; Gradient: B=10% to 40% in 12 min; Column: C18) to give a residue. The residue was dissolved in water, and the mixture was adjusted to pH=8 with sat. aq. NaHCO3. The precipitate was isolated by filtration to give the title compound as a white solid (15 mg, 53%). MS (ES+) $C_{20}H_{18}F_3N_5O_2$ requires: 417, found: 418 [M+H]+. 1H NMR (DMSO-$d_6$) δ 8.33 (s, 1H), 8.30 (d, 1H, J=1.9 Hz), 7.70 (s, 1H), 7.54 (s, 1H), 7.09 (s, 1H), 6.33 (s, 2H), 2.70 (s, 6H), 2.10-2.04 (m, 1H), 0.95-0.87 (m, 4H).

Example 28

4-(3-(2-isopropyl-4-(1-(1-(pyridin-2-yl)ethyl)-1H-pyrrolo[3,2-b]pyridin-6-yl)-1H-imidazol-1-yl)bicyclo[1.1.1]pentan-1-yl)morpholine

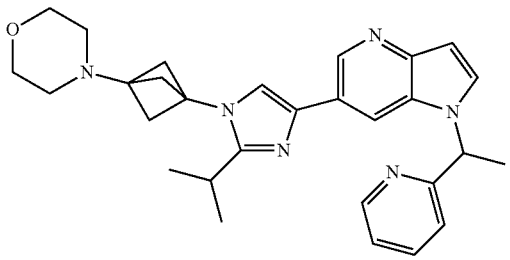 [SMILES: CC(C)c1nc(-c2cnc3ccn(C(C)c4ccccn4)c3c2)cn1C12CC(N3CCOCC3)(C1)C2]

Step 1: tert-butyl 3-(2-isopropyl-1H-imidazol-1-yl)bicyclo[1.1.1]pentan-1-yl carbamate To a solution of tert-butyl 3-aminobicyclo[1.1.1]pentan-1-yl carbamate (2.0 g, 10 mmol) and isobutyraldehyde (727 mg, 10.1 mmol) in MeOH (20 mL) were added NH$_4$OAc (777 mg, 10.1 mmol) and 40% aq. glyoxal (1.46 g, 10.1 mmol). The mixture was stirred at RT overnight, then concentrated and diluted with DCM. The resulting mixture was sequentially washed with sat. aq. NaHCO$_3$ and sat. aq. NaCl, dried over MgSO$_4$, filtered and concentrated to give the title compound as a brown oil (2.1 g, 72%), which was used without further purification. MS (ES$^+$) C$_{16}$H$_{25}$N$_3$O$_2$ requires: 291, found: 292 [M+H]$^+$.

Step 2: tert-butyl 3-(4,5-diiodo-2-isopropyl-1H-imidazol-1-yl)bicyclo[1.1.1]pentan-1-yl carbamate To a solution of the product from the previous step (2.0 g, 6.6 mmol) in DMF (20 mL) was added NIS (4.64 g, 20.6 mmol), and the mixture was stirred at 50° C. for 3 h. The mixture was poured into water and extracted with EtOAc (2×45 mL). The combined organic layers were washed with sat. aq. NaCl (4×25 mL), dried over MgSO$_4$, filtered and concentrated under reduced pressure. The residue was purified by SiO$_2$ gel chromatography (0% to 25% EtOAc in petroleum ether) to give the title compound as a yellow solid (1.81 g, 50%). MS (ES$^+$) C$_{16}$H$_{23}$I$_2$N$_3$O$_2$ requires: 543, found: 544 [M+H]$^+$.

Step 3: tert-butyl 3-(4-iodo-2-isopropyl-1H-imidazol-1-yl)bicyclo[1.1.1]pentan-1-ylcarbamate To a solution of the product from the previous step (1.81 g, 3.33 mmol) in THF (20 mL) at −78° C. was added a 2.0 M EtMgCl in Et$_2$O solution (3.33 mL, 6.66 mmol), and the mixture was stirred at −78° C. for 1 h. Sat. aq. NH$_4$Cl was added, and the mixture was extracted with EtOAc (3×80 mL). The combined organic layers were washed with sat. aq. NaCl (50 mL), dried over Na$_2$SO$_4$, filtered and concentrated under reduced pressure to give the title compound as a yellow solid (900 mg, 65%). MS (ES$^+$) C$_{16}$H$_{24}$IN$_3$O$_2$ requires: 417, found: 418 [M+H]$^+$.

Step 4: 3-(4-iodo-2-isopropyl-1H-imidazol-1-yl)bicyclo[1.1.1]pentan-1-amine

To a solution of the product from the previous step (400 mg, 0.959 mmol) in DCM (10 mL) was added TFA (2 mL), and the mixture was stirred at RT overnight then concentrated under reduced pressure. The residue was diluted with sat. aq. NaHCO$_3$ and extracted with EtOAc. The organic layer was dried over MgSO$_4$, filtered and concentrated under reduced pressure to give the title compound as a yellow solid (200 mg, 65%). MS (ES$^+$) C$_{11}$H$_{16}$IN$_3$ requires: 317, found: 318 [M+H]$^+$.

Step 5: 4-(3-(4-iodo-2-isopropyl-1H-imidazol-1-yl)bicyclo[1.1.1]pentan-1-yl)morpholine To a solution of the product from the previous step (200 mg, 0.63 mmol) in MeCN (10 mL) were added 1-bromo-2-(2-bromoethoxy)ethane (291 mg, 1.26 mmol) and K$_2$CO$_3$ (434 mg, 3.15 mmol), and the mixture was stirred at 90° C. overnight then concentrated under reduced pressure. The residue was diluted with sat. aq. NaHCO$_3$ and extracted with EtOAc. The organic layer was dried over MgSO$_4$, filtered and concentrated under reduced pressure. The residue was purified by SiO$_2$ gel chromatography (0% to 100% EtOAc in petroleum ether) to give the title compound (100 mg, 41%). MS (ES$^+$) C$_{15}$H$_{22}$IN$_3$O requires: 387, found: 388 [M+H]$^+$.

Step 6: 4-(3-(2-isopropyl-4-(1-(1-(pyridin-2-yl)ethyl)-1H-pyrrolo[3,2-b]pyridin-6-yl)-1H-imidazol-1-yl)bicyclo[1.1.1]pentan-1-yl)morpholine A mixture of the product from the previous step, 1-(1-(pyridin-2-yl)ethyl)-6-(4,4,5,5-tetramethyl-1,3,2-dioxaborolan-2-yl)-1H-pyrrolo[3,2-b]pyridine (80 mg, 0.23 mmol), 2.0 M aq. K$_2$CO$_3$ (1.0 mL, 2.0 mmol) and Pd(dppf)Cl$_2$ (19 mg, 0.02 mmol) in DMF (2 mL) was degassed and purged with N$_2$, stirred at 90° C. for 30 min., then concentrated under reduced pressure. The residue was purified by reverse phase preparative HPLC (Mobile phase: A=10 mM ammonium bicarbonate/water, B=MeCN; Gradient: B=60% to 95% in 18 min; Column: C18) to give the title compound (15 mg, 19%). MS (ES$^+$) C$_{29}$H$_{34}$N$_6$O requires: 482, found: 483 [M+H]$^+$. $^1$H NMR (500 MHz, CDCl$_3$) δ 8.74 (d, J=1.7 Hz, 1H), 8.61 (d, J=4.0 Hz, 1H), 8.05 (s, 1H), 7.53 (ddd, J=27.6, 19.1, 11.6 Hz, 2H), 7.21-7.11 (m, 1H), 7.05 (s, 1H), 6.79-6.77 (m, 2H), 5.84 (q, J=7.2 Hz, 1H), 3.94-3.56 (m, 4H), 3.23-2.99 (m, 1H), 2.75-2.41 (m, 4H), 2.36 (s, 6H), 2.00 (d, J=7.1 Hz, 3H), 1.37 (d, J=6.8 Hz, 6H).

The following compounds were prepared using methods generally described above. (Proc #=procedure from Example # was followed for preparation)

TABLE 1

Additional Examples

| Ex # | Name | Structure | Formula; MS | Proc # |
|---|---|---|---|---|
| 29 | 1-(4-(6-amino-5-(trifluoromethoxy)-pyridin-3-yl)-1-(3-morpholinobicyclo-[1.1.1]pentan-1-yl)-1H-imidazol-2-yl)cyclopropane-1-carbonitrile | 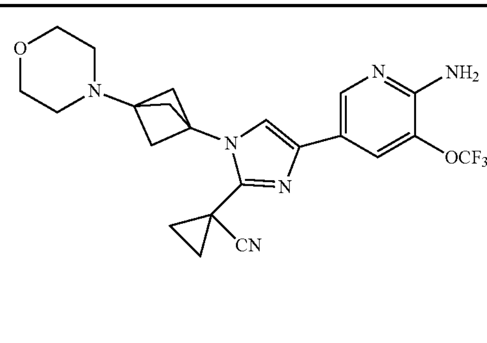 | C$_{22}$H$_{23}$F$_3$N$_6$O$_2$ Calc: 460 Obsd: 461 | 1 |

TABLE 1-continued

Additional Examples

| Ex # | Name | Structure | Formula; MS | Proc # |
|---|---|---|---|---|
| 30 | 5-(1-(3-morpholino-bicyclo[1.1.1]pentan-1-yl)-2-(tetrahydrofuran-3-yl)-1H-imidazol-4-yl)-3-(trifluoro-methoxy)pyridin-2-amine | 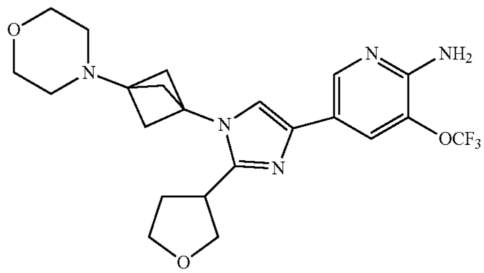 [SMILES: Nc1ncc(-c2cn(C34CC(N5CCOCC5)(C3)C4)c(C3CCOC3)n2)cc1OC(F)(F)F] | $C_{22}H_{26}F_3N_5O_3$ Calc: 465 Obsd: 466 | 1 |
| 31 | 5-(1-(3-morpholino-bicyclo[1.1.1]pentan-1-yl)-2-(oxetan-3-yl)-1H-imidazol-4-yl)-3-(trifluoromethoxy)-pyridin-2-amine | 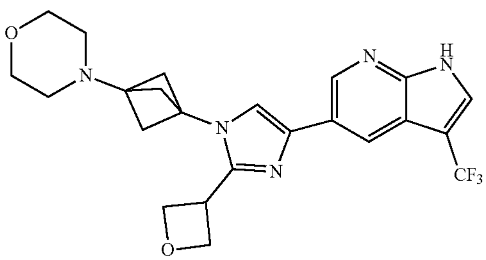 [SMILES: FC(F)(F)c1c[nH]c2ncc(-c3cn(C45CC(N6CCOCC6)(C4)C5)c(C4COC4)n3)cc12] | $C_{21}H_{24}F_3N_5O_3$ Calc: 451 Obsd: 452 | 1 |
| 32 | 5-(1-(3-morpholino-bicyclo[1.1.1]pentan-1-yl)-2-(tetrahydrofuran-2-yl)-1H-imidazol-4-yl)-3-(trifluoro-methoxy)pyridin-2-amine | 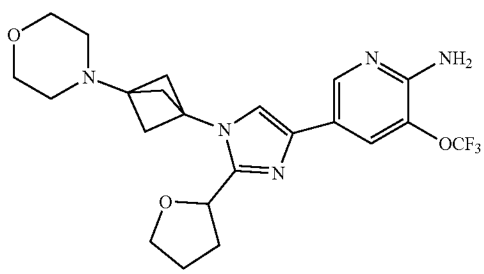 [SMILES: Nc1ncc(-c2cn(C34CC(N5CCOCC5)(C3)C4)c(C3CCCO3)n2)cc1OC(F)(F)F] | $C_{22}H_{26}F_3N_5O_3$ Calc: 465 Obsd: 466 | 1 |
| 33 | (S)-1-(4-(6-amino-5-(trifluoromethyl)-pyridin-3-yl)-1-(bicyclo[1.1.1]pentan-1-yl)-1H-imidazol-2-yl)ethan-1-ol | 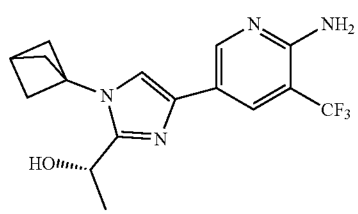 [SMILES: C[C@H](O)c1nc(-c2cnc(N)c(C(F)(F)F)c2)cn1C12CC(C1)C2] | $C_{16}H_{17}F_3N_4O$ Calc: 338 Obsd: 339 | 1 |
| 34 | 5-(2-(cyclopropyl-methyl)-1-(3-morpho-linobicyclo[1.1.1]-pentan-1-yl)-1H-imidazol-4-yl)-3-(tri-fluoromethoxy)pyridin-2-amine | 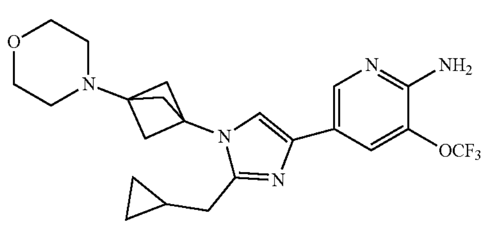 [SMILES: Nc1ncc(-c2cn(C34CC(N5CCOCC5)(C3)C4)c(CC3CC3)n2)cc1OC(F)(F)F] | $C_{22}H_{26}F_3N_5O_2$ Calc: 449 Obsd: 450 | 1 |
| 35 | 5-(2-(cyclopropyl-methyl)-1-(3-morpho-linobicyclo[1.1.1]-pentan-1-yl)-1H-imidazol-4-yl)-3-(trifluoromethyl)-pyridin-2-amine | 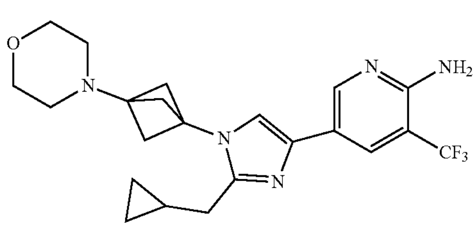 [SMILES: Nc1ncc(-c2cn(C34CC(N5CCOCC5)(C3)C4)c(CC3CC3)n2)cc1C(F)(F)F] | $C_{22}H_{26}F_3N_5O$ Calc: 433 Obsd: 434 | 1 |

TABLE 1-continued

Additional Examples

| Ex # | Name | Structure | Formula; MS | Proc # |
|---|---|---|---|---|
| 36 | 5-(2-(cyclopropyl-methyl)-1-(3-morpholinobicyclo[1.1.1]pentan-1-yl)-1H-imidazol-4-yl)-3-(difluoromethoxy)pyridin-2-amine | 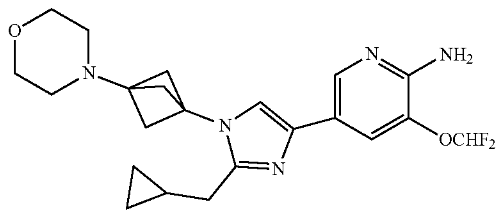 [SMILES: Nc1ncc(-c2cn(C34CC(N5CCOCC5)(C3)C4)c(CC3CC3)n2)cc1OC(F)F] | $C_{22}H_{27}F_2N_5O_2$ Calc: 431 Obsd: 432 | 1 |
| 37 | 5-(2-cyclopropyl-1-(3-morpholinobicyclo[1.1.1]pentan-1-yl)-1H-imidazol-4-yl)-3-(difluoromethoxy)-pyridin-2-amine | 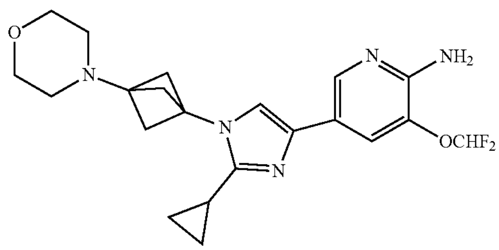 [SMILES: Nc1ncc(-c2cn(C34CC(N5CCOCC5)(C3)C4)c(C3CC3)n2)cc1OC(F)F] | $C_{21}H_{25}F_2N_5O_2$ Calc: 417 Obsd: 418 | 1 |
| 38 | 3-(difluoromethoxy)-5-(2-isopropyl-1-(3-morpholinobicyclo-[1.1.1]pentan-1-yl)-1H-imidazol-4-yl)pyridin-2-amine | 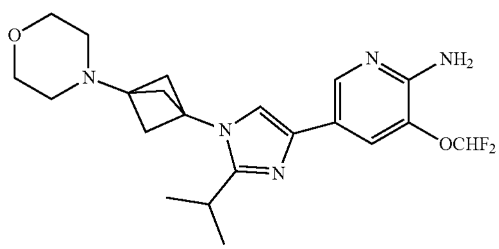 [SMILES: CC(C)c1nc(-c2cnc(N)c(OC(F)F)c2)cn1C12CC(N3CCOCC3)(C1)C2] | $C_{21}H_{27}F_2N_5O_2$ Calc: 419 Obsd: 420 | 1 |
| 39 | 5-(1-(3-morpholino-bicyclo[1.1.1]pentan-1-yl)-2-neopentyl-1H-imidazol-4-yl)-3-(trifluoromethoxy)pyridin-2-amine | 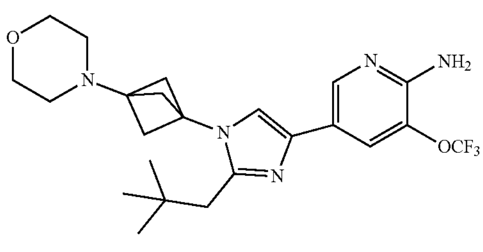 [SMILES: CC(C)(C)Cc1nc(-c2cnc(N)c(OC(F)(F)F)c2)cn1C12CC(N3CCOCC3)(C1)C2] | $C_{23}H_{30}F_3N_5O_2$ Calc: 465 Obsd: 466 | 1 |
| 40 | 5-(1-(3-morpholino-bicyclo[1.1.1]pentan-1-yl)-2-neopentyl-1H-imidazol-4-yl)-3-(trifluoromethyl)pyridin-2-amine | 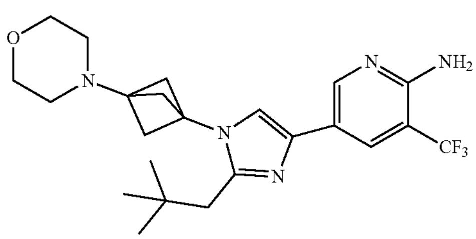 [SMILES: CC(C)(C)Cc1nc(-c2cnc(N)c(C(F)(F)F)c2)cn1C12CC(N3CCOCC3)(C1)C2] | $C_{23}H_{30}F_3N_5O$ Calc: 449 Obsd: 450 | 1 |
| 41 | 3-(difluoromethoxy)-5-(1-(3-morpholino-bicyclo[1.1.1]pentan-1-yl)-2-neopentyl-1H-imidazol-4-yl)pyridin-2-amine | 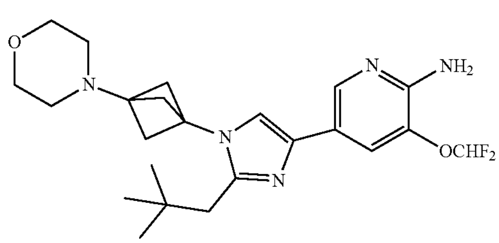 [SMILES: CC(C)(C)Cc1nc(-c2cnc(N)c(OC(F)F)c2)cn1C12CC(N3CCOCC3)(C1)C2] | $C_{23}H_{31}F_2N_5O_2$ Calc: 447 Obsd: 448 | 1 |

TABLE 1-continued

Additional Examples

| Ex # | Name | Structure | Formula; MS | Proc # |
|---|---|---|---|---|
| 42 | 5-(2-(cyclopropyl-methyl)-1-(3-(4-methylpiperazin-1-yl)-bicyclo[1.1.1]pentan-1-yl)-1H-imidazol-4-yl)-3-(trifluoromethyl)-pyridin-2-amine | 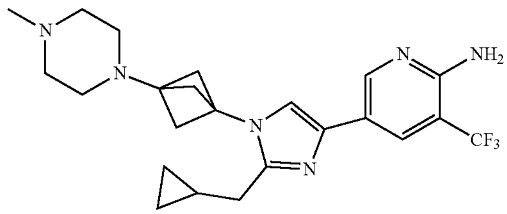 [SMILES: CN1CCN(C23CC(n4cc(-c5cnc(N)c(C(F)(F)F)c5)nc4CC4CC4)(C2)C3)CC1] | $C_{23}H_{29}F_3N_6$ Calc: 446 Obsd: 447 | 1 |
| 43 | 5-(2-cyclobutyl-1-(3-morpholinobicyclo-[1.1.1]pentan-1-yl)-1H-imidazol-4-yl)-3-(trifluoromethoxy)-pyridin-2-amine | 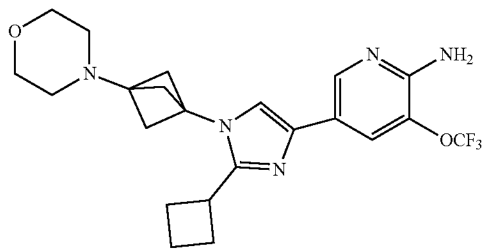 [SMILES: Nc1ncc(-c2cn(C34CC(N5CCOCC5)(C3)C4)c(C3CCC3)n2)cc1OC(F)(F)F] | $C_{22}H_{26}F_3N_5O_2$ Calc: 449 Obsd: 450 | 1 |
| 44 | 5-(2-cyclopentyl-1-(3-morpholinobicyclo-[1.1.1]pentan-1-yl)-1H-imidazol-4-yl)-3-(trifluoromethoxy)-pyridin-2-amine | 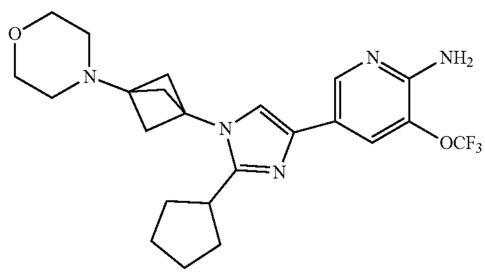 [SMILES: Nc1ncc(-c2cn(C34CC(N5CCOCC5)(C3)C4)c(C3CCCC3)n2)cc1OC(F)(F)F] | $C_{23}H_{28}F_3N_5O_2$ Calc: 463 Obsd: 464 | 1 |
| 45 | 5-(2-isobutyl-1-(3-morpholinobicyclo-[1.1.1]pentan-1-yl)-1H-imidazol-4-yl)-3-(trifluoromethoxy)-pyridin-2-amine | 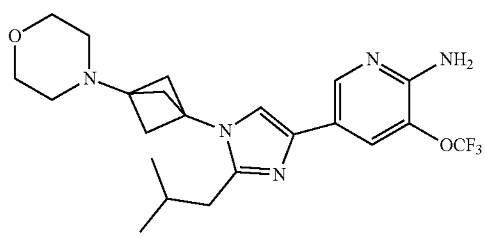 [SMILES: CC(C)Cc1nc(-c2cnc(N)c(OC(F)(F)F)c2)cn1C12CC(N3CCOCC3)(C1)C2] | $C_{22}H_{28}F_3N_5O_2$ Calc: 451 Obsd: 452 | 1 |
| 46 | 3-(difluoromethoxy)-5-(2-isobutyl-1-(3-morpholinobicyclo-[1.1.1]pentan-1-yl)-1H-imidazol-4-yl)pyridin-2-amine | 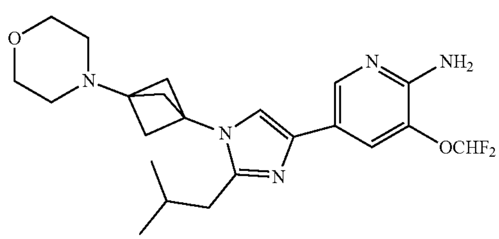 [SMILES: CC(C)Cc1nc(-c2cnc(N)c(OC(F)F)c2)cn1C12CC(N3CCOCC3)(C1)C2] | $C_{22}H_{29}F_2N_5O_2$ Calc: 433 Obsd: 434 | 1 |
| 47 | 5-(2-isobutyl-1-(3-morpholinobicyclo-[1.1.1]pentan-1-yl)-1H-imidazol-4-yl)-3-(trifluoromethyl)-pyridin-2-amine | 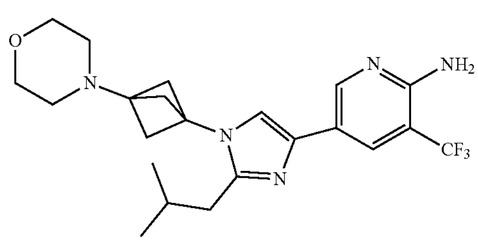 [SMILES: CC(C)Cc1nc(-c2cnc(N)c(C(F)(F)F)c2)cn1C12CC(N3CCOCC3)(C1)C2] | $C_{22}H_{28}F_3N_5O$ Calc: 435 Obsd: 436 | 1 |

TABLE 1-continued

Additional Examples

| Ex # | Name | Structure | Formula; MS | Proc # |
|---|---|---|---|---|
| 48 | 5-(1-(3-morpholino-bicyclo[1.1.1]pentan-1-yl)-2-(2,2,2-trifluoro-ethyl)-1H-imidazol-4-yl)-3-(trifluoro-methoxy)pyridin-2-amine | 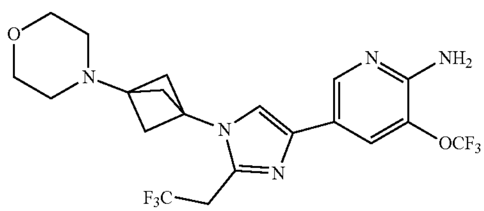 [SMILES: Nc1ncc(-c2cn(C34CC(N5CCOCC5)(C3)C4)c(CC(F)(F)F)n2)cc1OC(F)(F)F] | $C_{20}H_{21}F_6N_5O_2$ Calc: 477 Obsd: 478 | 1 |
| 49 | 5-(2-(sec-butyl)-1-(3-morpholinobicyclo-[1.1.1]pentan-1-yl)-1H-imidazol-4-yl)-3-(tri-fluoromethoxy)pyridin-2-amine | 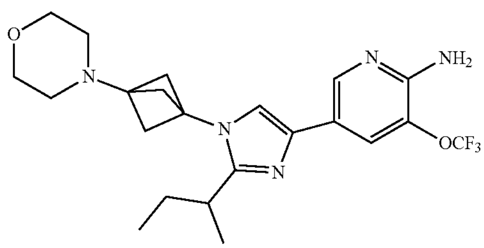 [SMILES: CCC(C)c1nc(-c2cnc(N)c(OC(F)(F)F)c2)cn1C12CC(N3CCOCC3)(C1)C2] | $C_{22}H_{28}F_3N_5O_2$ Calc: 451 Obsd: 452 | 1 |
| 50 | 5-(2-(sec-butyl)-1-(3-morpholinobicyclo-[1.1.1]pentan-1-yl)-1H-imidazol-4-yl)-3-(tri-fluoromethyl)pyridin-2-amine | 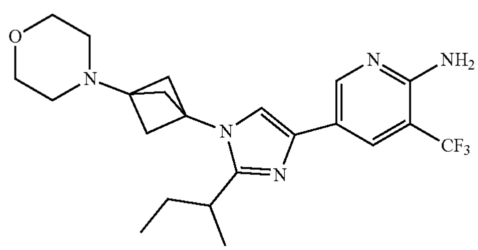 [SMILES: CCC(C)c1nc(-c2cnc(N)c(C(F)(F)F)c2)cn1C12CC(N3CCOCC3)(C1)C2] | $C_{22}H_{28}F_3N_5O$ Calc: 435 Obsd: 436 | 1 |
| 51 | 5-(2-(sec-butyl)-1-(3-morpholinobicyclo-[1.1.1]pentan-1-yl)-1H-imidazol-4-yl)-3-(di-fluoromethoxy)pyridin-2-amine | 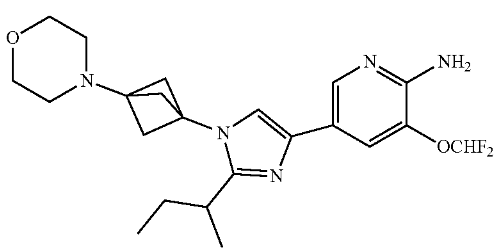 [SMILES: CCC(C)c1nc(-c2cnc(N)c(OC(F)F)c2)cn1C12CC(N3CCOCC3)(C1)C2] | $C_{22}H_{29}F_2N_5O_2$ Calc: 433 Obsd: 434 | 1 |
| 52 | 5-(1-(bicyclo[1.1.1]-pentan-1-yl)-2-iso-propyl-1H-imidazol-4-yl)-3-(trifluoromethyl)-pyridin-2-amine | 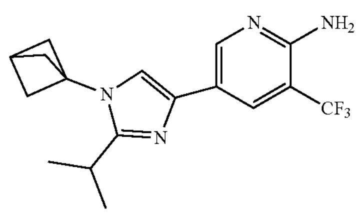 [SMILES: CC(C)c1nc(-c2cnc(N)c(C(F)(F)F)c2)cn1C12CC(C1)C2] | $C_{17}H_{19}F_3N_4$ Calc: 336 Obsd: 337 | 1 |
| 53 | (4-(6-amino-5-(trifluoro-methoxy)pyridin-3-yl)-1-(bicyclo[1.1.1]-pentan-1-yl)-1H-imidazol-2-yl)methanol | 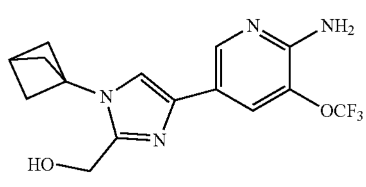 [SMILES: Nc1ncc(-c2cn(C34CC(C3)C4)c(CO)n2)cc1OC(F)(F)F] | $C_{15}H_{15}F_3N_4O_2$ Calc: 340 Obsd: 341 | 5 |

TABLE 1-continued

Additional Examples

| Ex # | Name | Structure | Formula; MS | Proc # |
|---|---|---|---|---|
| 54 | 1-(4-(6-amino-5-(tri-fluoromethoxy)pyridin-3-yl)-1-(bicyclo[1.1.1]-pentan-1-yl)-1H-imidazol-2-yl)propan-1-ol | 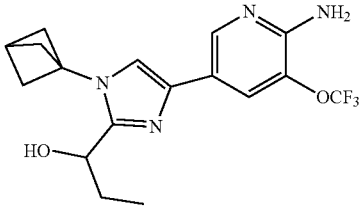 [SMILES: CCC(O)c1nc(-c2cnc(N)c(OC(F)(F)F)c2)cn1C12CC(C1)C2] | $C_{17}H_{19}F_3N_4O_2$ Calc: 368 Obsd: 369 | 5 |
| 55 | 1-(4-(6-amino-5-(tri-fluoromethoxy)pyridin-3-yl)-1-(bicyclo[1.1.1]-pentan-1-yl)-1H-imidazol-2-yl)ethan-1-ol | 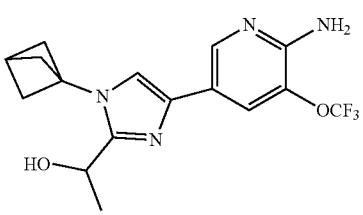 [SMILES: CC(O)c1nc(-c2cnc(N)c(OC(F)(F)F)c2)cn1C12CC(C1)C2] | $C_{16}H_{17}F_3N_4O_2$ Calc: 354 Obsd: 355 | 5 |
| 56 | (4-(6-amino-5-(tri-fluoromethoxy)pyridin-3-yl)-1-(bicyclo[1.1.1]-pentan-1-yl)-1H-imidazol-2-yl)(cyclo-propyl)methanol | 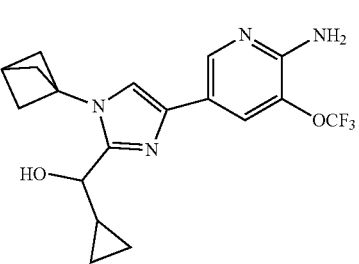 [SMILES: Nc1ncc(-c2cn(C34CC(C3)C4)c(C(O)C3CC3)n2)cc1OC(F)(F)F] | $C_{18}H_{19}F_3N_4O_2$ Calc: 380 Obsd: 381 | 5 |
| 57 | 1-(4-(6-amino-5-(tri-fluoromethoxy)pyridin-3-yl)-1-(bicyclo[1.1.1]-pentan-1-yl)-1H-imidazol-2-yl)-2-methyl-propan-1-ol | 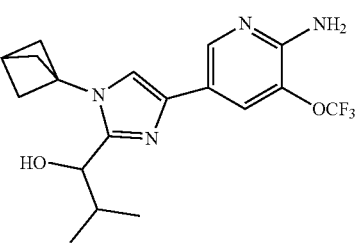 [SMILES: CC(C)C(O)c1nc(-c2cnc(N)c(OC(F)(F)F)c2)cn1C12CC(C1)C2] | $C_{18}H_{21}F_3N_4O_2$ Calc: 382 Obsd: 383 | 5 |
| 58 | (4-(6-amino-5-(trifluoro-methyl)pyridin-3-yl)-1-(bicyclo[1.1.1]-pentan-1-yl)-1H-imidazol-2-yl)methanol | 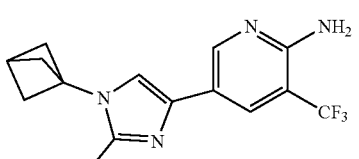 | $C_{15}H_{15}F_3N_4O$ Calc: 324 Obsd: 325 | 5 |
| 59 | 1-(4-(6-amino-5-(trifluoromethyl)-pyridin-3-yl)-1-(bi-cyclo[1.1.1]pentan-1-yl)-1H-imidazol-2-yl)-2-methylpropan-1-ol | 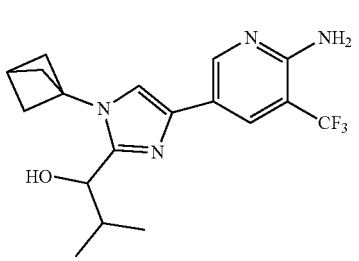 [SMILES: CC(C)C(O)c1nc(-c2cnc(N)c(C(F)(F)F)c2)cn1C12CC(C1)C2] | $C_{18}H_{21}F_3N_4O$ Calc: 366 Obsd: 367 | 5 |

TABLE 1-continued

Additional Examples

| Ex # | Name | Structure | Formula; MS | Proc # |
|---|---|---|---|---|
| 60 | (4-(6-amino-5-(trifluoro-methyl)pyridin-3-yl)-1-(bicyclo[1.1.1]-pentan-1-yl)-1H-imidazol-2-yl)(cyclopropyl)methanol | 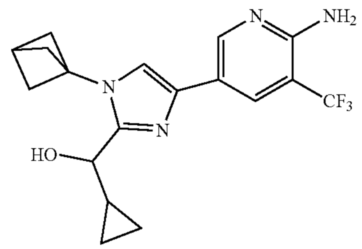 [SMILES: Nc1ncc(-c2cn(C34CC(C3)C4)c(C(O)C3CC3)n2)cc1C(F)(F)F] | $C_{18}H_{19}F_3N_4O$ Calc: 364 Obsd: 365 | 5 |
| 61 | 1-(4-(6-amino-5-(tri-fluoromethyl)pyridin-3-yl)-1-(bicyclo[1.1.1]-pentan-1-yl)-1H-imidazol-2-yl)propan-1-ol | 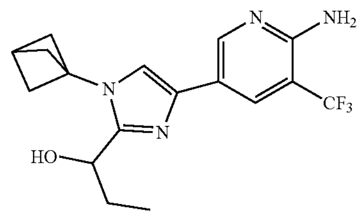 [SMILES: CCC(O)c1nc(-c2cnc(N)c(C(F)(F)F)c2)cn1C12CC(C1)C2] | $C_{17}H_{19}F_3N_4O$ Calc: 352 Obsd: 353 | 5 |
| 62 | 1-(4-(6-amino-5-(tri-fluoromethoxy)pyridin-3-yl)-1-(3-morpholino-bicyclo[1.1.1]pentan-1-yl)-1H-imidazol-2-yl)-2-methylpropan-1-ol | 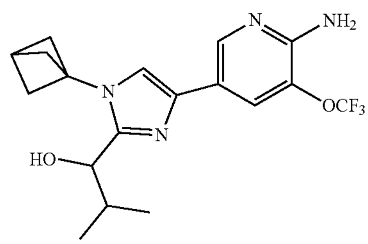 [SMILES: CC(C)C(O)c1nc(-c2cnc(N)c(OC(F)(F)F)c2)cn1C12CC(C1)C2] | $C_{22}H_{28}F_3N_5O_3$ Calc: 467 Obsd: 468 | 5 |
| 63a | 1-(4-(6-amino-5-(tri-fluoromethoxy)pyridin-3-yl)-1-(bicyclo[1.1.1]-pentan-1-yl)-1H-imidazol-2-yl)-2,2,2-trifluoroethan-1-ol | 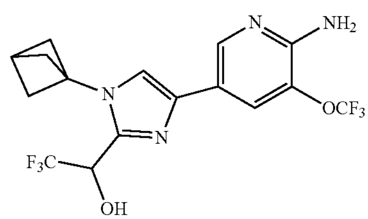 [SMILES: Nc1ncc(-c2cn(C34CC(C3)C4)c(C(O)C(F)(F)F)n2)cc1OC(F)(F)F] | $C_{16}H_{14}F_6N_4O_2$ Calc: 408 Obsd: 409 | 6 |
| 63b | 1-(4-(6-amino-5-(trifluoromethoxy)-pyridin-3-yl)-1-(bicyclo[1.1.1]pentan-1-yl)-1H-imidazol-2-yl)-2,2,2-trifluoroethan-1-ol | 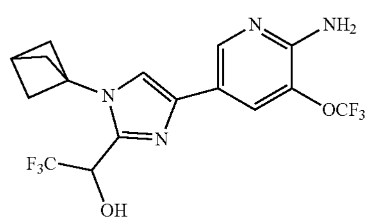 [SMILES: Nc1ncc(-c2cn(C34CC(C3)C4)c(C(O)C(F)(F)F)n2)cc1OC(F)(F)F] | $C_{16}H_{14}F_6N_4O_2$ Calc: 408 Obsd: 409 | 6 |
| 64 | 5-(2-((benzyloxy)-methyl)-1-(3-morpho-linobicyclo[1.1.1]-pentan-1-yl)-1H-imidazol-4-yl)-3-(trifluoro-methoxy)pyridin-2-amine | 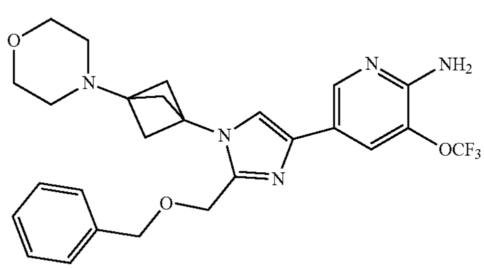 [SMILES: Nc1ncc(-c2cn(C34CC(N5CCOCC5)(C3)C4)c(COCc3ccccc3)n2)cc1OC(F)(F)F] | $C_{26}H_{28}F_3N_5O_3$ Calc: 515 Obsd: 516 | 7 |

TABLE 1-continued

Additional Examples

| Ex # | Name | Structure | Formula; MS | Proc # |
|---|---|---|---|---|
| 65 | (4-(6-amino-5-(trifluoro-methoxy)pyridin-3-yl)-1-(3-morpholino-bicyclo[1.1.1]pentan-1-yl)-1H-imidazol-2-yl)-methanol | 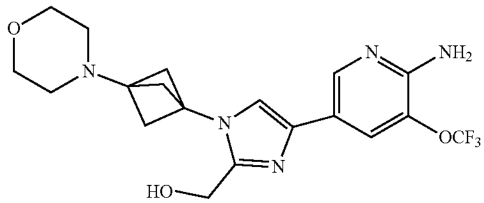 [SMILES: Nc1ncc(-c2cn(C34CC(N5CCOCC5)(C3)C4)c(CO)n2)cc1OC(F)(F)F] | $C_{19}H_{22}F_3N_5O_3$ Calc: 425 Obsd: 426 | 7 |
| 66 | 4-(6-amino-5-(trifluoro-methoxy)pyridin-3-yl)-1-(3-morpholino-bicyclo[1.1.1]pentan-1-yl)-1H-imidazole-2-carbaldehyde | 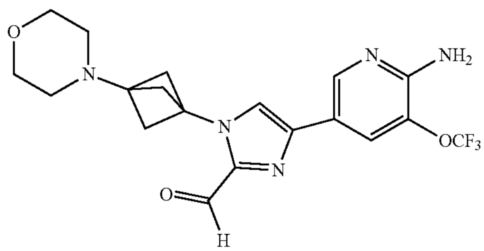 [SMILES: Nc1ncc(-c2cn(C34CC(N5CCOCC5)(C3)C4)c(C=O)n2)cc1OC(F)(F)F] | $C_{19}H_{20}F_3N_5O_3$ Calc: 423 Obsd: 424 | 7 |
| 67 | 1-(4-(6-amino-5-(tri-fluoromethyl)pyridin-3-yl)-1-(3-morpholino-bicyclo[1.1.1]pentan-1-yl)-1H-imidazol-2-yl)-2-methylpropan-1-ol | 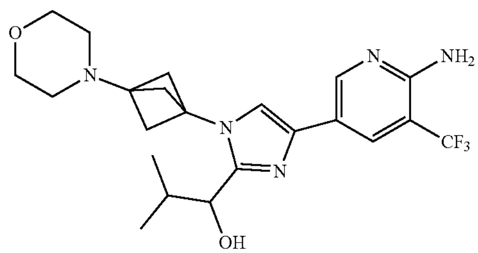 [SMILES: CC(C)C(O)c1nc(-c2cnc(N)c(C(F)(F)F)c2)cn1C12CC(N3CCOCC3)(C1)C2] | $C_{22}H_{28}F_3N_5O_2$ Calc: 451 Obsd: 452 | 7 |
| 68 | 1-(4-(6-amino-5-(tri-fluoromethyl)pyridin-3-yl)-1-(3-morpholino-bicyclo[1.1.1]pentan-1-yl)-1H-imidazol-2-yl)-2-methylpropan-1-ol | 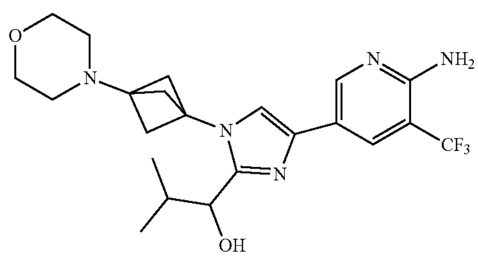 [SMILES: CC(C)C(O)c1nc(-c2cnc(N)c(C(F)(F)F)c2)cn1C12CC(N3CCOCC3)(C1)C2] | $C_{22}H_{28}F_3N_5O_2$ Calc: 451 Obsd: 452 | 7 |
| 69a | 1-(4-(6-amino-5-(tri-fluoromethyl)pyridin-3-yl)-1-(3-morpholino-bicyclo[1.1.1]pentan-1-yl)-1H-imidazol-2-yl)-2,2,2-trifluoroethan-1-ol | 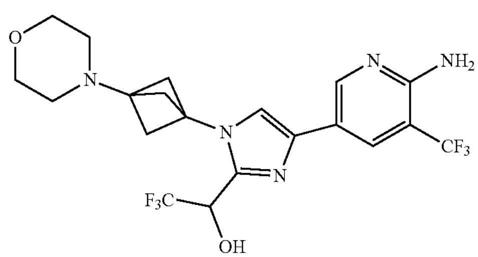 [SMILES: Nc1ncc(-c2cn(C34CC(N5CCOCC5)(C3)C4)c(C(O)C(F)(F)F)n2)cc1C(F)(F)F] | $C_{20}H_{21}F_6N_5O_2$ Calc: 477 Obsd: 478 | 8 |
| 69b | 1-(4-(6-amino-5-(tri-fluoromethyl)pyridin-3-yl)-1-(3-morpholino-bicyclo[1.1.1]pentan-1-yl)-1H-imidazol-2-yl)-2,2,2-trifluoroethan-1-ol | 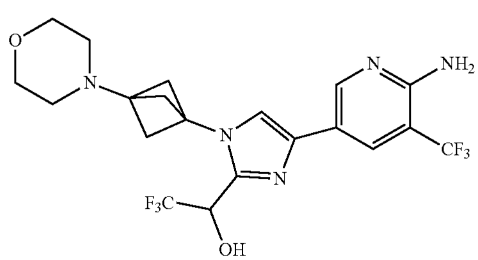 [SMILES: Nc1ncc(-c2cn(C34CC(N5CCOCC5)(C3)C4)c(C(O)C(F)(F)F)n2)cc1C(F)(F)F] | $C_{20}H_{21}F_6N_5O_2$ Calc: 477 Obsd: 478 | 8 |

TABLE 1-continued

Additional Examples

| Ex # | Name | Structure | Formula; MS | Proc # |
|---|---|---|---|---|
| 70 | 1-(4-(6-amino-5-(tri-fluoromethoxy)pyridin-3-yl)-1-(3-(4-propyl-piperazin-1-yl)bicyclo-[1.1.1]pentan-1-yl)-1H-imidazol-2-yl)-2-methylpropan-1-ol | 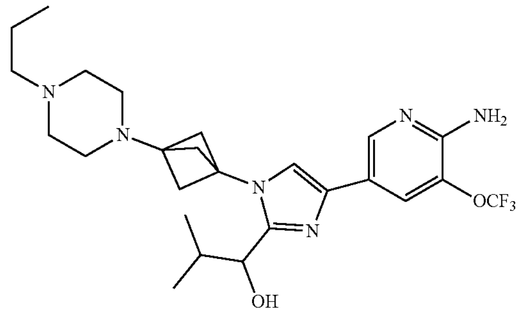 [SMILES: CCCN1CCN(C23CC(n4cc(-c5cnc(N)c(OC(F)(F)F)c5)nc4C(O)C(C)C)(C2)C3)CC1] | $C_{25}H_{35}F_3N_6O_2$ Calc: 508 Obsd: 509 | 9 |
| 71 | 3-(difluoromethoxy)-5-(1-isopropyl-5-(3-morpholinobicyclo-[1.1.1]pentan-1-yl)-1H-pyrazol-3-yl)pyridin-2-amine | 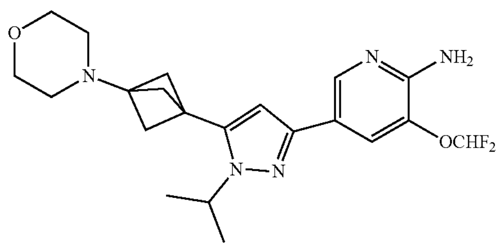 [SMILES: CC(C)n1nc(-c2cnc(N)c(OC(F)F)c2)cc1C12CC(N3CCOCC3)(C1)C2] | $C_{21}H_{27}F_2N_5O_2$ Calc: 419 Obsd: 420 | 11 |
| 72 | 5-(2-(cyclopropyl-methyl)-1-(3-(4-methylpiperazin-1-yl)-bicyclo[1.1.1]pentan-1-yl)-1H-imidazol-4-yl)-3-(trifluoromethoxy)-pyridin-2-amine | 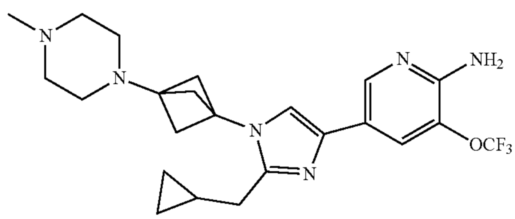 [SMILES: CN1CCN(C23CC(n4cc(-c5cnc(N)c(OC(F)(F)F)c5)nc4CC4CC4)(C2)C3)CC1] | $C_{23}H_{29}F_3N_6O$ Calc: 462 Obsd: 463 | 12 |
| 73 | 5-(2-(cyclopropyl-methyl)-1-(3-(4-methylpiperazin-1-yl)-bicyclo[1.1.1]pentan-1-yl)-1H-imidazol-4-yl)-3-(difluoromethoxy)-pyridin-2-amine | 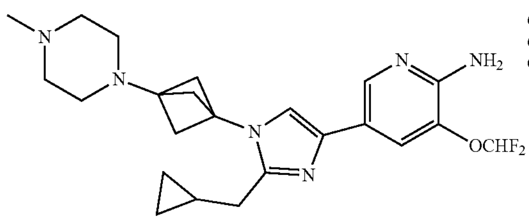 [SMILES: CN1CCN(C23CC(n4cc(-c5cnc(N)c(OC(F)F)c5)nc4CC4CC4)(C2)C3)CC1] | $C_{23}H_{30}F_2N_6O$ Calc: 444 Obsd: 445 | 12 |
| 74 | 5-(2-isopropyl-1-(3-(4-methylpiperazin-1-yl)-bicyclo[1.1.1]pentan-1-yl)-1H-imidazol-4-yl)-3-(trifluoromethoxy)-pyridin-2-amine | 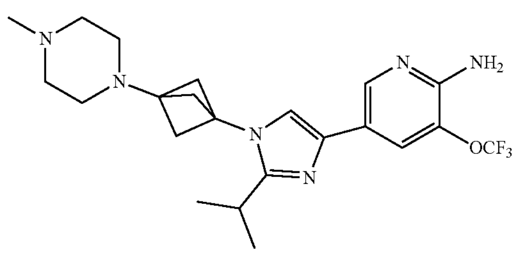 [SMILES: CC(C)c1nc(-c2cnc(N)c(OC(F)(F)F)c2)cn1C12CC(N3CCN(C)CC3)(C1)C2] | $C_{22}H_{29}F_3N_6O$ Calc: 450 Obsd: 451 | 12 |
| 75 | 5-(2-cyclopropyl-1-(3-(4-methylpiperazin-1-yl)bicyclo[1.1.1]-pentan-1-yl)-1H-imidazol-4-yl)-3-(trifluoro-methyl)pyridin-2-amine | 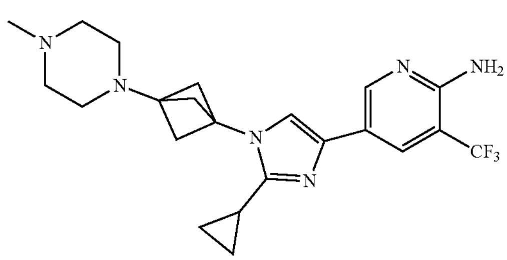 [SMILES: CN1CCN(C23CC(n4cc(-c5cnc(N)c(C(F)(F)F)c5)nc4C4CC4)(C2)C3)CC1] | $C_{22}H_{27}F_3N_6$ Calc: 432 Obsd: 433 | 12 |

… TABLE 1-continued

Additional Examples

| Ex # | Name | Structure | Formula; MS | Proc # |
|---|---|---|---|---|
| 76 | 5-(2-cyclopropyl-1-(3-(4-methylpiperazin-1-yl)bicyclo[1.1.1]-pentan-1-yl)-1H-imidazol-4-yl)-3-(difluoro-methoxy)pyridin-2-amine | 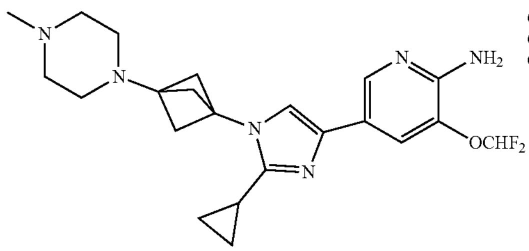 [SMILES: CN1CCN(C23CC(n4cc(-c5cnc(N)c(OC(F)F)c5)nc4C4CC4)(C2)C3)CC1] | $C_{22}H_{28}F_2N_6O$<br>Calc: 430<br>Obsd: 431 | 12 |

The following compound can generally be made using the methods described above. It is expected that this compound when made will have activity similar to those that have been made in the examples disclosed herein.

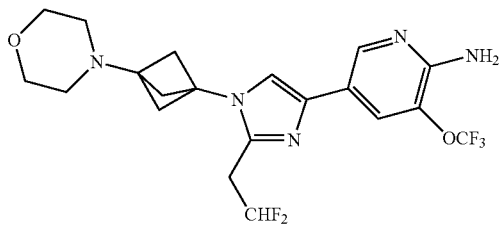 [SMILES: Nc1ncc(-c2cn(C34CC(N5CCOCC5)(C3)C4)c(CC(F)F)n2)cc1OC(F)(F)F]

The activity of the compounds in Examples 1-76 as DLK inhibitors is illustrated in the following assays.

Biological Activity Assays

Compounds described herein have been shown to bind DLK in vitro, and to inhibit phosphorylation of a downstream molecular target in a cellular assay.

DLK $K_d$ Determinations

The DLK dissociation constants ($K_d$) have been determined in the KINOMEscan KdELECT Service at DiscoveRx.

A fusion protein of full length of human DLK (amino acids 1-859) and the DNA binding domain of NFkB was expressed in transiently transfected HEK293 cells. From these HEK 293 cells, extracts were prepared in M-PER extraction buffer (Pierce) in the presence of Protease Inhibitor Cocktail Complete (Roche) and Phosphatase Inhibitor Cocktail Set II (Merck) per manufacturers' instructions. The DLK fusion protein was labeled with a chimeric double-stranded DNA tag containing the NFkB binding site (5'-GGGAATTCCC-3') fused to an amplicon for qPCR readout, which was added directly to the expression extract (the final concentration of DNA-tag in the binding reaction is 0.1 nM).

Streptavidin-coated magnetic beads (Dynal M280) were treated with a biotinylated small molecule ligand for 30 minutes at room temperature to generate affinity resins the binding assays. The liganded beads were blocked with excess biotin and washed with blocking buffer (SeaBlock (Pierce), 1% BSA, 0.05% Tween 20, 1 mM DTT) to remove unbound ligand and to reduce nonspecific binding.

The binding reaction was assembled by combining 16 µl of DNA-tagged kinase extract, 3.8 µl liganded affinity beads, and 0.18 µl test compound (PBS/0.05% Tween 20/10 mM DTT/0.1% BSA/2 µg/ml sonicated salmon sperm DNA)]. Extracts were used directly in binding assays without any enzyme purification steps at a ≥10,000-fold overall stock dilution (final DNA-tagged enzyme concentration<0.1 nM). Extracts were loaded with DNA-tag and diluted into the binding reaction in a two step process. First extracts were diluted 1:100 in 1× binding buffer (PBS/0.05% Tween 20/10 mM DTT/0.1% BSA/2 µg/ml sonicated salmon sperm DNA) containing 10 nM DNA-tag. This dilution was allowed to equilibrate at room temperature for 15 minutes and then subsequently diluted 1:100 in 1× binding buffer. Test compounds were prepared as 111× stocks in 100% DMSO. $K_d$s were determined using an 11-point 3-fold compound dilution series with three DMSO control points. All compounds for $K_d$ measurements are distributed by acoustic transfer (non-contact dispensing) in 100% DMSO. The compounds were then diluted directly into the assays such that the final concentration of DMSO was 0.9%. All reactions performed in polypropylene 384-well plates. Each was a final volume of 0.02 mL. Assays were incubated with shaking for 1 hour at room temperature. Then the beads were pelleted and washed with wash buffer (1×PBS, 0.05% Tween 20) to remove displaced kinase and test compound. The washed based were re-suspended in elution buffer (1x PBS, 0.05% Tween 20, 0.5 µM non-biotinylated affinity ligand) and incubated at room temperature with shaking for 30 minutes. The kinase concentration in the eluates was measured by qPCR. qPCR reactions were assembled by adding 2.5 µL of kinase eluate to 7.5 µL of qPCR master mix containing 0.15 µM amplicon primers and 0.15 µM amplicon probe. The qPCR protocol consisted of a 10 minute hot start at 95° C., followed by 35 cycles of 95° C. for 15 seconds, 60° C. for 1 minute.

Test compound Handling. Test compounds were prepared as 111× stocks in 100% DMSO. $K_d$s were determined using an 11-point 3-fold compound dilution series with three DMSO control points. All compounds for $K_d$ measurements are distributed by acoustic transfer (non-contact dispensing) in 100% DMSO. The compounds were then diluted directly into the assays such that the final concentration of DMSO was 0.9%. The $K_d$s were determined using a compound top concentration of 30,000 nM. $K_d$ measurements were performed in duplicate.

Binding Constant ($K_d$) Calculation.

Binding constants ($K_d$s) were calculated with a standard dose-response curve using the Hill equation:

$$\text{Response} = \text{Background} + \frac{(\text{Signal} - \text{Background})}{\left(1 + \left(\frac{Kd^{Hill\ Slope}}{\text{Dose}^{Hill\ Slope}}\right)\right)}$$

The Hill Slope was set to −1. Curves were fitted using a non-linear least square fit with the Levenberg-Marquardt algorithm (Levenberg, K., A method for the solution of certain non-linear problems in least squares, *Q. Appl. Math.* 2, 164-168 (1944)). See also Fabian, M. A. et al. A small molecule-kinase interaction map for clinical kinase inhibitors. Nat. Biotechnol. 23, 329-336 (2005); Wodicka, L. M. et al. Activation state-dependent binding of small molecule kinase inhibitors: structural insights from biochemistry. *Chem Biol.* 17, 1241-9 (2010).

Compounds with lower dissociation constants bind with more affinity to the target. Compounds disclosed herein, particularly (but not exclusively) those with lower dissociation constants, can be expected to inhibit target activity and to be useful in the treatment of DLK-mediated disease. Results are reported below in Tables 2a and 2b in nM.

Phospho-cJun Cellular Assay

HEK293 cells stably transfected with a Dox-inducible human DLK were plated into a 384-well plate in 20 μl (40,000 cells/well) of DMEM medium (without phenol red) containing 10% fetal bovine serum, 1.5 μg/ml doxycycline and 1 μg/ml puromycin. The cells as negative control were grown in the absence of doxycycline. The plate was incubated at 37° C., 5% $CO_2$ for 20 h, before DMSO (control) or compounds diluted in medium were added. The cells were incubated at 37° C. for an additional 5 h, followed by lysis and the addition detection antibodies from p-cJun (Ser63) cellular assay kit (Cisbio) per manufacturer protocol. The standard dose response curves were fitted by Genedata Screener software using the variable-slope model: Signal=Signal negative control+(Signal$_{DMSO\ control}$−Signal$_{negative\ control}$)/(1+($IC_{50}$/Dose)^Hill slope). Only signal and dose in the equation were treated as known values. Results are reported below in Tables 2a and 2b in nM. Values in table 2b reflect additional assay runs on multiple batches of compound, and include data from Table 2a in the averaging.

TABLE 2a

DLK activity

| Ex. | Avg DLK $K_d$, nM | Avg Phospho-cJun Cell $IC_{50}$, nM |
|---|---|---|
| 1 | 13 | 259 |
| 2 | 13 | 459 |
| 3 | 11 | 402 |
| 4 | 13 | 366 |

TABLE 2b

DLK activity (global)

| Ex. | Kd, nM | Cell IC50 |
|---|---|---|
| 1 | 11.4 | 287.8 |
| 2 | 13 | 430.8 |
| 3 | 11 | 367.8 |
| 4 | 8.3 | 400 |
| 5a | | 1046.6 |

TABLE 2b-continued

DLK activity (global)

| Ex. | Kd, nM | Cell IC50 |
|---|---|---|
| 5b | 2.3 | 99.4 |
| 6a | | 745.2 |
| 6b | 0.74 | 38.7 |
| 7a | | 10.7 |
| 7b | 45 | 860.0 |
| 8a | 0.36 | 24.8 |
| 8b | | 283.6 |
| 9a | | 20.2 |
| 9b | | 684.1 |
| 10 | 0.31 | 13.9 |
| 11 | 15 | 602.5 |
| 12 | 20 | 252 |
| 13 | 32 | 316.5 |
| 14 | 47 | 880.5 |
| 15 | 18 | 540 |
| 16 | 24 | 456.5 |
| 17 | 6.9 | 281.5 |
| 18 | 1.9 | 155 |
| 19 | 14 | 600 |
| 20 | 7500 | 12000 |
| 21 | 330 | 5871 |
| 22 | 9.7 | 403.8 |
| 23 | 17 | 471 |
| 24 | 6.8 | 553 |
| 25 | 6.4 | 388.5 |
| 26 | 7 | 383 |
| 27 | 29 | 1024.5 |
| 28 | 2.9 | 147.8 |
| 29 | 20 | 531 |
| 30 | 390 | 5105.5 |
| 31 | 170 | 2567 |
| 32 | 6.7 | 518 |
| 33 | 9.7 | 206.6 |
| 34 | 29 | 453.5 |
| 35 | 7.2 | 494.3 |
| 36 | 22 | 500 |
| 37 | 19 | 351 |
| 38 | 19 | 709.3 |
| 39 | 210 | 4043 |
| 40 | 66 | 2458 |
| 41 | 82 | 3857 |
| 42 | 3.1 | 238.5 |
| 43 | 32 | 597.5 |
| 44 | 53 | 841.5 |
| 45 | 15 | 760.7 |
| 46 | 29 | 830 |
| 47 | 6 | 654.5 |
| 48 | 13 | 413.5 |
| 49 | 8.6 | 289.7 |
| 50 | 9.5 | 292.5 |
| 51 | 21 | 763.2 |
| 52 | 49 | 849.5 |
| 53 | 30 | 1328 |
| 54 | 11 | 318.7 |
| 55 | 14 | 443.2 |
| 56 | 5.1 | 275.2 |
| 57 | 0.62 | 38.6 |
| 58 | 18 | 845.9 |
| 59 | 0.29 | 20.9 |
| 60 | 2.4 | 214.0 |
| 61 | 2.1 | 167.0 |
| 62 | 1.1 | 43.0 |
| 63a | | 1958 |
| 63b | 1.6 | 43.6 |
| 64 | 14 | 192.2 |
| 65 | 79 | 868.8 |
| 66 | 44 | 1400.7 |
| 67 | 0.11 | 12.1 |
| 68 | 13 | 934.5 |
| 69a | 0.36 | 36.7 |
| 69b | | 722.5 |

TABLE 2b-continued

| | DLK activity (global) | |
|---|---|---|
| Ex. | Kd, nM | Cell IC50 |
| 70 | | 923.1 |
| 71 | 13 | 308.3 |
| 72 | 19 | 1160.5 |
| 73 | 18 | 624 |
| 74 | 4.5 | 195.8 |
| 75 | 7.5 | 255.8 |
| 76 | 7.4 | 300.8 |

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treating a disease selected from the group consisting of chemotherapy-induced cognitive deficits (CICD), chemotherapy-induced cognitive impairment (CICI), chemotherapy-induced peripheral neuropathy (CIPN), diabetic neuropathy, Alzheimer's disease, amyotrophic lateral sclerosis, frontotemporal dementia, Huntington's disease, Kennedy's disease, Lewy body disease, Parkinson's disease, progressive supranuclear palsy, spinocerebellar ataxia, traumatic brain injury (TBI), and traumatic injury to the central nervous system or peripheral nervous system neurons, the method comprising administering to a patient in need thereof a therapeutically effective amount of a compound of Formula I:

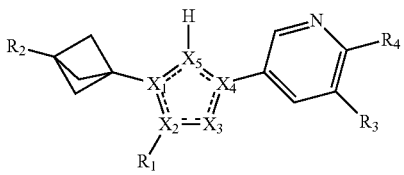

or a pharmaceutically acceptable salt thereof,
wherein:

$X_1$ is selected from C or N;

$X_2$ is selected from C or N;

exactly one of $X_1$ and $X_2$ is N;

$X_3$ is N;

$X_4$ and $X_5$ are C;

$X_1$, $X_2$, $X_3$, $X_4$, and $X_5$ form a five membered heteroaryl;

$R_1$ is selected from alkyl, cycloalkyl, or heterocycloalkyl, any of which is optionally substituted with one to three $R_5$ groups;

$R_2$ is H or is selected from alkyl, amino, aryl, cycloalkyl, haloalkyl, heteroalkyl, heteroaryl, heterocycloalkyl, or sulfonylalkyl, any of which is optionally substituted with one to three $R_6$ groups;

$R_3$ is selected from H, alkyl, (alkoxy)alkyl, (arylalkoxy)alkyl, (heteroarylalkoxy)alkyl, cyano, cycloalkyl, halo, haloalkoxy, or haloalkyl;

$R_4$ is $(NR_{4a})_2$, wherein each $R_{4a}$ is independently selected from hydrogen, $C_{1-4}$alkyl, or $C_{1-4}$haloalkyl;

or $R_3$ and $R_4$ together with the atoms to which they are attached form a 5- or 6-membered heteroaryl or heteroalkyl ring, optionally substituted with one to three $R_7$ groups;

each $R_5$ and $R_6$ is independently selected from $C_{1-4}$alkyl, $C_{1-4}$haloalkyl, $C_{1-4}$alkoxy, $C_{1-4}$haloalkoxy, $C_{1-4}$-alkylthio, $C_{1-4}$haloalkylthio, aryl, heteroaryl, $C_{3-7}$cycloalkyl, $C_{3-7}$heterocycloalkyl, (aryl)$C_{1-4}$alkyl, (heteroaryl)$C_{1-4}$alkyl, ($C_{3-7}$cycloalkyl)$C_{1-4}$alkyl, ($C_{3-7}$heterocycloalkyl)$C_{1-4}$alkyl, (ethenyl)$C_{1-4}$alkyl, (ethynyl)$C_{1-4}$alkyl, (aryl)$C_{1-4}$alkoxy, (heteroaryl)$C_{1-4}$alkoxy, ($C_{3-7}$cycloalkyl)$C_{1-4}$alkoxy, ($C_{3-7}$heterocycloalkyl)$C_{1-4}$alkoxy, (aryl)$C_{1-4}$alkylthio, (heteroaryl)$C_{1-4}$alkylthio, ($C_{3-7}$cycloalkyl)$C_{1-4}$alkylthio, ($C_{3-7}$heterocycloalkyl)$C_{1-4}$alkylthio, amino, halo, hydroxy, cyano, or oxo; and each $R_7$ is independently selected from $C_{1-4}$alkyl, $C_{1-4}$haloalkyl, $C_{1-4}$alkoxy, $C_{1-4}$haloalkoxy, aryl, heteroaryl, $C_{3-7}$cycloalkyl, $C_{3-7}$heterocycloalkyl, (aryl)$C_{1-4}$alkyl, (heteroaryl)$C_{1-4}$alkyl, ($C_{3-7}$cycloalkyl)$C_{1-4}$alkyl, ($C_{3-7}$heterocycloalkyl)$C_{1-4}$alkyl, halo, hydroxy, cyano, or oxo.

2. The method of claim 1, wherein $R_1$ is methyl, and is optionally substituted with one or two $R_5$ groups.

3. The method of claim 2, wherein $R_1$ is hydroxymethyl and is optionally substituted with one $R_5$ group.

4. The method of claim 3, wherein $R_5$ is selected from $C_{1-4}$alkyl, $C_{1-4}$haloalkyl, $C_{3-7}$cycloalkyl, or $C_{3-7}$heterocycloalkyl.

5. The method of claim 4, wherein $R_5$ is selected from methyl, ethyl, trifluoromethyl, 2-propyl, or cyclopropyl.

6. The method of claim 5, wherein
$R_3$ is selected from $CF_3$ or $OCF_3$; and
$R_4$ is $NH_2$.

7. The method of claim 6, wherein $R_2$ is H or is selected from alkyl, cycloalkyl, heteroalkyl, or heterocycloalkyl, any of which is optionally substituted with one or two $R_6$ groups.

8. The method of claim 7, wherein $R_6$ is selected from $C_{1-4}$alkyl, $C_{1-4}$haloalkyl, (ethenyl)$C_{1-4}$-alkyl, (ethynyl)$C_{1-4}$alkyl, hydroxy, or oxo.

9. The method of claim 8, wherein $R_2$ is selected from morpholin-1-yl, piperidin-1-yl, or piperazin-1-yl, any of which is optionally substituted with one or two $R_6$ groups.

10. The method of claim 8, wherein $R_2$ is H.

11. The method as recited in claim 1, comprising the administration to a patient in need thereof of a therapeutically effective amount of a compound having structural Formula II:

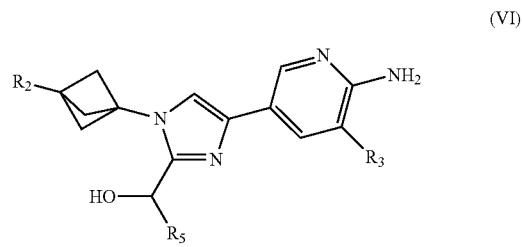

(II)

or a salt thereof, wherein:
$R_1$ is selected from alkyl, cycloalkyl, or heterocycloalkyl, any of which is optionally substituted with one to three $R_5$ groups;
$R_3$ is selected from H, alkyl, cyano, cycloalkyl, halo, haloalkoxy, or haloalkyl;
$R_{8a}$ and $R_{8b}$ are independently selected from $C_{1-4}$alkyl, $C_{1-4}$haloalkyl, $(C_{1-4}$alkoxy$)C_{1-4}$alkyl, $(C_{1-4}$haloalkoxy$)C_{1-4}$alkyl, $(C_{1-4}$alkoxy$)C_{1-4}$haloalkyl, or $(C_{1-4}$haloalkoxy$)C_{1-4}$haloalkyl,
or $R_{8a}$ and $R_{8b}$, in combination with the intervening atoms, form a 4-7 membered heterocycloalkyl ring, which is optionally substituted with one to three $R_6$ groups; and
each $R_5$ and $R_6$ is independently selected from $C_{1-4}$alkyl, $C_{1-4}$haloalkyl, $C_{1-4}$alkoxy, $C_{1-4}$haloalkoxy, $C_{1-4}$alkylthio, $C_{1-4}$haloalkylthio, aryl, heteroaryl, $C_{3-7}$cycloalkyl, $C_{3-7}$heterocycloalkyl, (aryl)$C_{1-4}$alkyl, (heteroaryl)$C_{1-4}$alkyl, (ethenyl)$C_{1-4}$alkyl, (ethynyl)$C_{1-4}$alkyl, (aryl)$C_{1-4}$alkoxy, (heteroaryl)$C_{1-4}$alkoxy, (aryl)$C_{1-4}$alkylthio, (heteroaryl)$C_{1-4}$alkylthio, amino, halo, hydroxy, cyano, or oxo.

12. The method as recited in claim 11, wherein $R_{8a}$ and $R_{8b}$, in combination with the intervening atoms, form a 4-7 membered heterocycloalkyl ring, which is optionally substituted with one to three $R_6$ groups.

13. The method as recited in claim 12, wherein $R_{8a}$ and $R_{8b}$, in combination with the intervening atoms, form a morpholine, piperidine, or piperazine ring, any of which is optionally substituted with one to three $R_6$ groups.

14. The method of claim 13, wherein $R_1$ is selected from cyclopropyl, cyclopropylmethyl or isopropyl.

15. The method of claim 14, wherein $R_3$ is selected from difluoromethoxy, trifluoromethoxy, or trifluoromethyl.

16. The method of claim 1, comprising the administration to a patient in need thereof of a therapeutically effective amount of a compound having structural Formula VI:

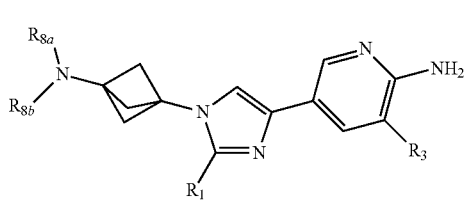

(VI)

or a salt thereof, wherein:
$R_2$ is H or is selected from alkyl, amino, aryl, cycloalkyl, haloalkyl, heteroalkyl, heteroaryl, heterocycloalkyl, or sulfonylalkyl, any of which is optionally substituted with one to two $R_6$ groups;
$R_3$ is selected from haloalkoxy or haloalkyl;
$R_5$ is selected from $C_{1-4}$alkyl, $C_{1-4}$haloalkyl, or $C_{3-7}$cycloalkyl; and
each $R_6$ is independently selected from $C_{1-4}$alkyl, $C_{1-4}$haloalkyl, (ethenyl)$C_{1-4}$alkyl, (ethynyl)$C_{1-4}$alkyl, amino, halo, hydroxy, cyano, or oxo.

17. The method of claim 16, wherein $R_3$ is selected from difluoromethoxy, trifluoromethoxy, or trifluoromethyl.

18. The method of claim 17, wherein $R_5$ is selected from $C_{1-4}$alkyl or $C_{1-4}$haloalkyl.

19. The method of claim 18, wherein $R_5$ is selected from methyl or trifluoromethyl.

20. The method of claim 19, wherein
$R_2$ is selected from

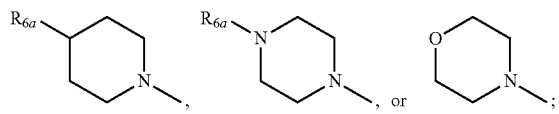

and
$R_{6a}$ is selected from H, $C_{1-4}$alkyl, $C_{1-4}$haloalkyl, (ethenyl)$C_{1-4}$alkyl, or (ethynyl)$C_{1-4}$alkyl.

21. The method of claim 19, wherein $R_2$ is H.

22. The method of claim 1, wherein the compound has the structural formula selected from:

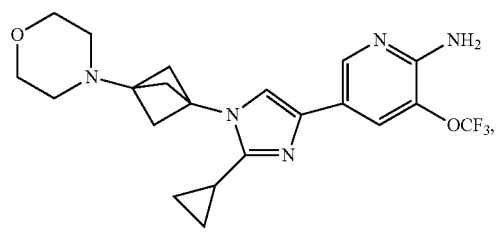

107
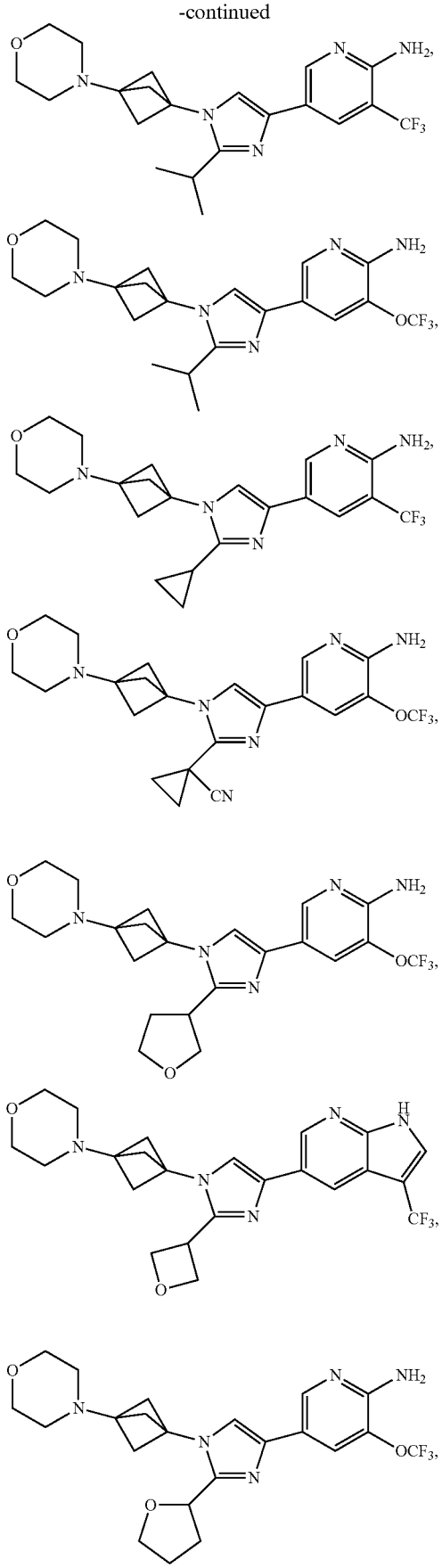
108
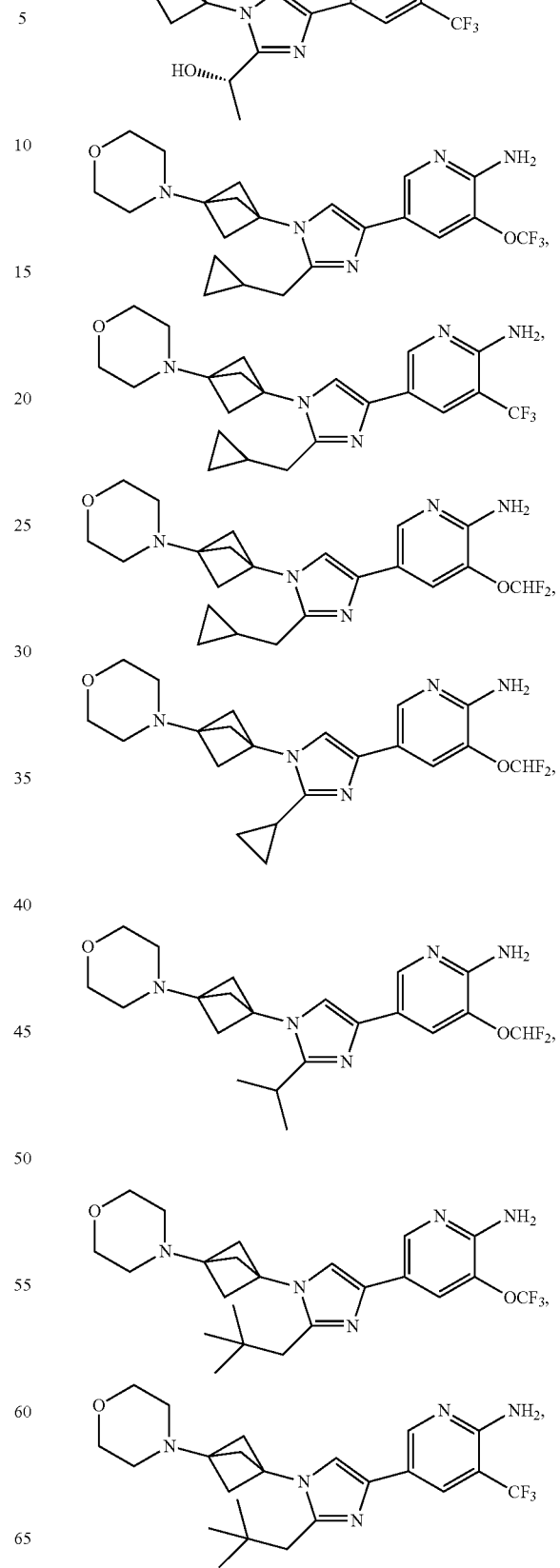

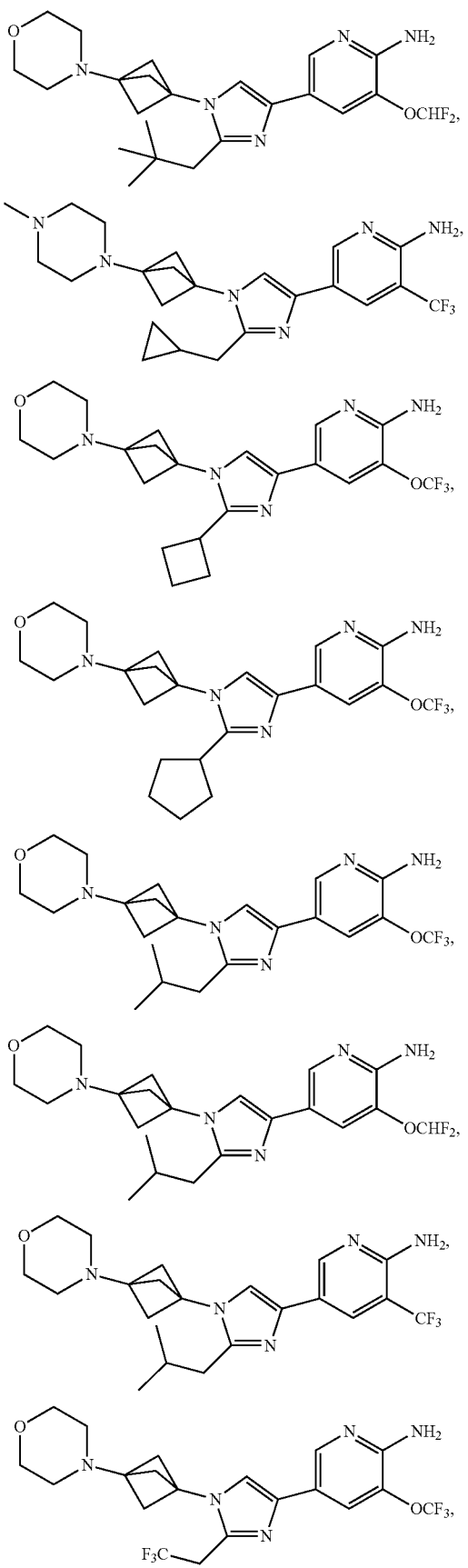
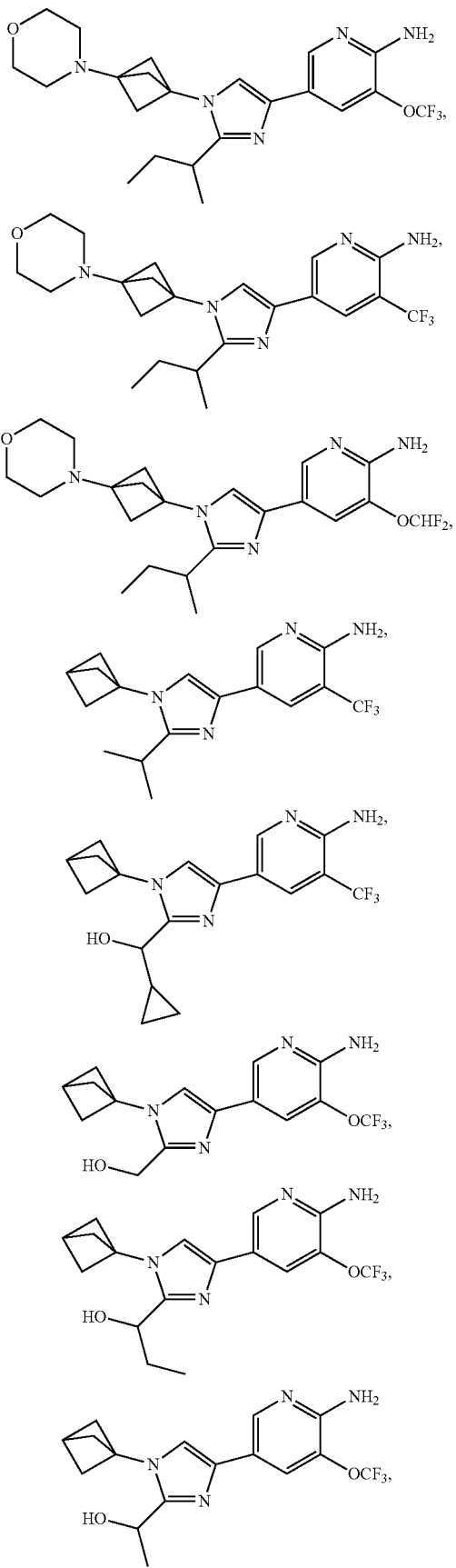

-continued
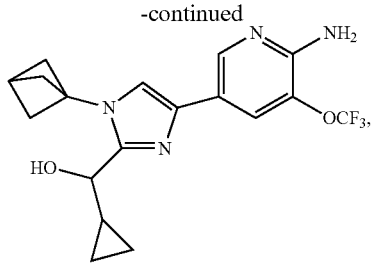
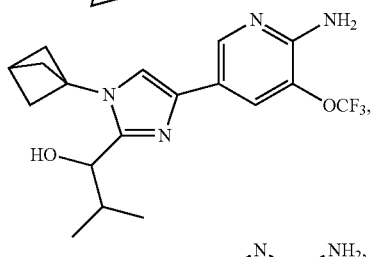
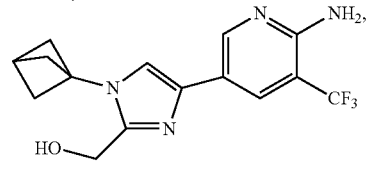
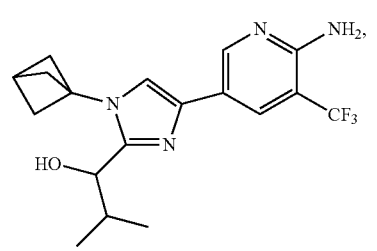
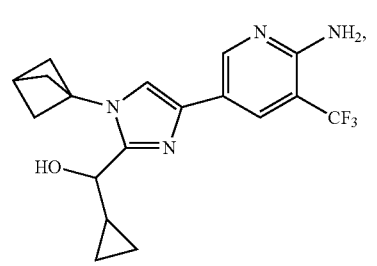
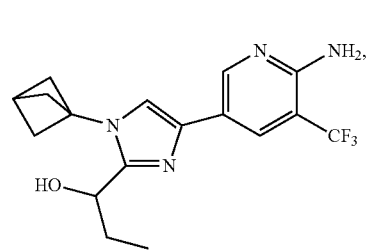
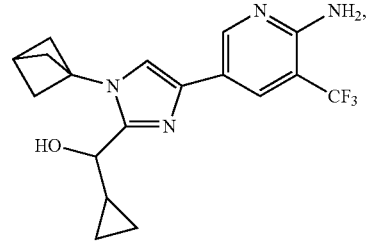
-continued
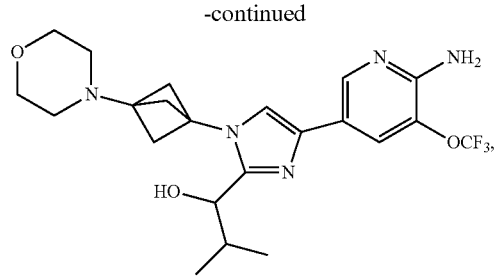
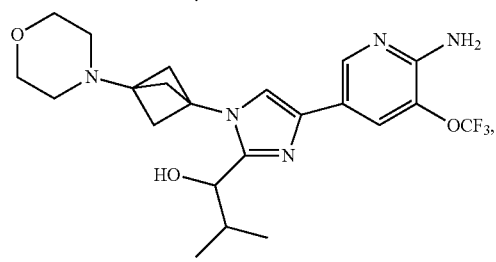
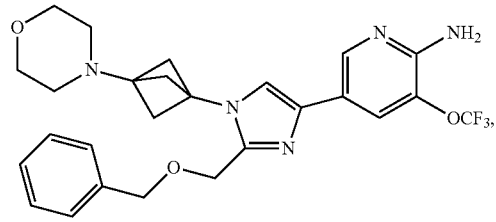
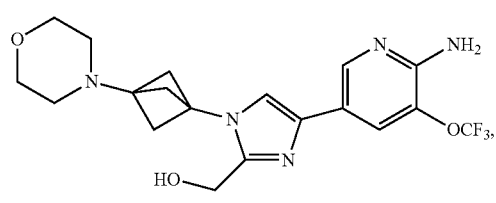
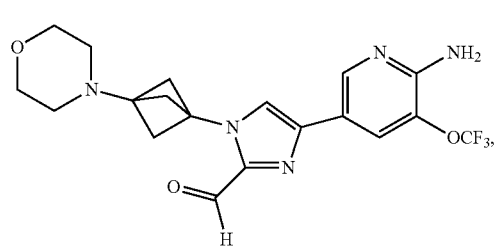
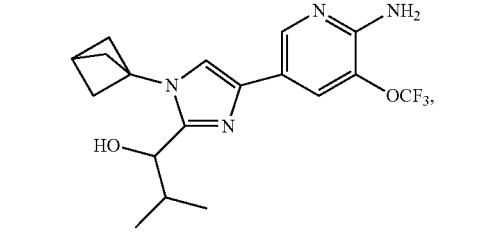
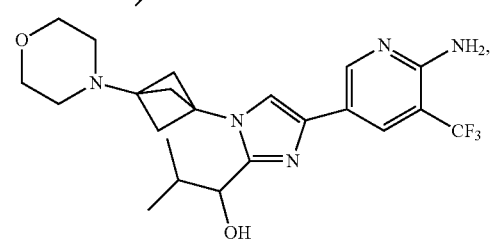

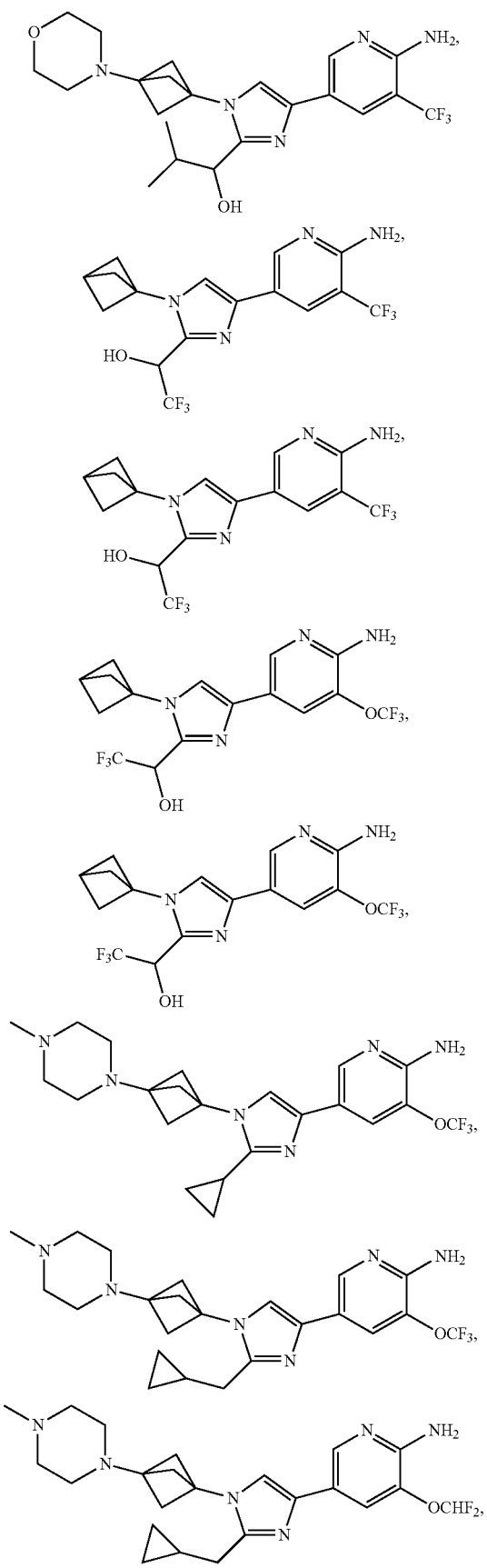
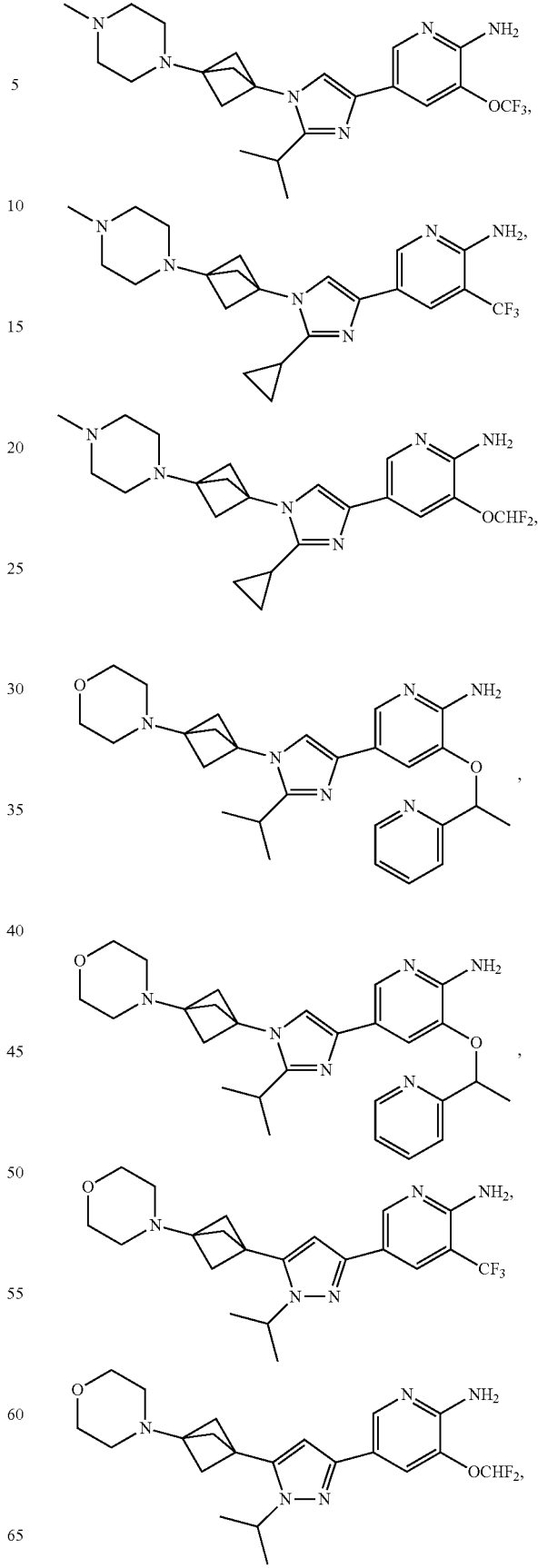

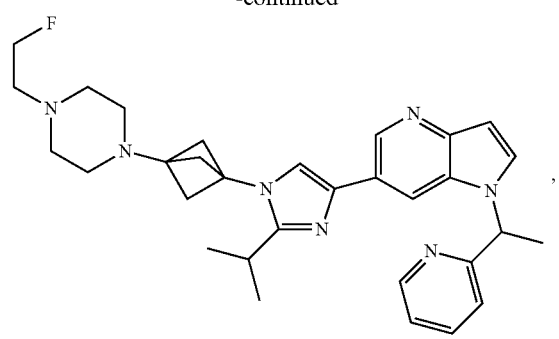
,
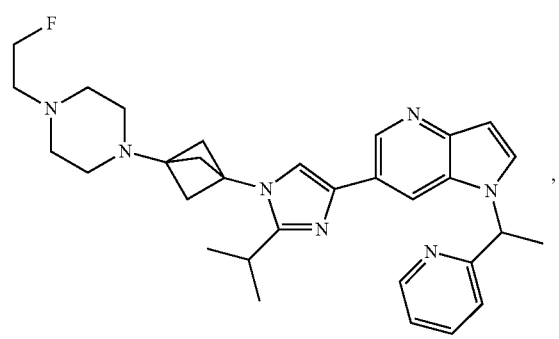
,
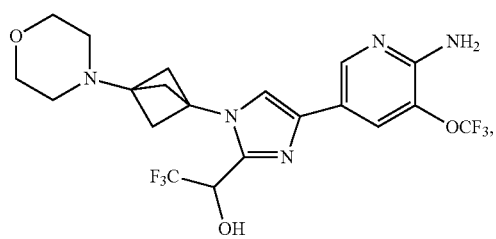
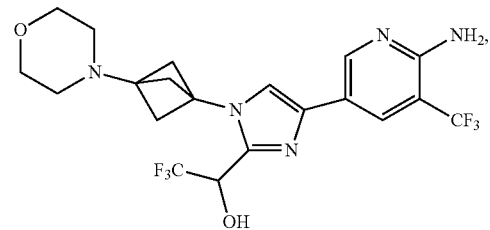
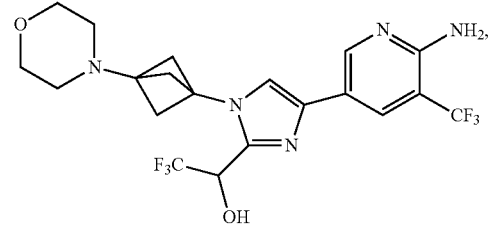
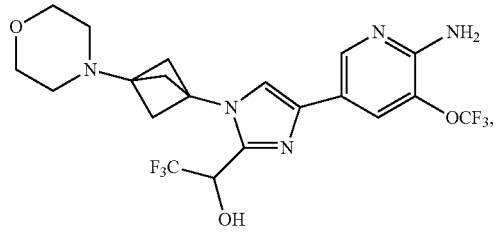
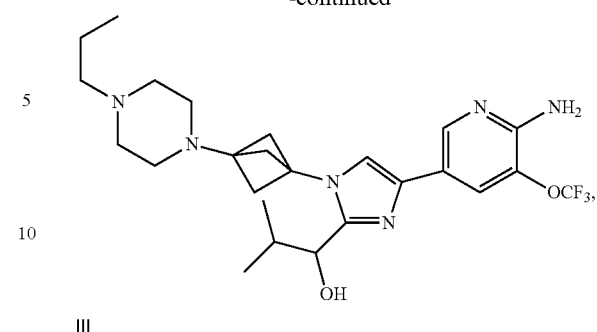
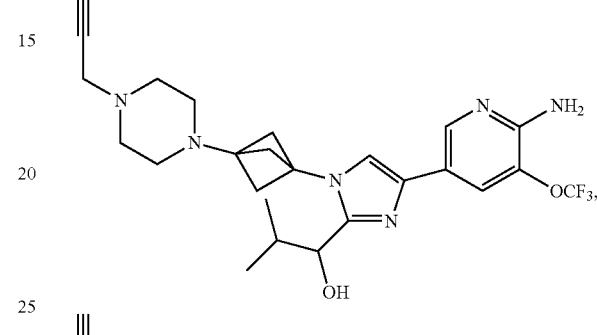
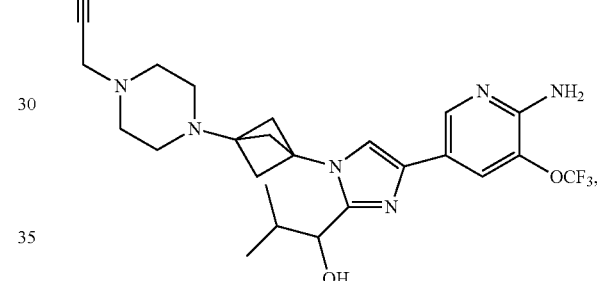
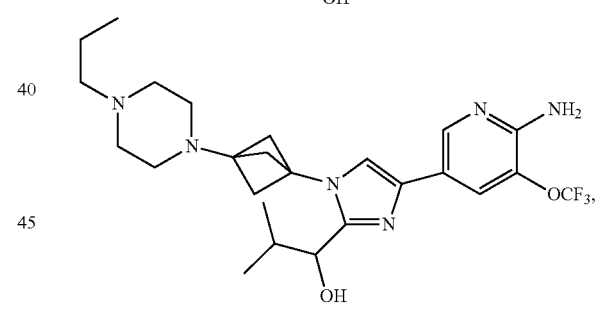
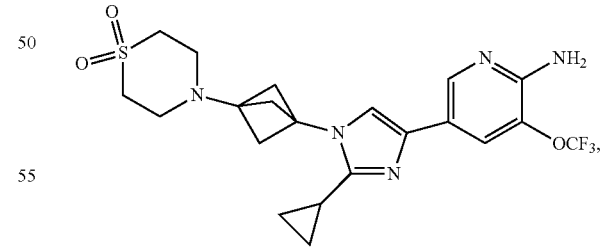
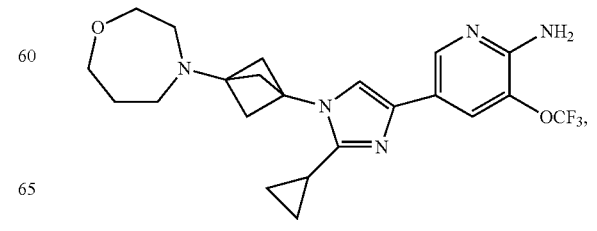

-continued
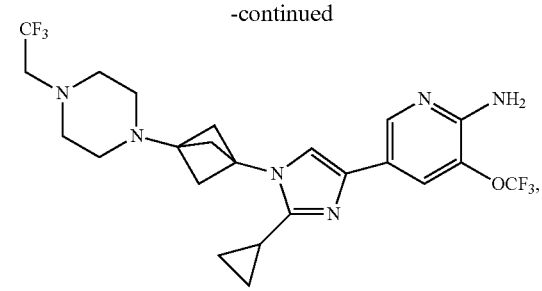
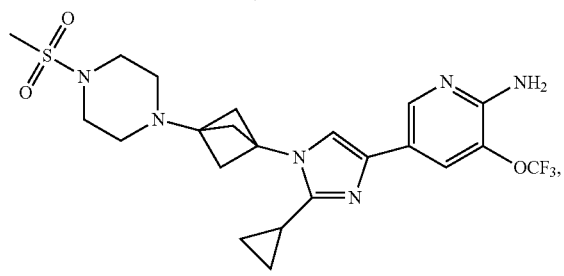
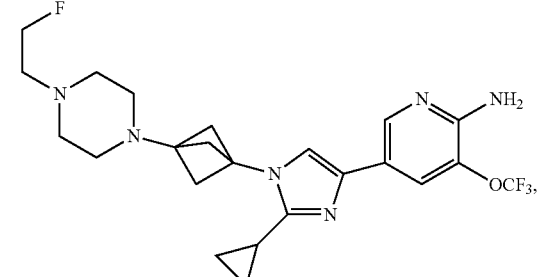
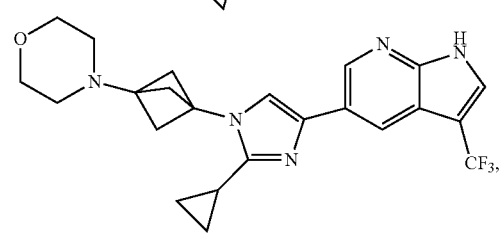
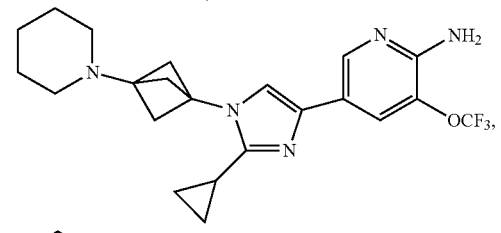
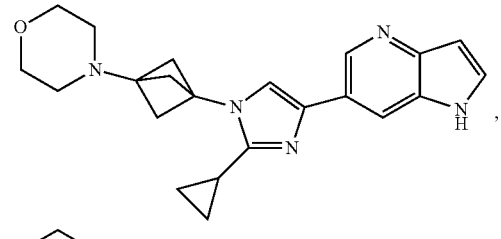
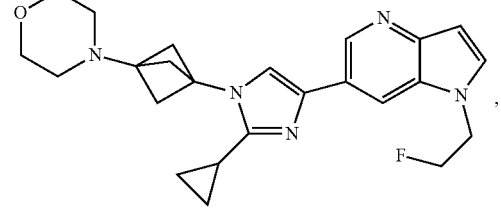
-continued
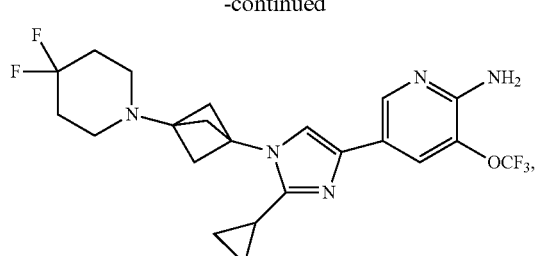
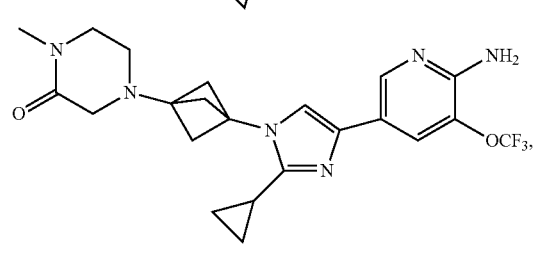
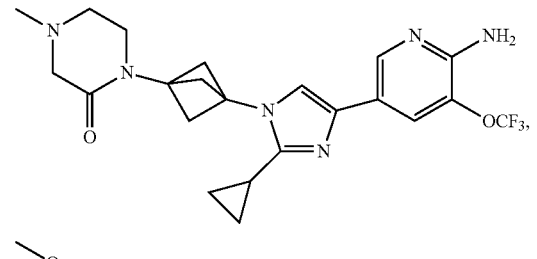
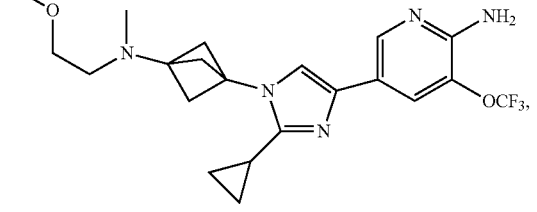
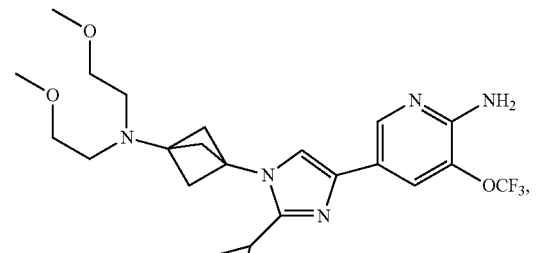
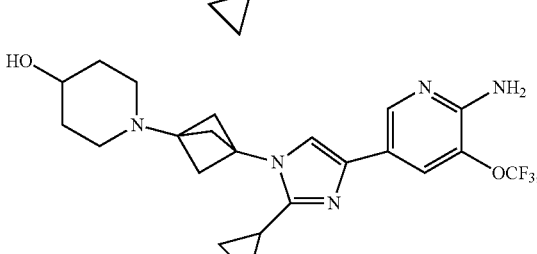
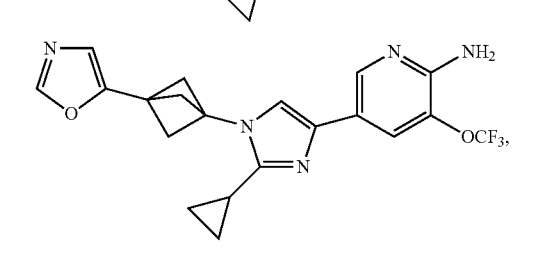

-continued

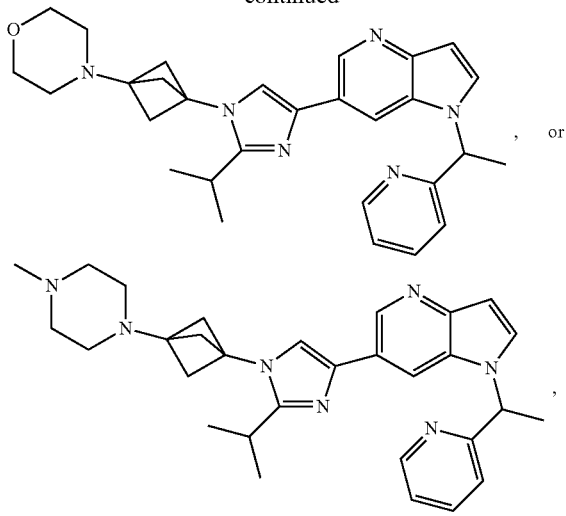

or a pharmaceutically acceptable salt thereof.

23. A method of treating chemotherapy-induced peripheral neuropathy (CIPN) comprising administering to a patient in need thereof, a therapeutically effective amount of a compound of Formula I:

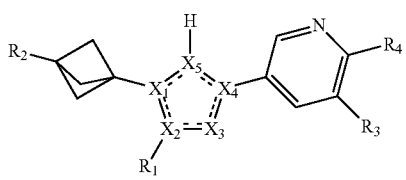
(I)

or a pharmaceutically acceptable salt thereof,
wherein:
$X_1$ is selected from C or N;
$X_2$ is selected from C or N;
exactly one of $X_1$ and $X_2$ is N;
$X_3$ is N;
$X_4$ and $X_5$ are C;
$X_1$, $X_2$, $X_3$, $X_4$, and Xs form a five membered heteroaryl;
$R_1$ is selected from alkyl, cycloalkyl, or heterocycloalkyl, any of which is optionally substituted with one to three $R_5$ groups;
$R_2$ is H or is selected from alkyl, amino, aryl, cycloalkyl, haloalkyl, heteroalkyl, heteroaryl, heterocycloalkyl, or sulfonylalkyl, any of which is optionally substituted with one to three $R_6$ groups;
$R_3$ is selected from H, alkyl, (alkoxy)alkyl, (arylalkoxy) alkyl, (heteroarylalkoxy)alkyl, cyano, cycloalkyl, halo, haloalkoxy, or haloalkyl;
$R_4$ is $N(R_{4a})_2$, wherein each $R_{4a}$ is independently selected from hydrogen, $C_{1-4}$alkyl, or $C_{1-4}$haloalkyl;
or $R_3$ and $R_4$ together with the atoms to which they are attached form a 5- or 6-membered heteroayl or heteroalkyl ring, optionally substituted with one to three $R_7$ groups;
each $R_5$ and $R_6$ is independently selected from $C_{1-4}$alkyl, $C_{1-4}$haloalkyl, $C_{1-4}$alkoxy, $C_{1-4}$ haloalkoxy, $C_{1-4}$alkylthio, $C_{1-4}$haloalkylthio, aryl, heteroaryl, $C_{3-7}$cycloalkyl, $C_{3-7}$heterocycloalkyl, (aryl)$C_{1-4}$alkyl, (heteroaryl)$C_{1-4}$alkyl, ($C_{3-7}$cycloalkyl)$C_{1-4}$alkyl, ($C_{3-7}$heterocycloalkyl)$C_{1-4}$alkyl, (ethenyl)$C_{1-4}$alkyl, (ethynyl)$C_{1-4}$alkyl, (aryl)$C_{1-4}$alkoxy, (heteroaryl)$C_{1-4}$alkoxy, ($C_{3-7}$cycloalkyl)$C_{1-4}$alkoxy, ($C_{3-7}$heterocycloalkyl)$C_{1-4}$alkoxy, (aryl)$C_{1-4}$alkylthio, (heteroaryl)$C_{1-4}$alkylthio, ($C_{3-7}$cycloalkyl)$C_{1-4}$alkylthio, ($C_{3-7}$heterocycloalkyl)$C_{1-4}$alkylthio, amino, halo, hydroxy, cyano, oxo; and each $R_7$ is independently selected from $C_{1-4}$alkyl, $C_{1-4}$haloalkyl, $C_{1-4}$alkoxy, $C_{1-4}$haloalkoxy, aryl, heteroaryl, $C_{3-7}$cycloalkyl, $C_{3-7}$heterocycloalkyl, (aryl)$C_{1-4}$alkyl, (heteroaryl)$C_{1-4}$alkyl, ($C_{3-7}$cycloalkyl)$C_{1-4}$alkyl, ($C_{3-7}$heterocycloalkyl)$C_{1-4}$alkyl, halo, hydroxy, cyano, or oxo.

24. A method of treating chemotherapy-induced cognitive impairment (CICI) comprising administering to a patient in need thereof, a therapeutically effective amount of a compound of Formula I:

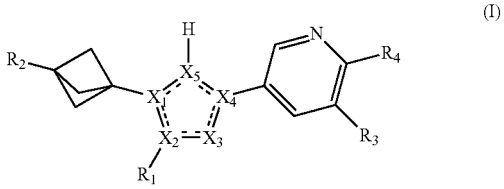
(I)

or a pharmaceutically acceptable salt thereof,
wherein:
$X_1$ is selected from C or N;
$X_2$ is selected from C or N;
exactly one of $X_1$ and $X_2$ is N;
$X_3$ is N;
$X_4$ and $X_5$ are C;
$X_1$, $X_2$, $X_3$, $X_4$, and $X_5$ form a five membered heteroaryl;
$R_1$ is selected from alkyl, cycloalkyl, or heterocycloalkyl, any of which is optionally substituted with one to three $R_5$ groups;
$R_2$ is H or is selected from alkyl, amino, aryl, cycloalkyl, haloalkyl, heteroalkyl, heteroaryl, heterocycloalkyl, or sulfonylalkyl, any of which is optionally substituted with one to three $R_6$ groups;
$R_3$ is selected from H, alkyl, (alkoxy)alkyl, (arylalkoxy) alkyl, (heteroarylalkoxy)alkyl, cyano, cycloalkyl, halo, haloalkoxy, or haloalkyl;
$R_4$ is $N(R_{4a})_2$, wherein each $R_{4a}$ is independently selected from hydrogen, $C_{1-4}$alkyl, or $C_{1-4}$haloalkyl;
or $R_3$ and $R_4$ together with the atoms to which they are attached form a 5- or 6-membered heteroayl or heteroalkyl ring, optionally substituted with one to three $R_7$ groups;
each $R_5$ and $R_6$ is independently selected from $C_{1-4}$alkyl, $C_{1-4}$haloalkyl, $C_{1-4}$alkoxy, $C_{1-4}$haloalkoxy, $C_{1-4}$alkylthio, $C_{1-4}$haloalkylthio, aryl, heteroaryl, $C_{3-7}$cycloalkyl, $C_{3-7}$heterocycloalkyl, (aryl)$C_{1-4}$-alkyl, (heteroaryl)$C_{1-4}$alkyl, ($C_{3-7}$cycloalkyl)$C_{1-4}$alkyl, ($C_{3-7}$heterocycloalkyl)$C_{1-4}$alkyl, (ethenyl)$C_{1-4}$alkyl, (ethynyl)$C_{1-4}$alkyl, (aryl)$C_{1-4}$alkoxy, (heteroaryl)$C_{1-4}$alkoxy, ($C_{3-7}$cycloalkyl)$C_{1-4}$alkoxy, ($C_{3-7}$heterocycloalkyl)$C_{1-4}$alkoxy, (aryl)$C_{1-4}$alylthio, (heteroaryl)$C_{1-4}$alkylthio, ($C_{3-7}$cycloalkyl)$C_{1-4}$alkylthio, ($C_{3-7}$heterocycloalkyl)$C_{1-4}$alkylthio, amino, halo, hydroxy, cyano, or oxo; and each $R_7$ is independently selected from $C_{1-4}$alkyl, $C_{1-4}$haloalkyl, $C_{1-4}$alkoxy, $C_{1-4}$haloalkoxy, aryl, heteroaryl, $C_{3-7}$cycloalkyl, $C_{3-7}$heterocycloalkyl, (aryl)$C_{1-4}$alkyl, (heteroaryl)$C_{1-4}$alkyl, ($C_{3-7}$cycloalkyl)$C_{1-4}$alkyl, ($C_{3-7}$heterocycloalkyl)$C_{1-4}$alkyl, halo, hydroxy, cyano, or oxo.

25. A method of treating chemotherapy-induced cognitive deficits (CICD) comprising administering to a patient in need thereof, a therapeutically effective amount of a compound of Formula I:

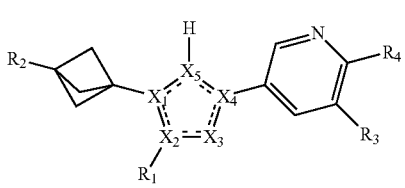

(I)

or a pharmaceutically acceptable salt thereof,
wherein:
$X_1$ is selected from C or N;
$X_2$ is selected from C or N;
exactly one of $X_1$ and $X_2$ is N;
$X_3$ is N;
$X_4$ and $X_5$ are C;
$X_1$, $X_2$, $X_3$, $X_4$, and $X_5$ form a five membered heteroaryl;
$R_1$ is selected from alkyl, cycloalkyl, or heterocycloalkyl, any of which is optionally substituted with one to three $R_5$ groups;
$R_2$ is H or is selected from alkyl, amino, aryl, cycloalkyl, haloalkyl, heteroalkyl, heteroaryl, heterocycloalkyl, or sulfonylalkyl, any of which is optionally substituted with one to three $R_6$ groups;
$R_3$ is selected from H, alkyl, (alkoxy)alkyl, (arylalkoxy)alkyl, (heteroarylalkoxy)alkyl, cyano, cycloalkyl, halo, haloalkoxy, or haloalkyl;
$R_4$ is $N(R_4)_2$, wherein each $R_{4a}$ is independently selected from hydrogen, $C_{1-4}$alkyl, or $C_{1-4}$haloalkyl;
or $R_3$ and $R_4$ together with the atoms to which they are attached form a 5- or 6-membered heteoayl or heteroalkyl ring, optionally substituted with one to three $R_7$ groups;
each $R_5$ and $R_6$ is independently selected from $C_{1-4}$alkyl, $C_{1-4}$haloalkyl, $C_{1-4}$alkoxy, $C_{1-4}$haloalkoxy, $C_{1-4}$-alkylthio, $C_{1-4}$haloalkylthio, aryl, heteroaryl, $C_{3-7}$cycloalkyl, $C_{3-7}$heterocycloalkyl, (aryl)$C_{1-4}$alkyl, (heteroaryl)$C_{1-4}$alkyl, ($C_{3-7}$cycloalkyl)$C_{1-4}$alkyl, ($C_{3-7}$heterocycloalkyl)$C_{1-4}$alkyl, (ethenyl)$C_{1-4}$alkyl, (ethynyl)$C_{1-4}$alkyl, (aryl)$C_{1-4}$alkoxy, (heteroaryl)$C_{1-4}$alkoxy, ($C_{3-7}$cycloalkyl)$C_{1-4}$alkoxy, ($C_{3-7}$heterocycloalkyl)$C_{1-4}$alkoxy, (aryl)$C_{1-4}$alylthio, (heteroaryl)$C_{1-4}$alkylthio, ($C_{3-7}$cycloalkyl)$C_{1-4}$alkylthio, ($C_{3-7}$heterocycloalkyl)$C_{1-4}$alkylthio, amino, halo, hydroxy, cyano, or oxo; and
each $R_7$ is independently selected from $C_{1-4}$alkyl, $C_{1-4}$haloalkyl, $C_{1-4}$alkoxy, $C_{1-4}$ haloalkoxy, aryl, heteroaryl, $C_{3-7}$cycloalkyl, $C_{3-7}$heterocycloalkyl, (aryl)$C_{1-4}$alkyl, (heteroaryl)$C_{1-4}$alkyl, ($C_{3-7}$cycloalkyl)$C_{1-4}$alkyl, ($C_{3-7}$heterocycloalkyl)$C_{1-4}$alkyl, halo, hydroxy, cyano, or oxo.

26. A method of treating Parkinson's disease comprising administering to a patient in need thereof, a therapeutically effective amount of a compound of Formula I:

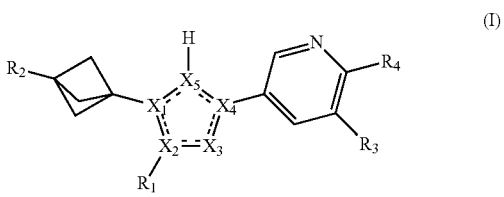

(I)

or a pharmaceutically acceptable salt thereof,
wherein:
$X_1$ is selected from C or N;
$X_2$ is selected from C or N;
exactly one of $X_1$ and $X_2$ is N;
$X_3$ is N;
$X_4$ and $X_5$ are C;
$X_1$, $X_2$, $X_3$, $X_4$, and $X_5$ form a five membered heteroaryl;
$R_1$ is selected from alkyl, cycloalkyl, or heterocycloalkyl, any of which is optionally substituted with one to three $R_5$ groups;
$R_2$ is H or is selected from alkyl, amino, aryl, cycloalkyl, haloalkyl, heteroalkyl, heteroaryl, heterocycloalkyl, or sulfonylalkyl, any of which is optionally substituted with one to three $R_6$ groups;
$R_3$ is selected from H, alkyl, (alkoxy)alkyl, (arylalkoxy)alkyl, (heteroarylalkoxy)alkyl, cyano, cycloalkyl, halo, haloalkoxy, or haloalkyl;
$R_4$ is $N(R_{4a})_2$, wherein each $R_{4a}$ is independently selected from hydrogen, $C_{1-4}$alkyl, or $C_{1-4}$haloalkyl;
or $R_3$ and $R_4$ together with the atoms to which they are attached form a 5- or 6-membered heteoayl or heteroalkyl ring, optionally substituted with one to three $R_7$ groups;
each $R_5$ and $R_6$ is independently selected from $C_{1-4}$alkyl, $C_{1-4}$haloalkyl, $C_{1-4}$alkoxy, $C_{1-4}$haloalkoxy, $C_{1-4}$-alkylthio, $C_{1-4}$haloalkylthio, aryl, heteroaryl, $C_{3-7}$cycloalkyl, $C_{3-7}$heterocycloalkyl, (aryl)$C_{1-4}$alkyl, (heteroaryl)$C_{1-4}$alkyl, ($C_{3-7}$cycloalkyl)$C_{1-4}$alkyl, ($C_{3-7}$heterocycloalkyl)$C_{1-4}$alkyl, (ethenyl)$C_{1-4}$alkyl, (ethynyl)$C_{1-4}$alkyl, (aryl)$C_{1-4}$alkoxy, (heteroaryl)$C_{1-4}$alkoxy, ($C_{3-7}$cycloalkyl)$C_{1-4}$alkoxy, ($C_{3-7}$heterocycloalkyl)$C_{1-4}$alkoxy, (aryl)$C_{1-4}$alylthio, (heteroaryl)$C_{1-4}$alkylthio, ($C_3$cycloalkyl)$C_{1-4}$alkylthio, ($C_{3-7}$heterocycloalkyl)$C_{1-4}$alkylthio, amino, halo, hydroxy, cyano, or oxo; and
each $R_7$ is independently selected from $C_{1-4}$alkyl, $C_{1-4}$haloalkyl, $C_{1-4}$alkoxy, $C_{1-4}$haloalkoxy, aryl, heteroaryl, $C_{3-7}$cycloalkyl, $C_{3-7}$heterocycloalkyl, (aryl)$C_{1-4}$alkyl, (heteroaryl)$C_{1-4}$alkyl, ($C_{3-7}$cycloalkyl)$C_{1-4}$alkyl, ($C_{3-7}$heterocycloalkyl)$C_{1-4}$alkyl, halo, hydroxy, cyano, or oxo.

27. The method of claim 23, where the compound is

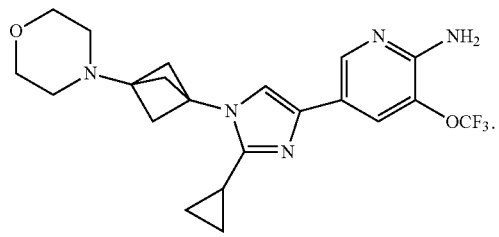 [SMILES: Nc1ncc(-c2cn(C34CC(N5CCOCC5)(C3)C4)c(C3CC3)n2)cc1OC(F)(F)F]

28. The method of claim 23, where the compound is

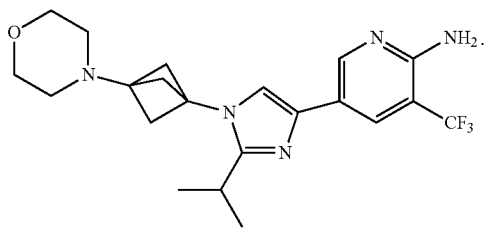 [SMILES: CC(C)c1nc(-c2cnc(N)c(C(F)(F)F)c2)cn1C12CC(N3CCOCC3)(C1)C2]

29. The method of claim 23, where the compound is

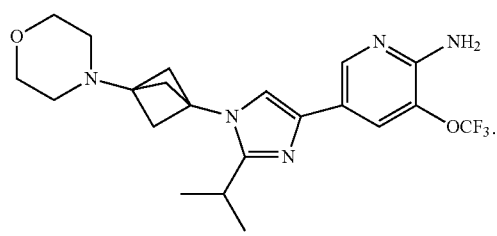 [SMILES: CC(C)c1nc(-c2cnc(N)c(OC(F)(F)F)c2)cn1C12CC(N3CCOCC3)(C1)C2]

30. The method of claim 23, where the compound is

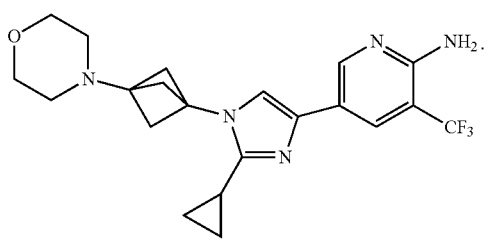 [SMILES: Nc1ncc(-c2cn(C34CC(N5CCOCC5)(C3)C4)c(C3CC3)n2)cc1C(F)(F)F]

31. The method of claim 23, where the compound is

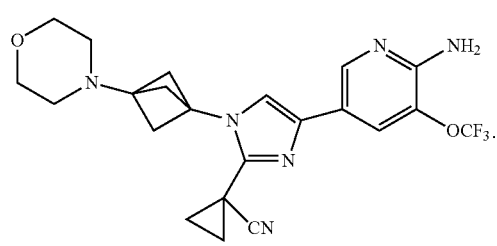 [SMILES: N#CC1(c2nc(-c3cnc(N)c(OC(F)(F)F)c3)cn2C23CC(N4CCOCC4)(C2)C3)CC1]

32. The method of claim 24, where the compound is

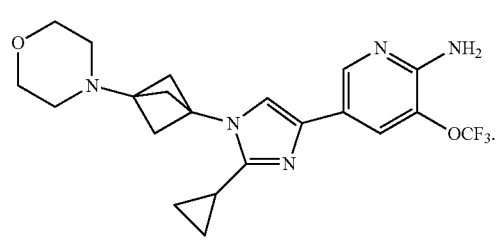 [SMILES: Nc1ncc(-c2cn(C34CC(N5CCOCC5)(C3)C4)c(C3CC3)n2)cc1OC(F)(F)F]

33. The method of claim 24, where the compound is

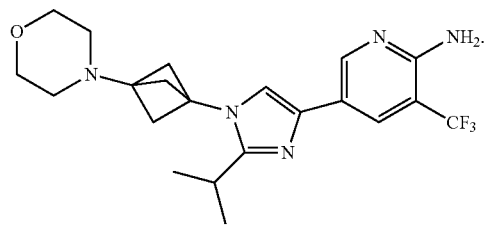 [SMILES: CC(C)c1nc(-c2cnc(N)c(C(F)(F)F)c2)cn1C12CC(N3CCOCC3)(C1)C2]

34. The method of claim 24, where the compound is

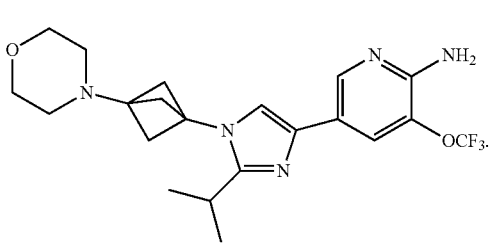 [SMILES: CC(C)c1nc(-c2cnc(N)c(OC(F)(F)F)c2)cn1C12CC(N3CCOCC3)(C1)C2]

35. The method of claim 24, where the compound is

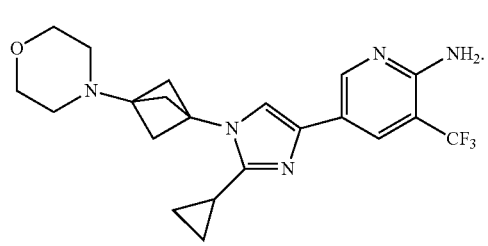 [SMILES: Nc1ncc(-c2cn(C34CC(N5CCOCC5)(C3)C4)c(C3CC3)n2)cc1C(F)(F)F]

36. The method of claim 24, where the compound is

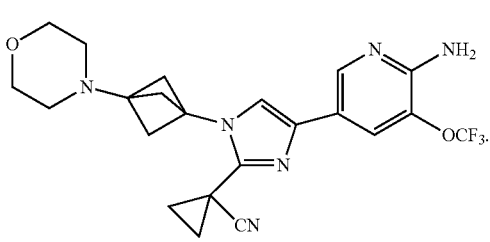 [SMILES: N#CC1(c2nc(-c3cnc(N)c(OC(F)(F)F)c3)cn2C23CC(N4CCOCC4)(C2)C3)CC1]

37. The method of claim 25, where the compound is

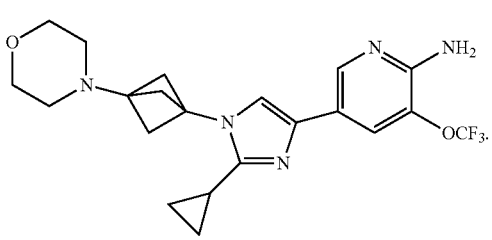 [SMILES: Nc1ncc(-c2cn(C34CC(N5CCOCC5)(C3)C4)c(C3CC3)n2)cc1OC(F)(F)F]

38. The method of claim 25, where the compound is

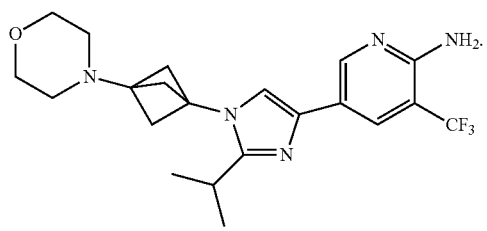 [SMILES: CC(C)c1nc(-c2cnc(N)c(C(F)(F)F)c2)cn1C12CC(N3CCOCC3)(C1)C2]

39. The method of claim 25, where the compound is

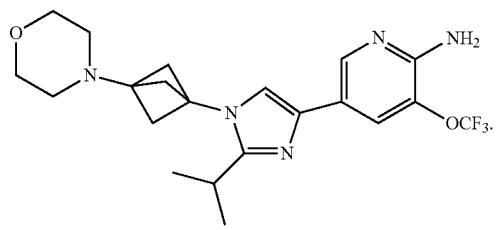 [SMILES: CC(C)c1nc(-c2cnc(N)c(OC(F)(F)F)c2)cn1C12CC(N3CCOCC3)(C1)C2]

40. The method of claim 25, where the compound is

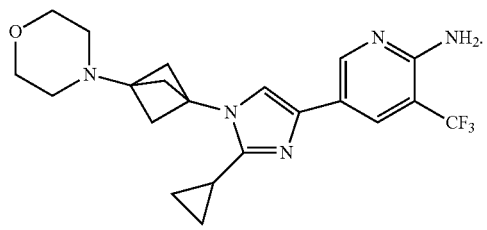 [SMILES: Nc1ncc(-c2cn(C34CC(N5CCOCC5)(C3)C4)c(C3CC3)n2)cc1C(F)(F)F]

41. The method of claim 25, where the compound is

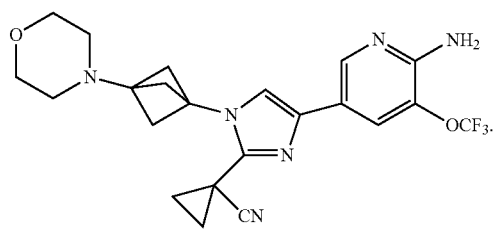 [SMILES: N#CC1(c2nc(-c3cnc(N)c(OC(F)(F)F)c3)cn2C23CC(N4CCOCC4)(C2)C3)CC1]

42. The method of claim 26, where the compound is

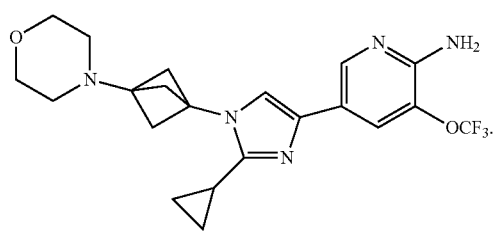 [SMILES: Nc1ncc(-c2cn(C34CC(N5CCOCC5)(C3)C4)c(C3CC3)n2)cc1OC(F)(F)F]

43. The method of claim 26, where the compound is

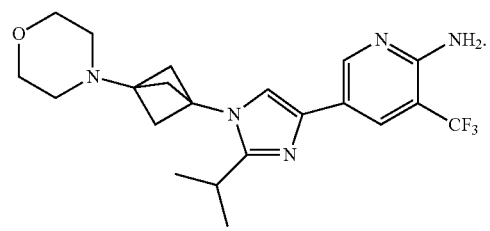 [SMILES: CC(C)c1nc(-c2cnc(N)c(C(F)(F)F)c2)cn1C12CC(N3CCOCC3)(C1)C2]

44. The method of claim 26, where the compound is

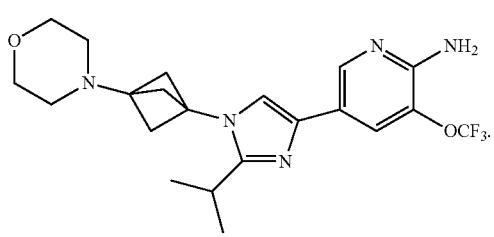 [SMILES: CC(C)c1nc(-c2cnc(N)c(OC(F)(F)F)c2)cn1C12CC(N3CCOCC3)(C1)C2]

45. The method of claim 26, where the compound is

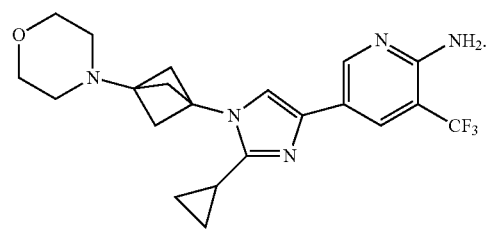

46. The method of claim 26, where the compound is

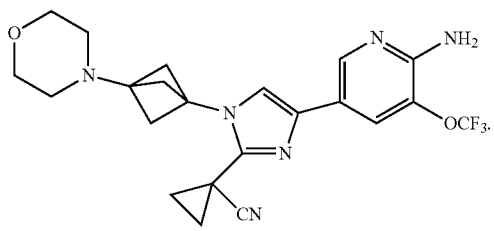 [SMILES: N#CC1(c2nc(-c3cnc(N)c(OC(F)(F)F)c3)cn2C23CC(N4CCOCC4)(C2)C3)CC1]

* * * * *

SEQUENCE LISTING

```
<160> NUMBER OF SEQ ID NOS: 1

<210> SEQ ID NO 1
<211> LENGTH: 10
<212> TYPE: DNA
<213> ORGANISM: Homo sapiens

<400> SEQUENCE: 1
gggaattccc                                                            10
```